US010092566B2

(12) United States Patent
Lee

(10) Patent No.: US 10,092,566 B2
(45) Date of Patent: Oct. 9, 2018

(54) COMPOSITION FOR CONTROLLING A GUT IMMUNITY AND USE THEREOF

(71) Applicant: SEOUL NATIONAL UNIVERSITY R&DB FOUNDATION, Seoul (KR)

(72) Inventor: Won Jae Lee, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 14/889,424

(22) PCT Filed: May 8, 2014

(86) PCT No.: PCT/KR2014/004072
§ 371 (c)(1),
(2) Date: Feb. 16, 2016

(87) PCT Pub. No.: WO2014/182078
PCT Pub. Date: Nov. 13, 2014

(65) Prior Publication Data
US 2016/0151371 A1 Jun. 2, 2016

(30) Foreign Application Priority Data

May 8, 2013 (KR) .................. 10-2013-0052133

(51) Int. Cl.
| | |
|---|---|
| *A61K 31/513* | (2006.01) |
| *A61K 31/01* | (2006.01) |
| *A61K 31/352* | (2006.01) |
| *A61K 31/353* | (2006.01) |
| *A61K 31/355* | (2006.01) |
| *A61K 31/375* | (2006.01) |
| *A61K 31/409* | (2006.01) |
| *A61K 31/522* | (2006.01) |
| *A61K 45/06* | (2006.01) |
| *A61K 31/505* | (2006.01) |
| *A61K 31/7072* | (2006.01) |
| *G06F 17/30* | (2006.01) |
| *A23L 33/10* | (2016.01) |

(52) U.S. Cl.
CPC ............ *A61K 31/513* (2013.01); *A23L 33/10* (2016.08); *A61K 31/01* (2013.01); *A61K 31/352* (2013.01); *A61K 31/353* (2013.01); *A61K 31/355* (2013.01); *A61K 31/375* (2013.01); *A61K 31/409* (2013.01); *A61K 31/505* (2013.01); *A61K 31/522* (2013.01); *A61K 31/7072* (2013.01); *A61K 45/06* (2013.01); *G06F 17/30598* (2013.01)

(58) Field of Classification Search
CPC .... A61K 31/01; A61K 31/352; A61K 31/353; A61K 31/355; A61K 31/375; A61K 31/409; A61K 31/513; A61K 31/522
See application file for complete search history.

(56) References Cited

PUBLICATIONS

Infectious disease self management, Mayo Clinic, 2016.*
Bae, et al., Trends in Immunology 31 (2010) 278-287.
Ha, et al., Nature Immunology vol. 10, No. 9, (Sep. 2009) pp. 949-957.
Ha, et al., Science, vol. 310 (Nov. 4, 2005) pp. 847-850.
Kim, et al., Frontiers in Cellular and Infection Microbiology, vol. 3 (Jan. 2014) pp. 1-12.
Lee, et al., Cell vol. 153(May 9, 2013) pp. 797-811.
Hooper, Nat Rev Microbiol vol. 7, pp. 367-374 (2009).
Lhocine et al., Cell Host Microbe vol. 7, pp. 147-158 (2008).
Paredes, et al., Immunity Vole 35, pp. 770-779 (2011).
Ryu et al., Science vol. 319, pp. 777-782 (2008).
Ha, et al., Dev Cell vol. 16, pp. 386-397 (2009).
Antioxidants get rid of "reactive oxygen species", a cause of aging, vol. 38(7). pp. 68-71 (2005). (English translation of abstract).

* cited by examiner

*Primary Examiner* — Zohreh A Fay
(74) *Attorney, Agent, or Firm* — Norton Rose Fulbright US LLP

(57) ABSTRACT

The present invention relates to an antimicrobial composition for uracil non-secretory (URA−) bacteria, comprising uracil, uracil precursors, uracil analogs, or uracil-secreting opportunistic pathogens as an active ingredient; and a composition for preventing cell damage caused by uracil-secretory (URA+) bacteria, comprising ROS scavengers as an active ingredient. The present invention also relates to food or feed for antimicrobial activity and preventing cell damage, comprising said composition; a method for controlling dual oxidase (DUOX) activation, the generation of reactive oxygen species (ROS), or the level thereof; a method for producing cells, wherein DUOX activation, the generation of ROS, or the level thereof are controlled; and a method for providing information on gut pathogenicity in isolated bacteria. The composition of the present invention has effects for preventing symptoms caused by bacteria according to a mechanism which has been unknown in the art. Further, the present invention can be efficiently utilized for establishing prevention and treatment strategies for symptoms caused by bacteria later, as therapeutic strategies can be readily established by bacterial classification based on criteria that can be easily confirmed.

5 Claims, 56 Drawing Sheets
Specification includes a Sequence Listing.

[Fig. 1a]
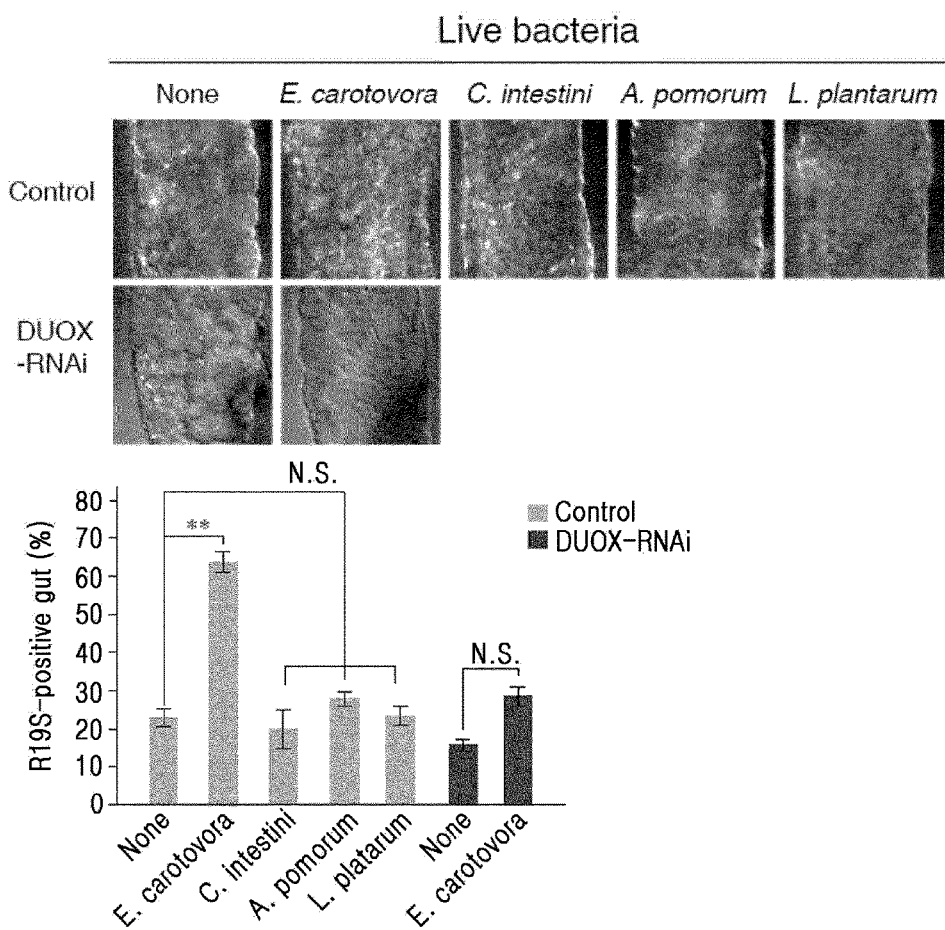

[Fig. 1b]
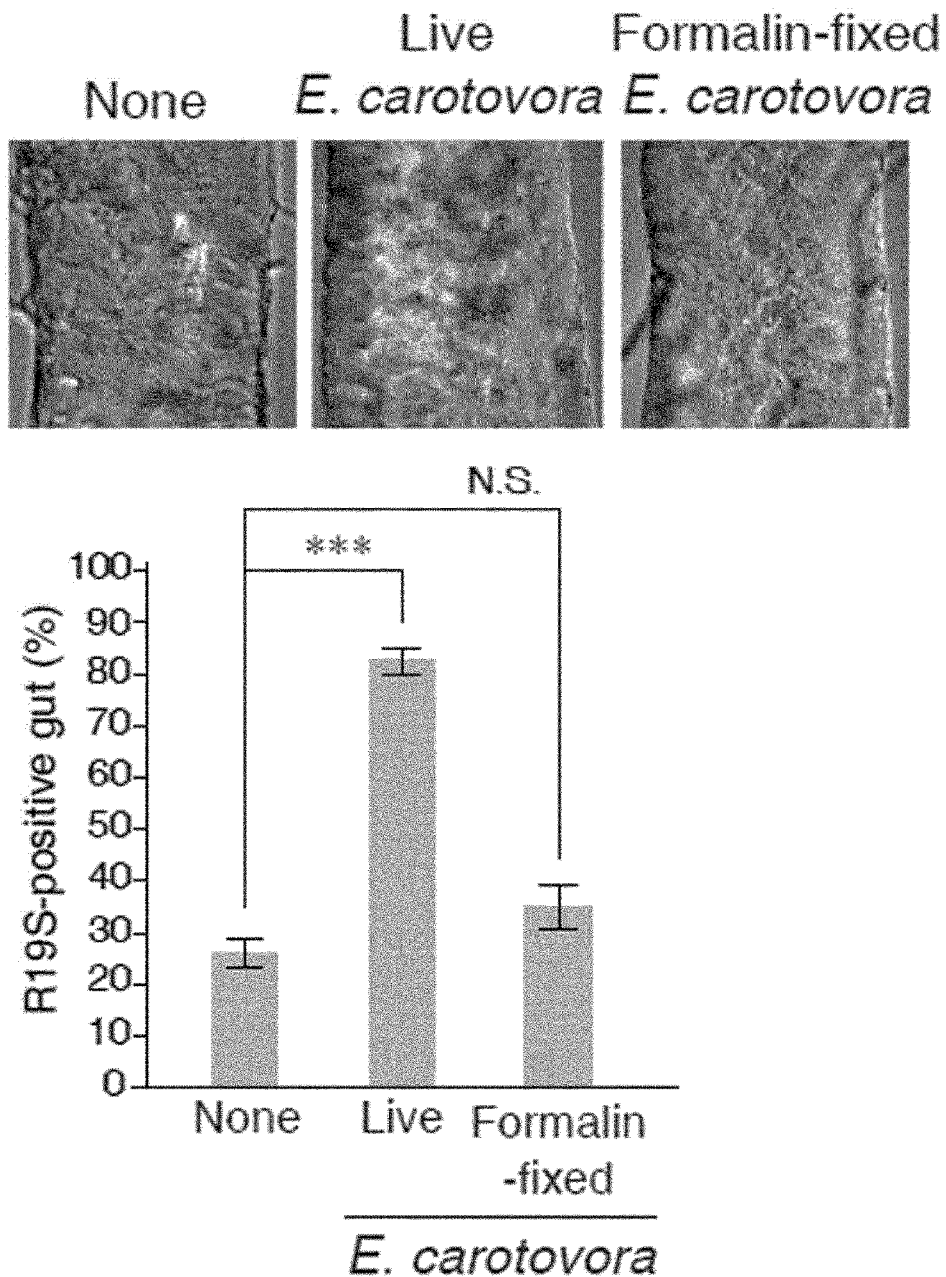

[Fig. 1c]
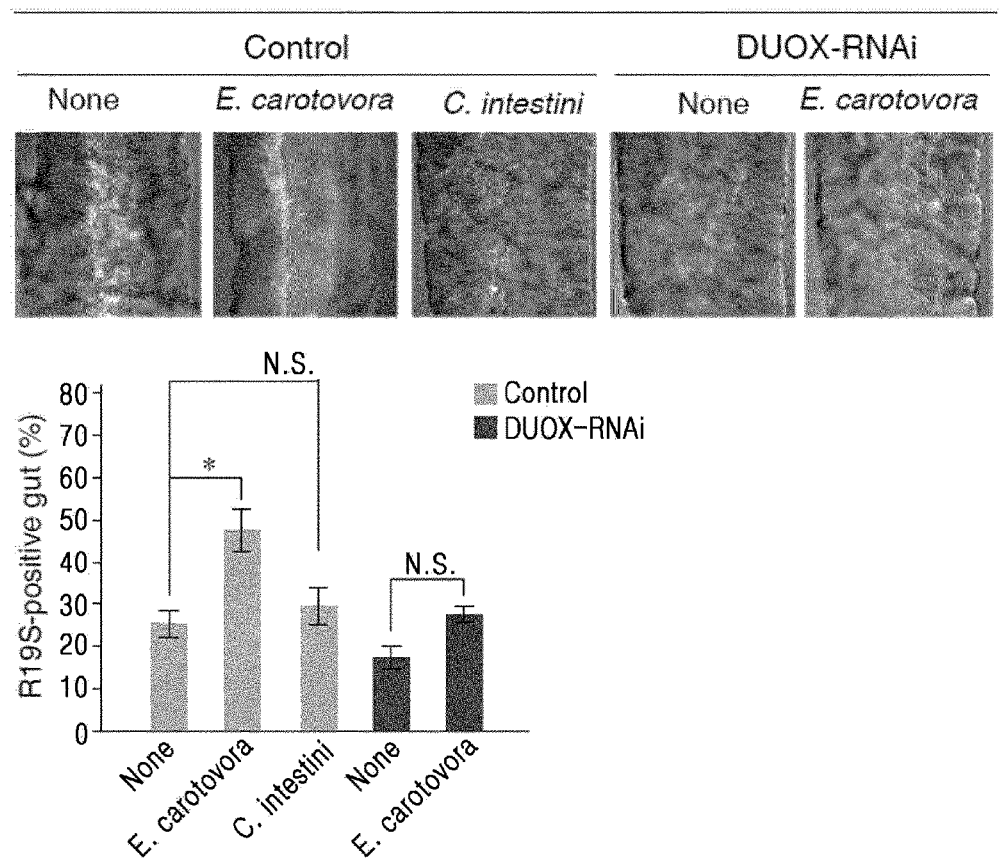

[Fig. 1d]
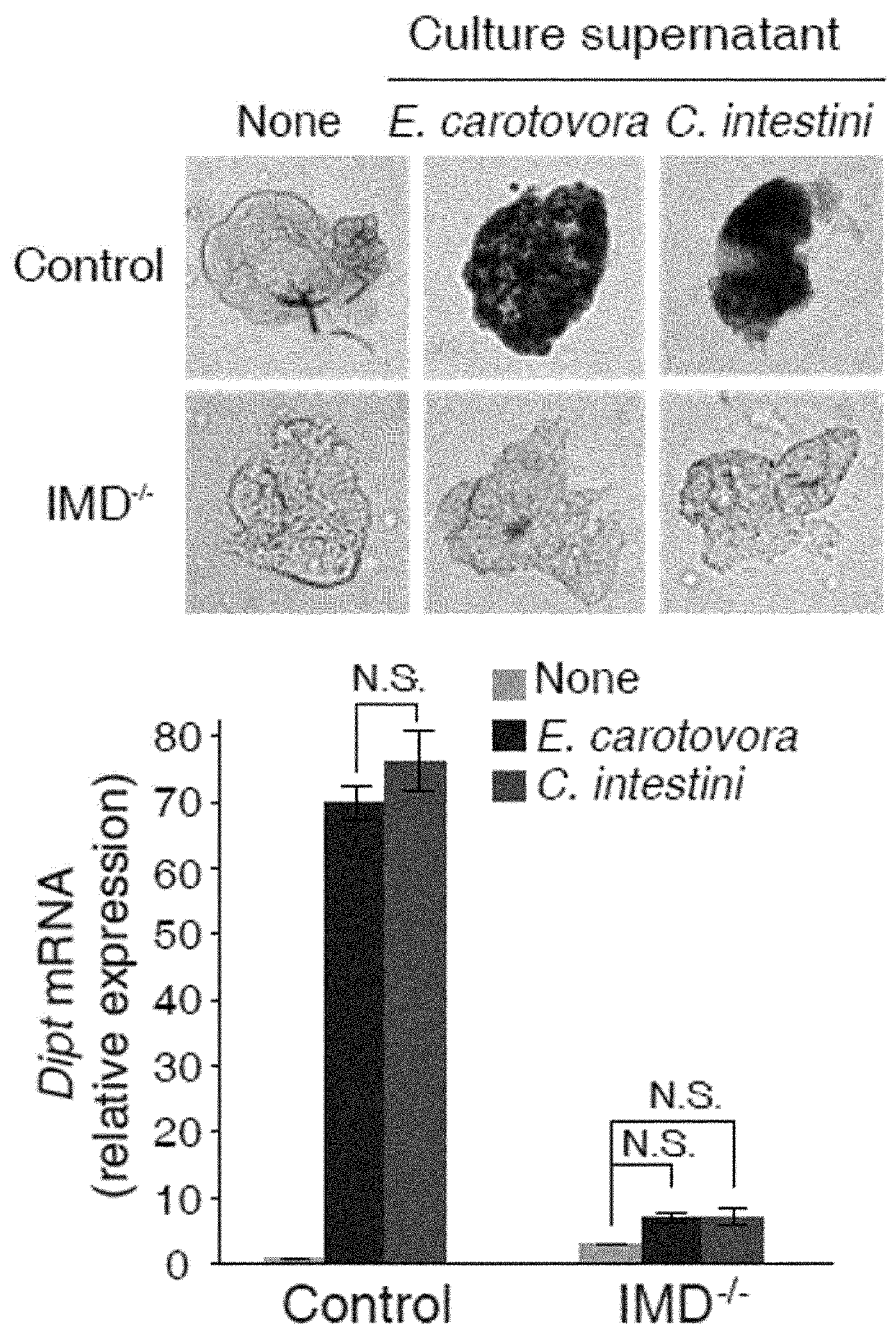

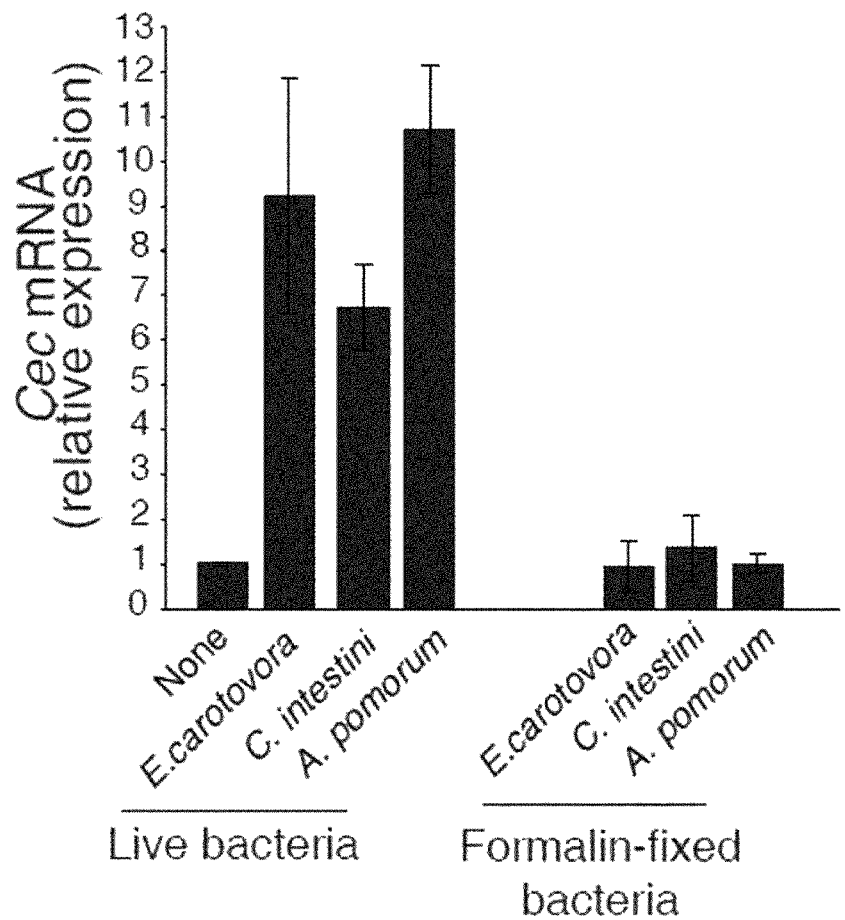
[Fig. 1e]

[Fig. 2a]
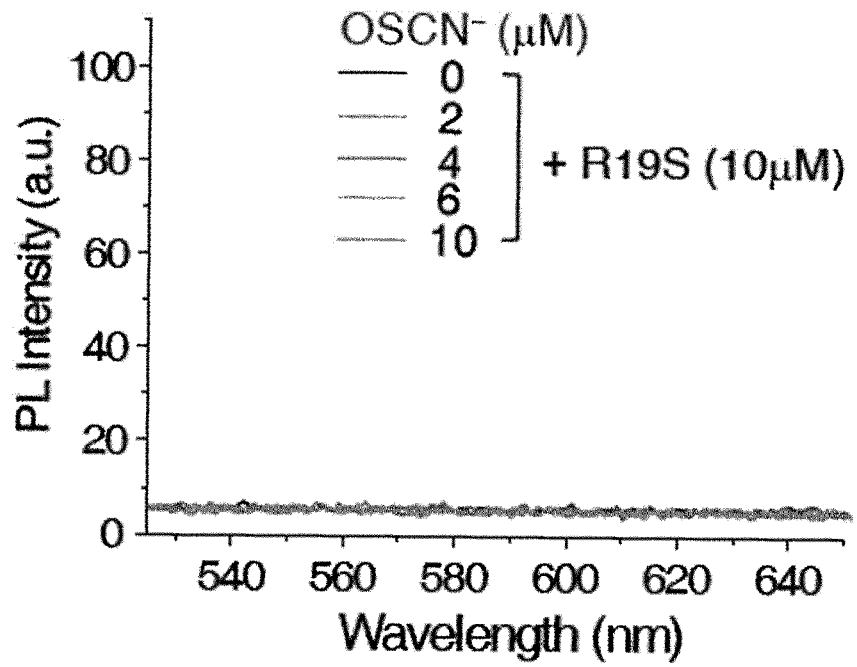
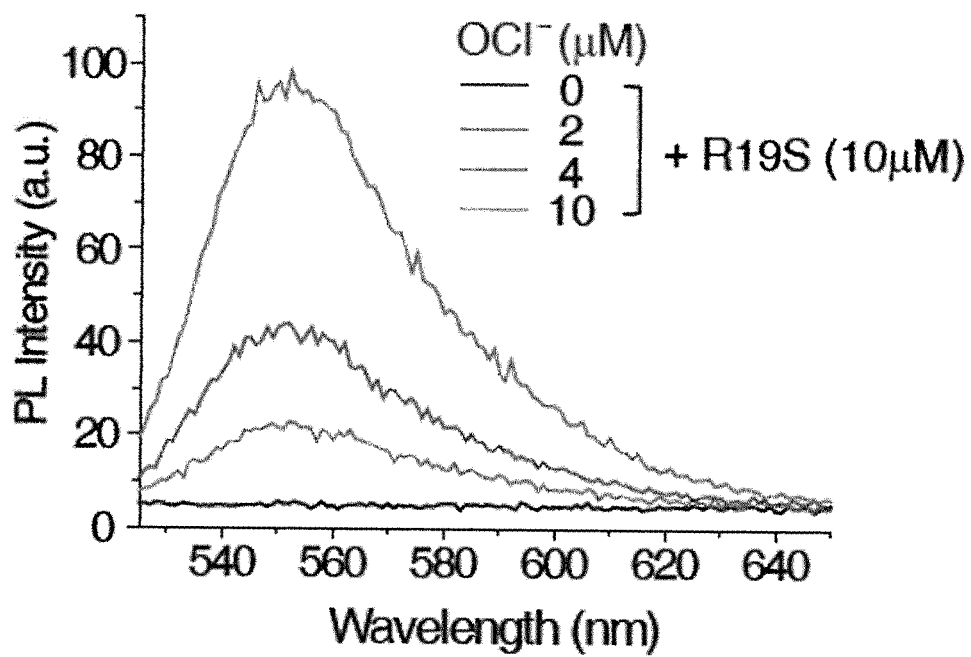

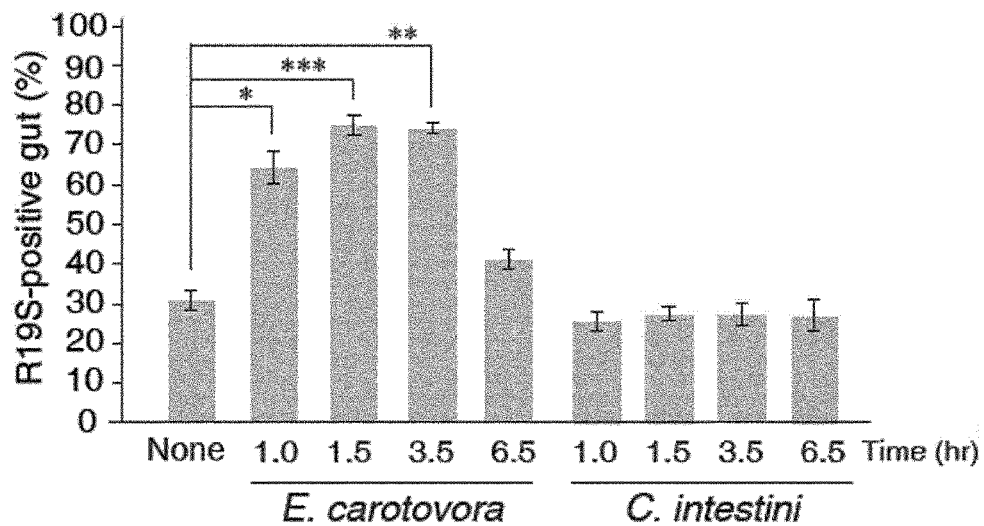

[Fig. 2c]
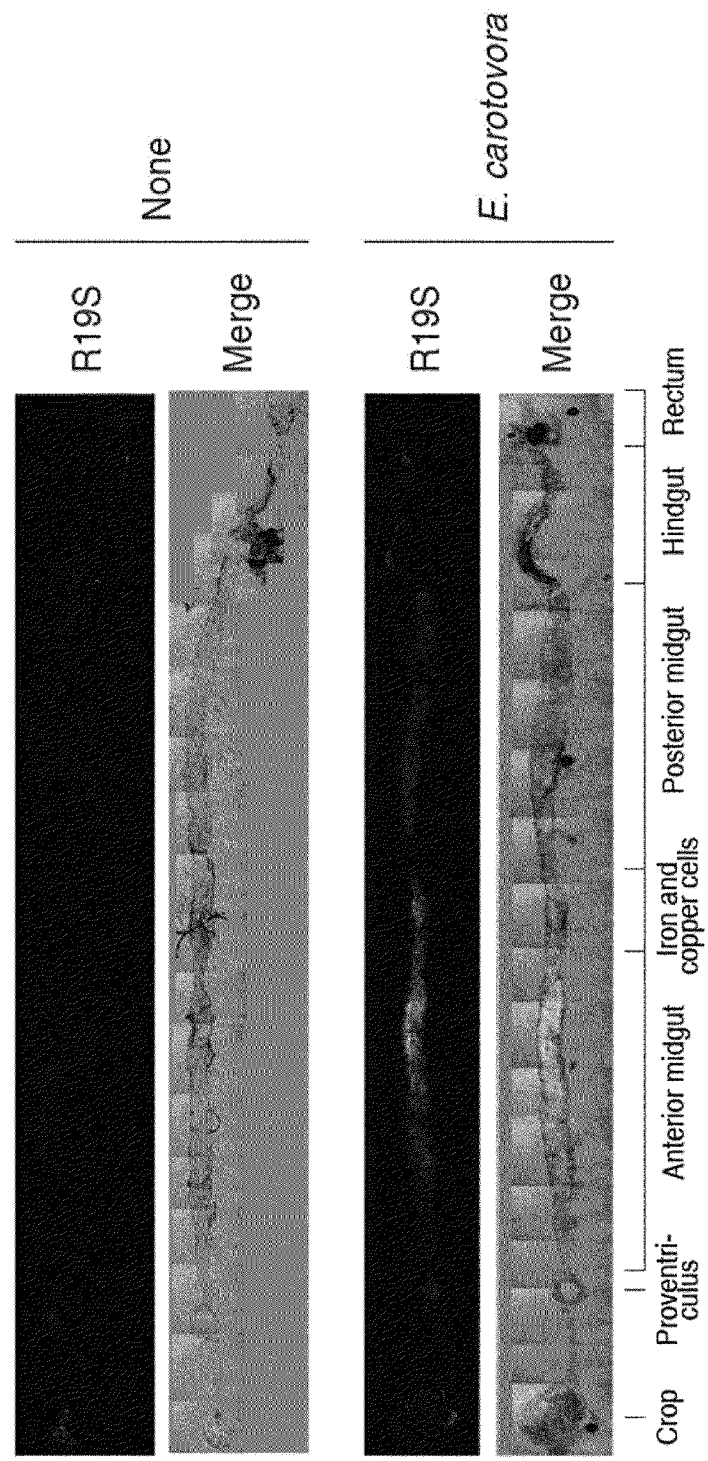

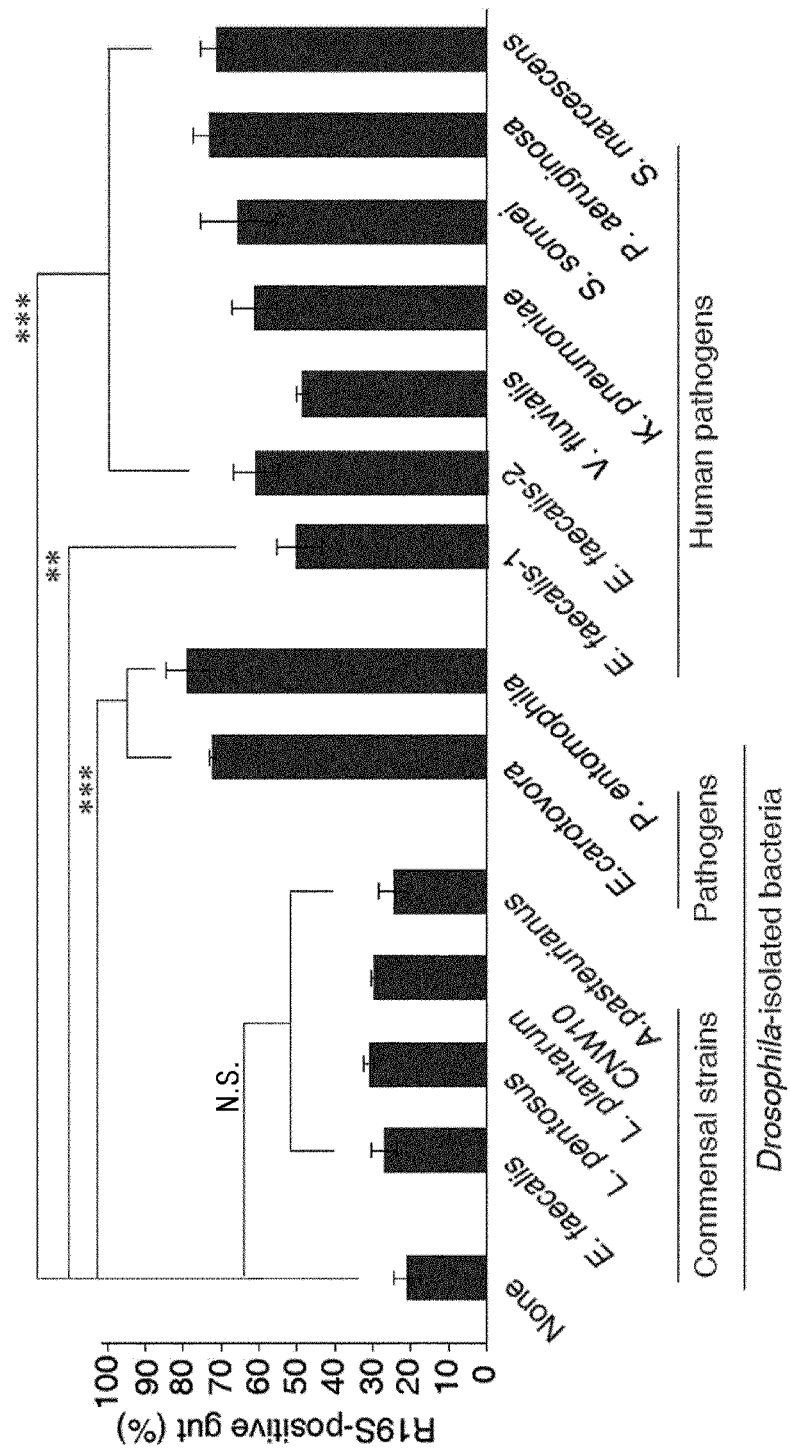
[Fig. 2d]

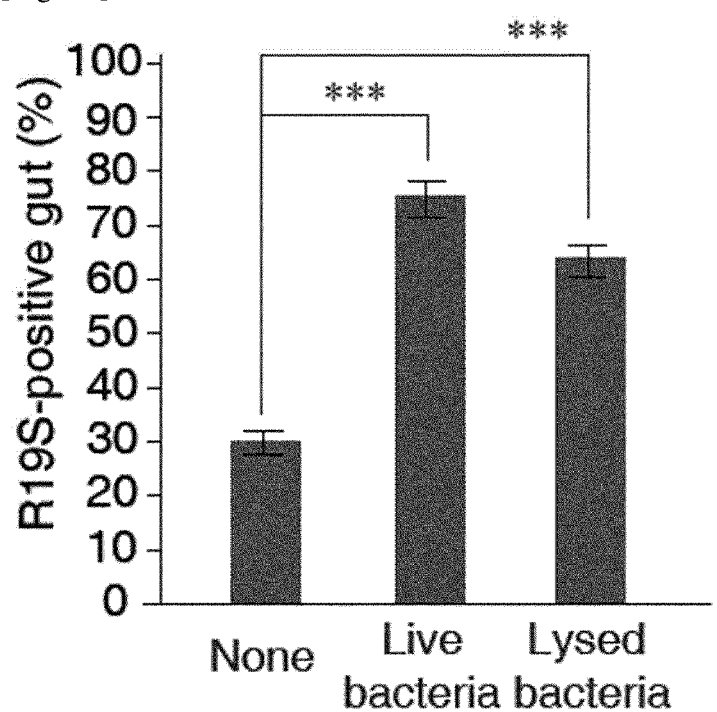
[Fig. 2e]

[Fig. 3a]
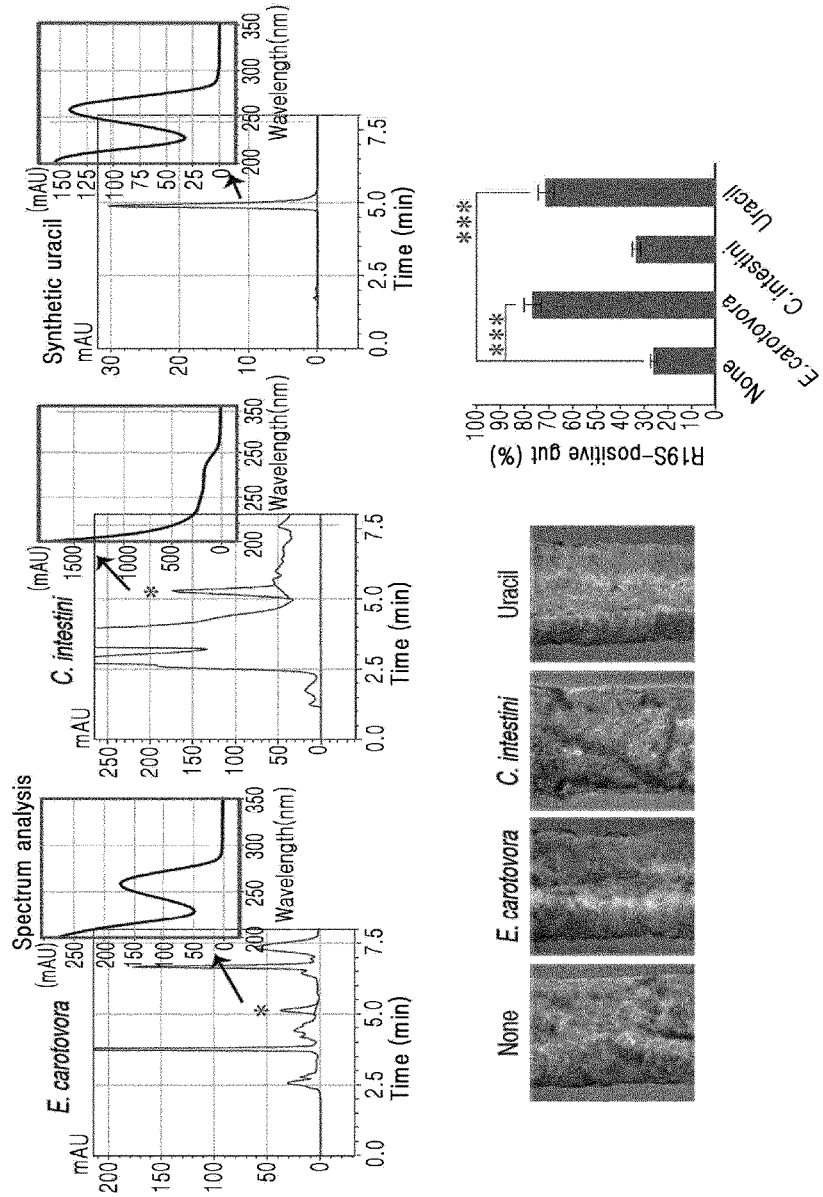
[Fig. 3b]
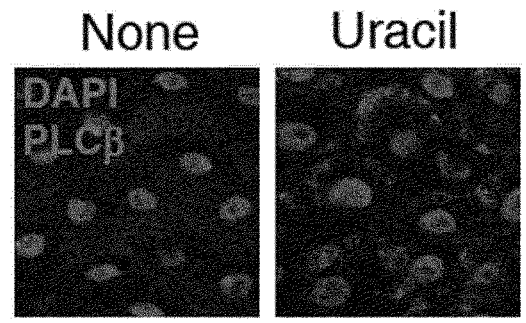

[Fig. 3c]
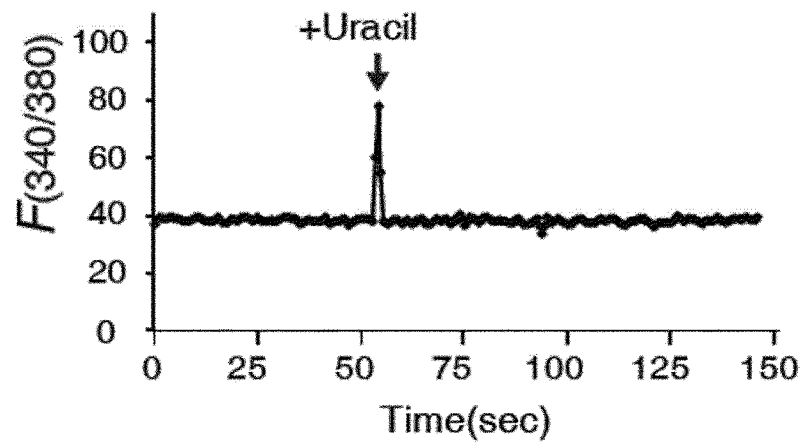
[Fig. 3d]
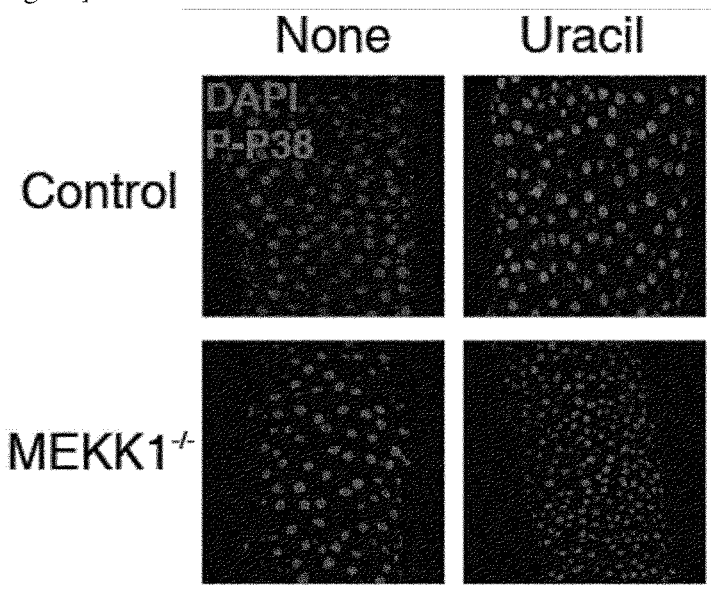

[Fig. 3e]
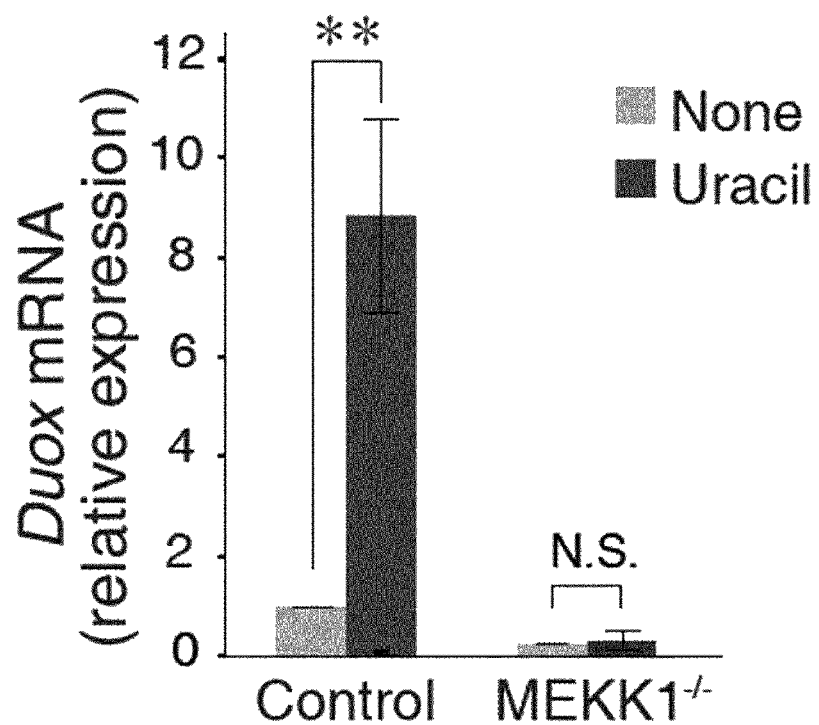

[Fig. 3f]
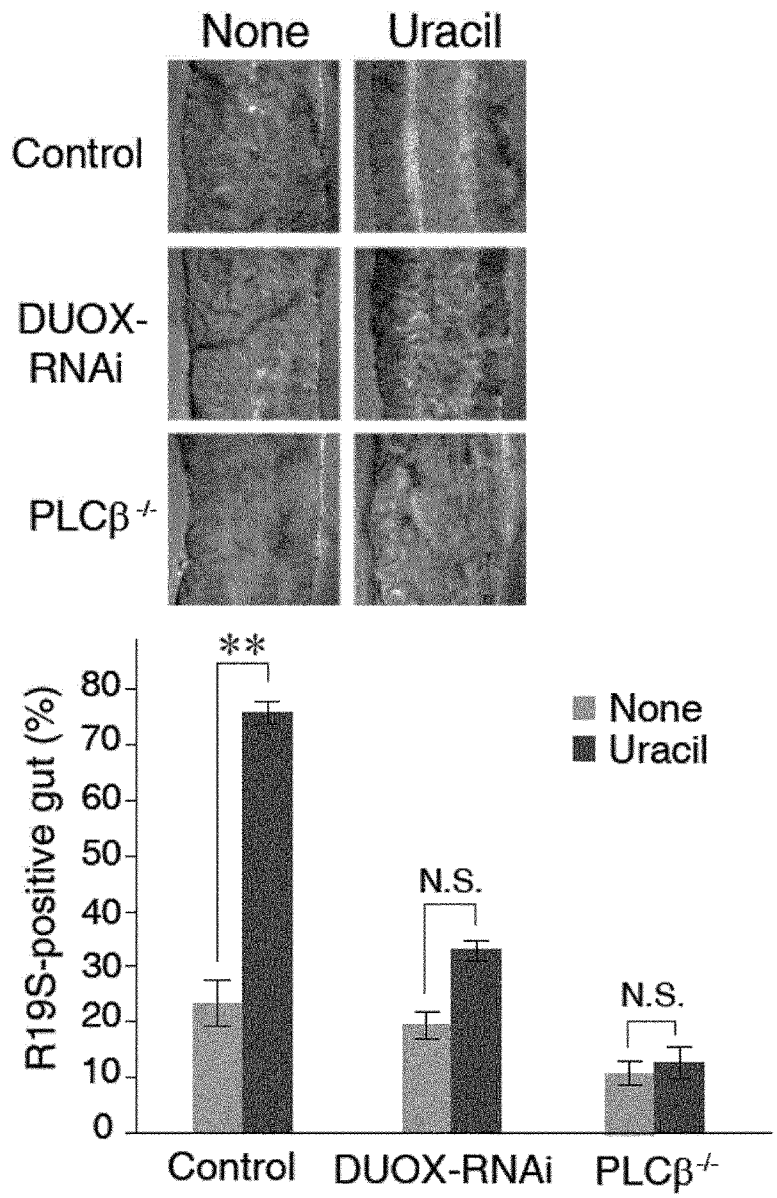

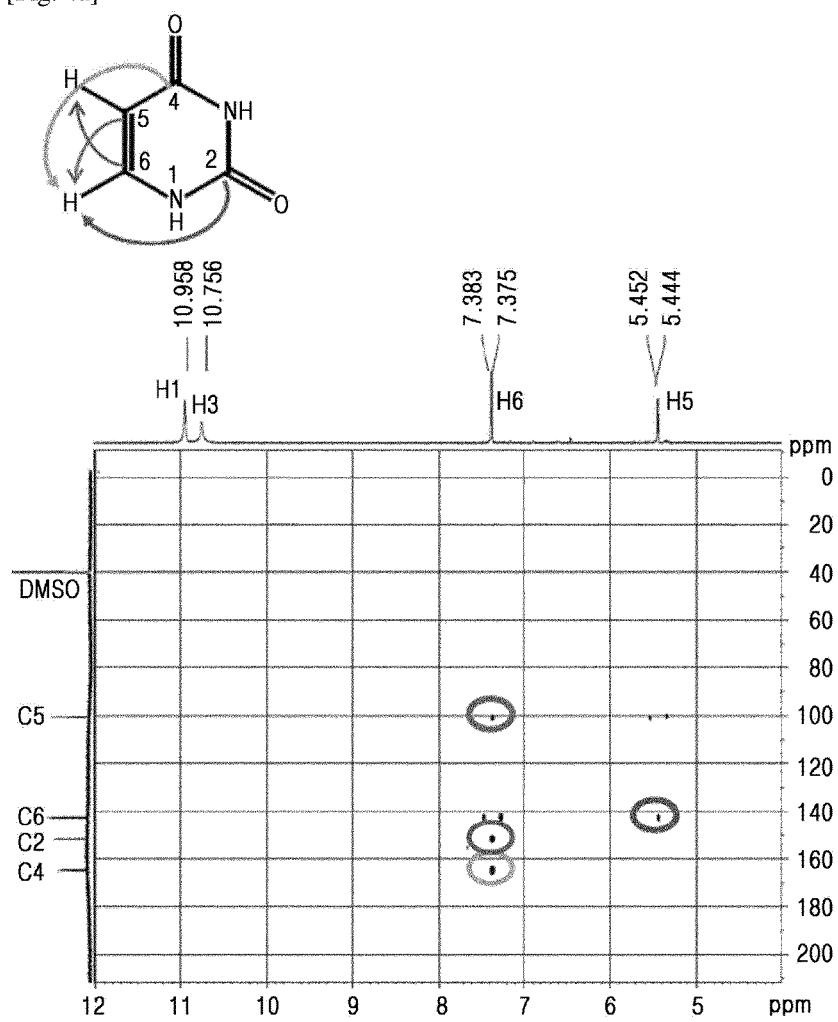
[Fig. 4a]

[Fig. 4b]
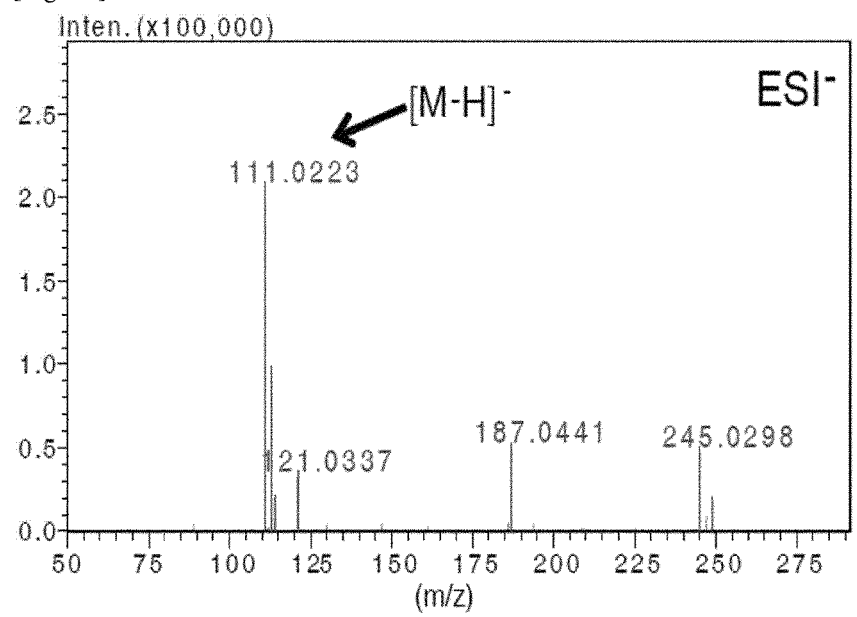
[Fig. 4c]
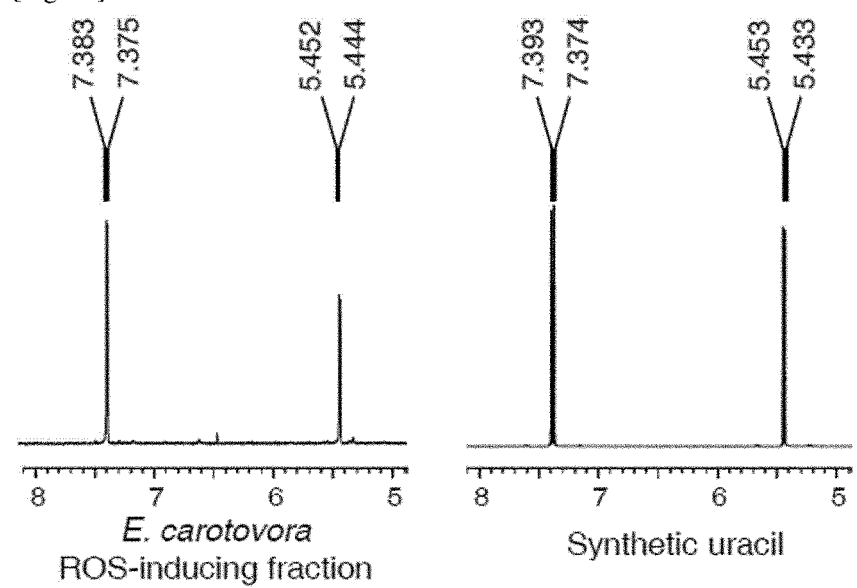
E. carotovora
ROS-inducing fraction
Synthetic uracil

[Fig. 4d]
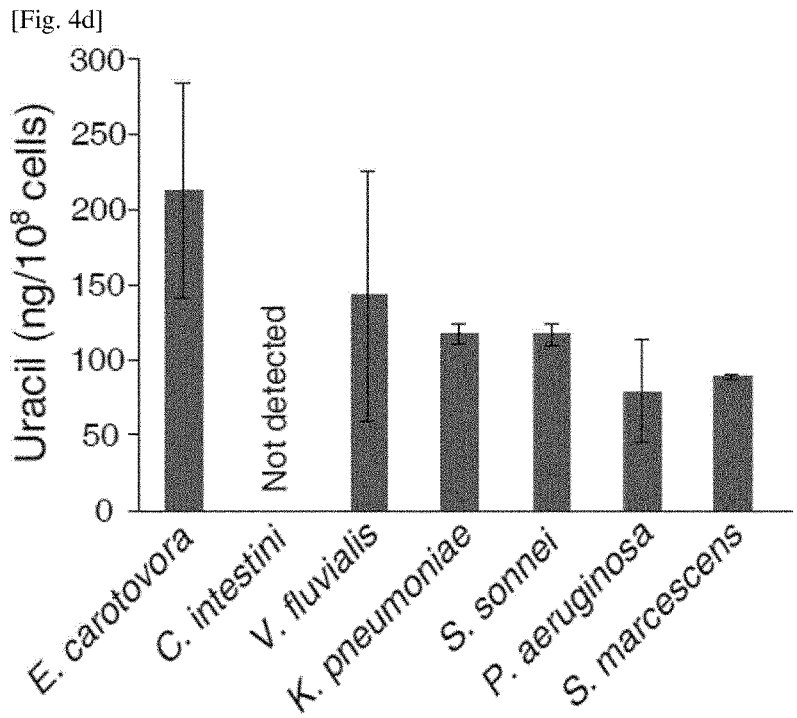
[Fig. 4e]
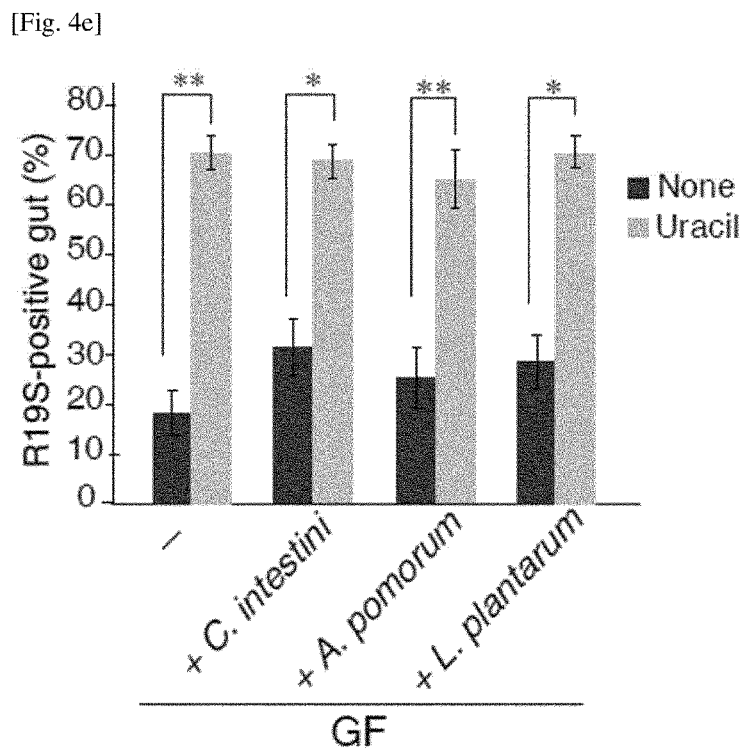

[Fig. 4f]
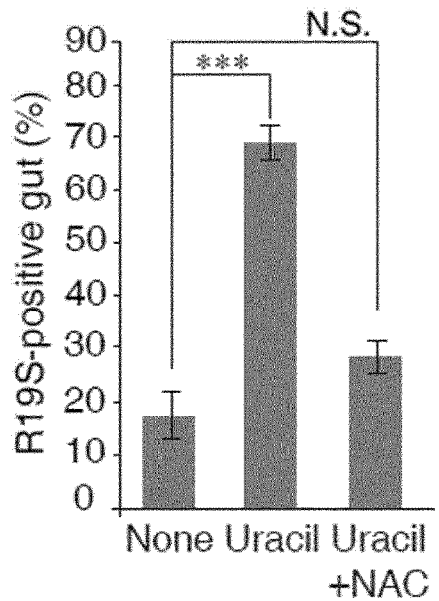
[Fig. 4g]
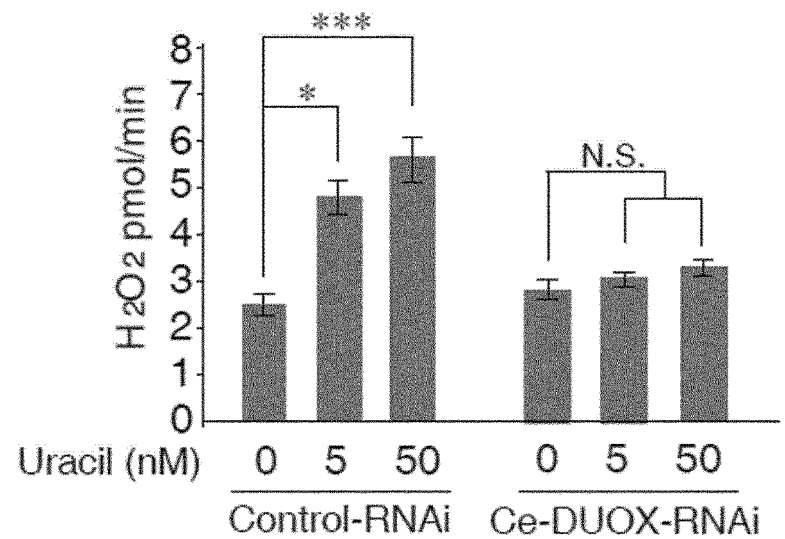

[Fig. 4h]
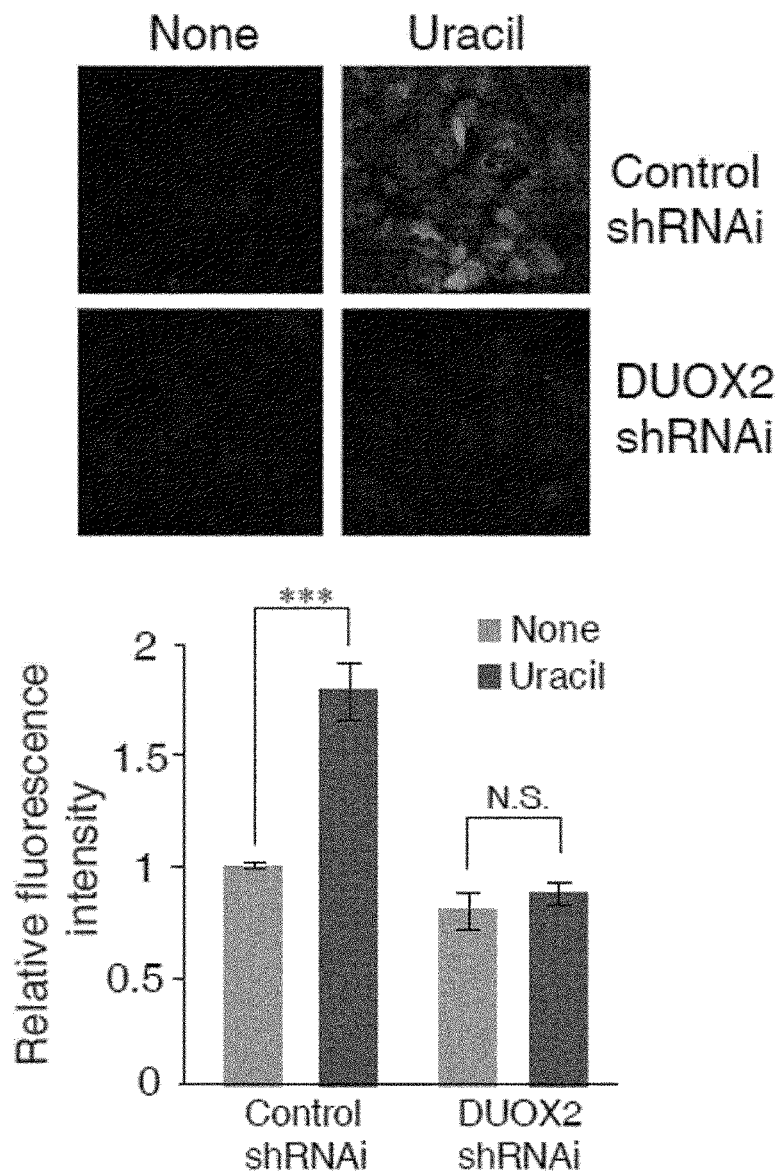

[Fig. 4i]
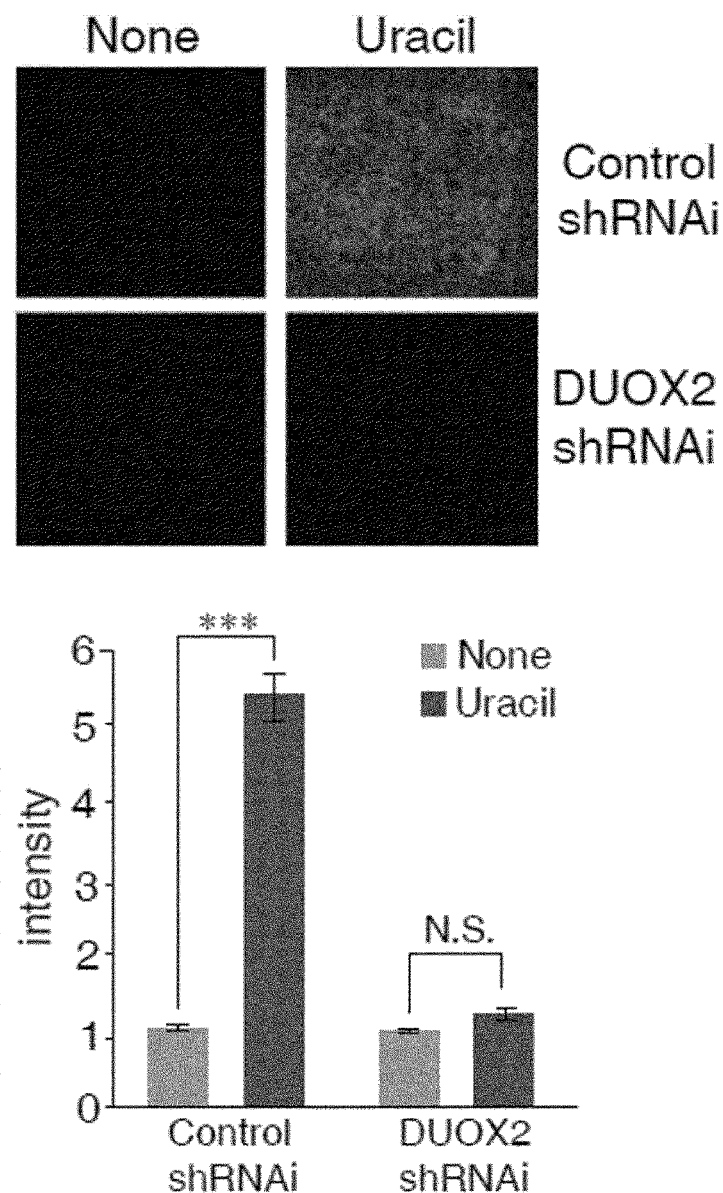

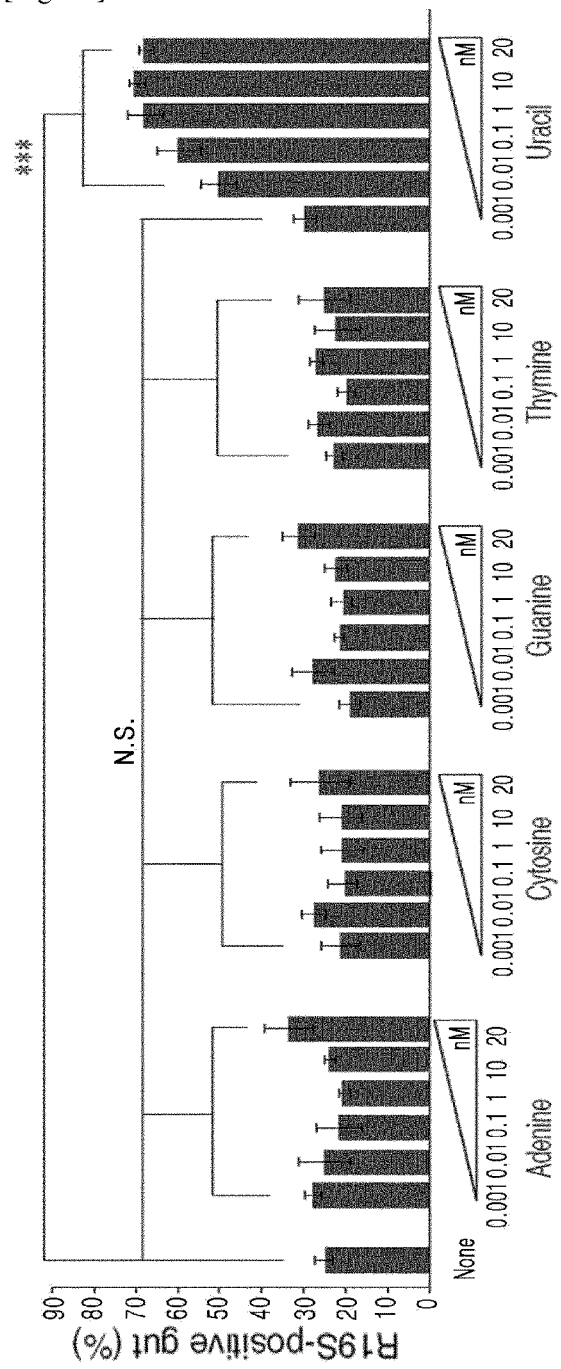
[Fig. 5a]

[Fig. 5b]
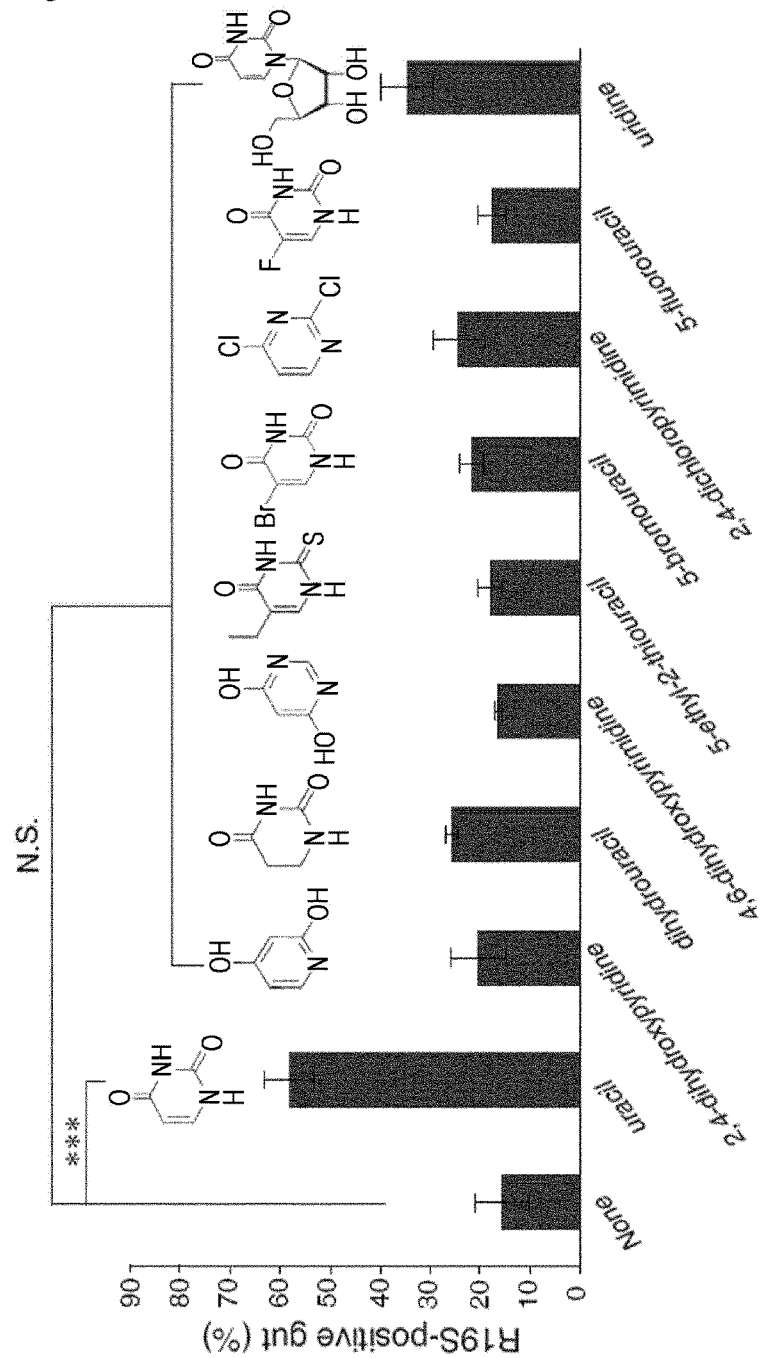

[Fig. 5c]
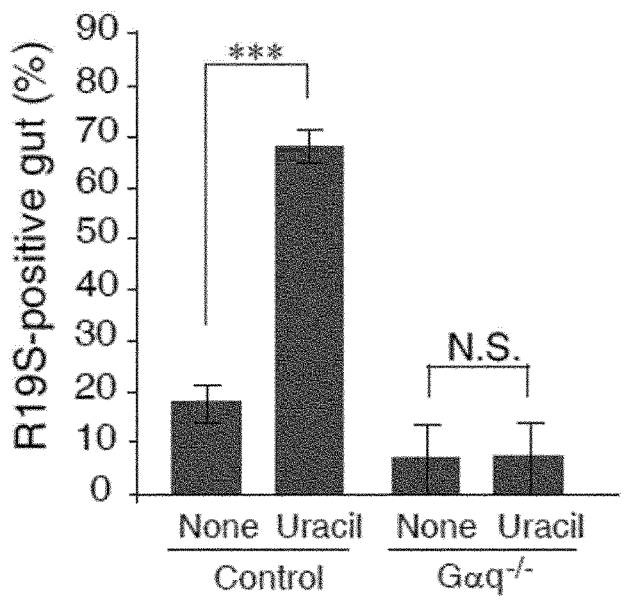
[Fig. 5d]
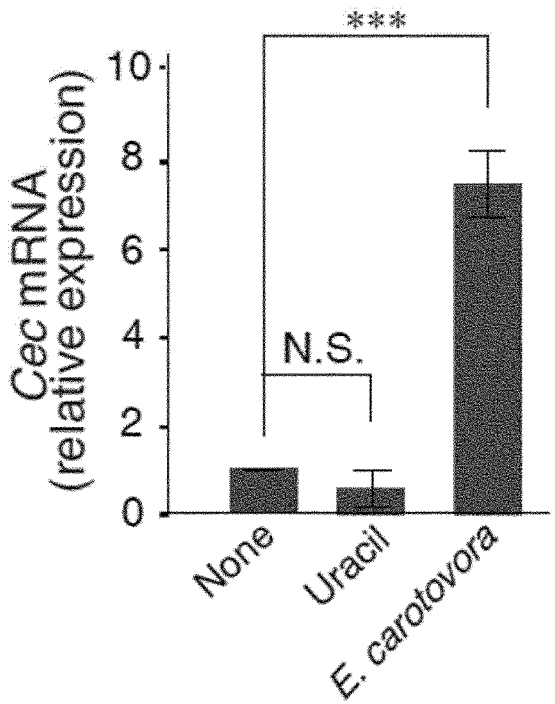

[Fig. 6a]
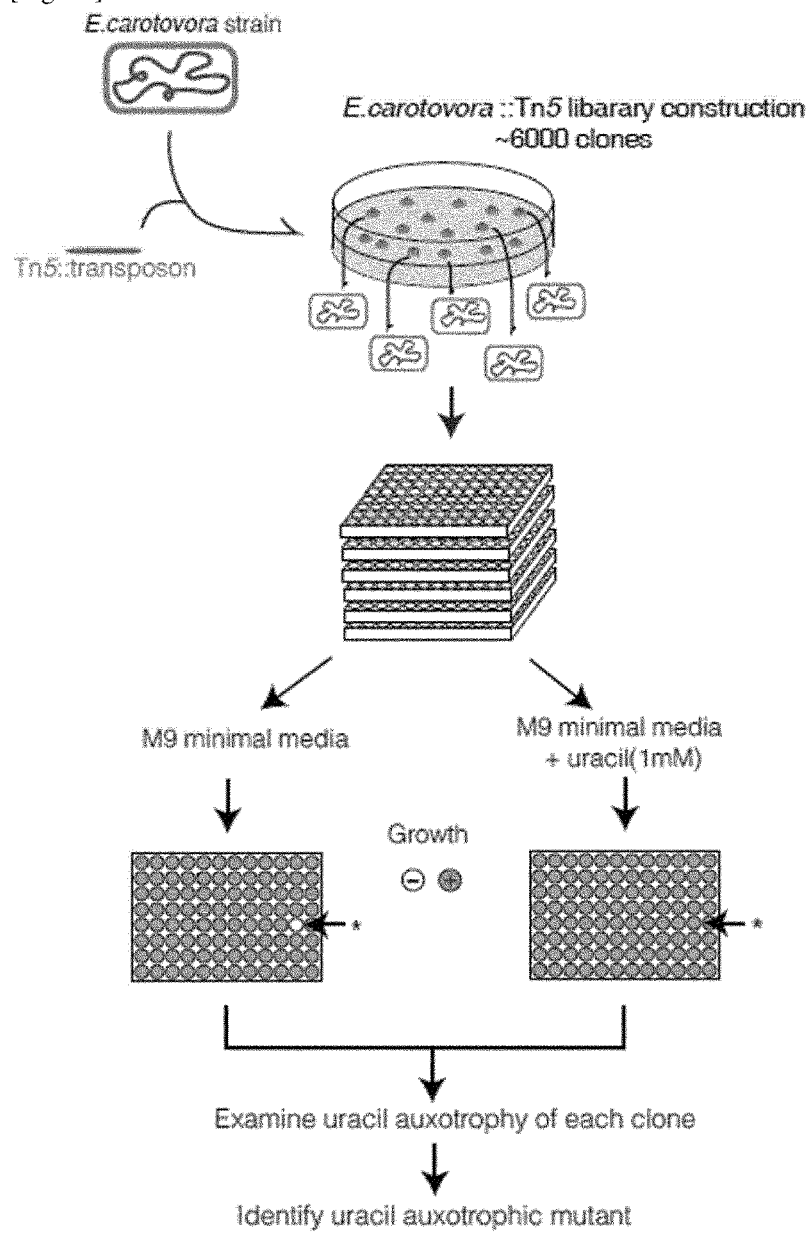
[Fig. 6b]
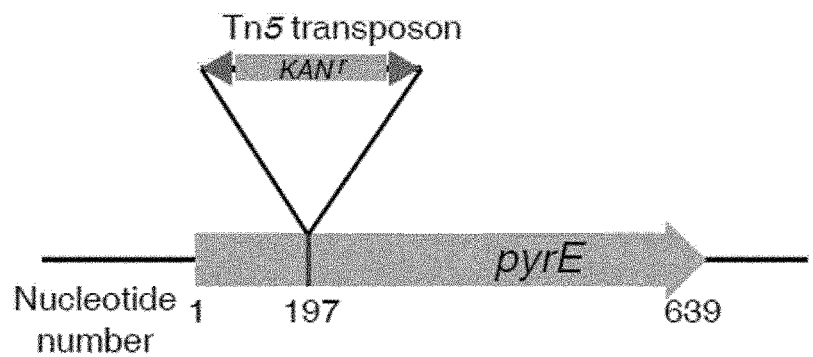

[Fig. 6c]
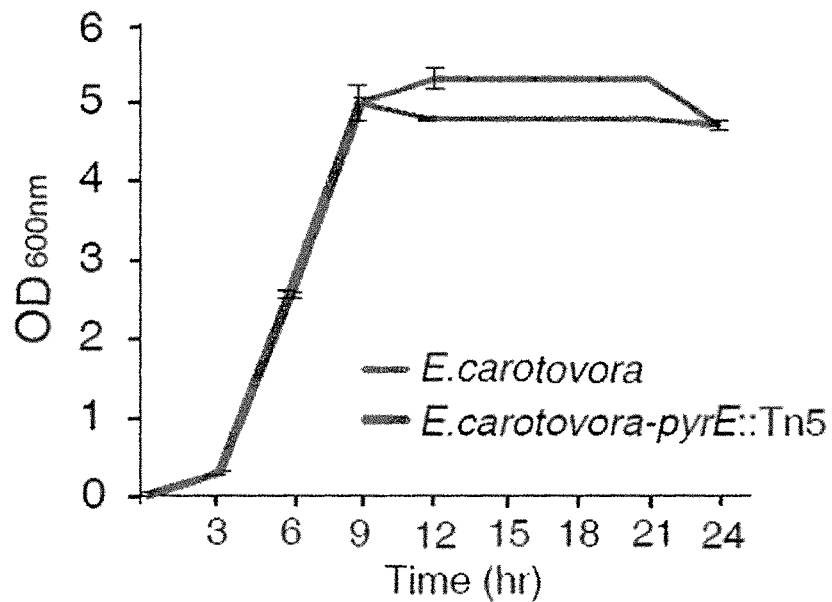
[Fig. 6d]
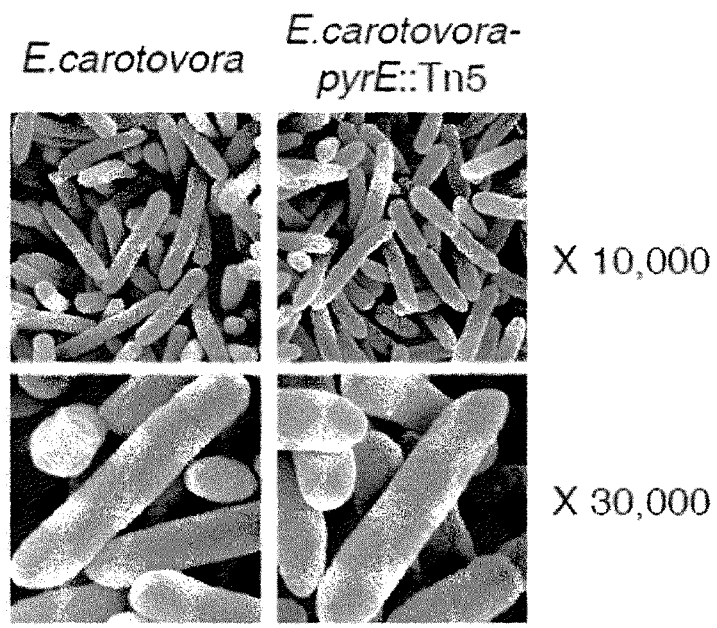

[Fig. 6e]
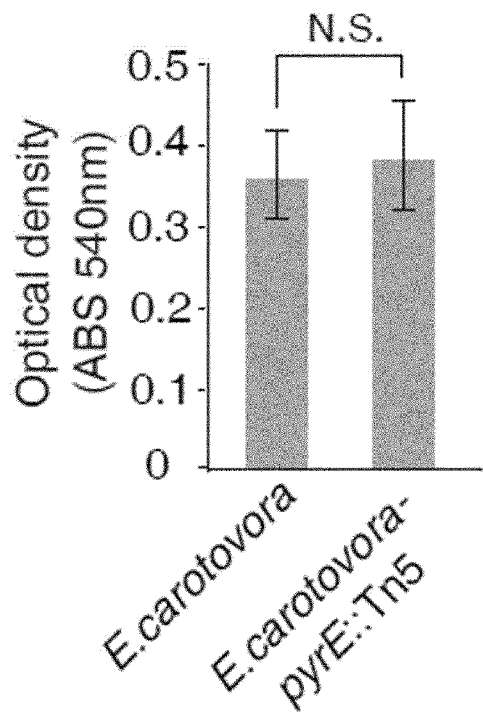
[Fig. 6f]
| Bacterial strains | MIC (μM) Cecropin A1 |
|---|---|
| E. carotovora | 5.0 |
| E. carotovora-pyrE::Tn5 | 5.0 |

[Fig. 6g]
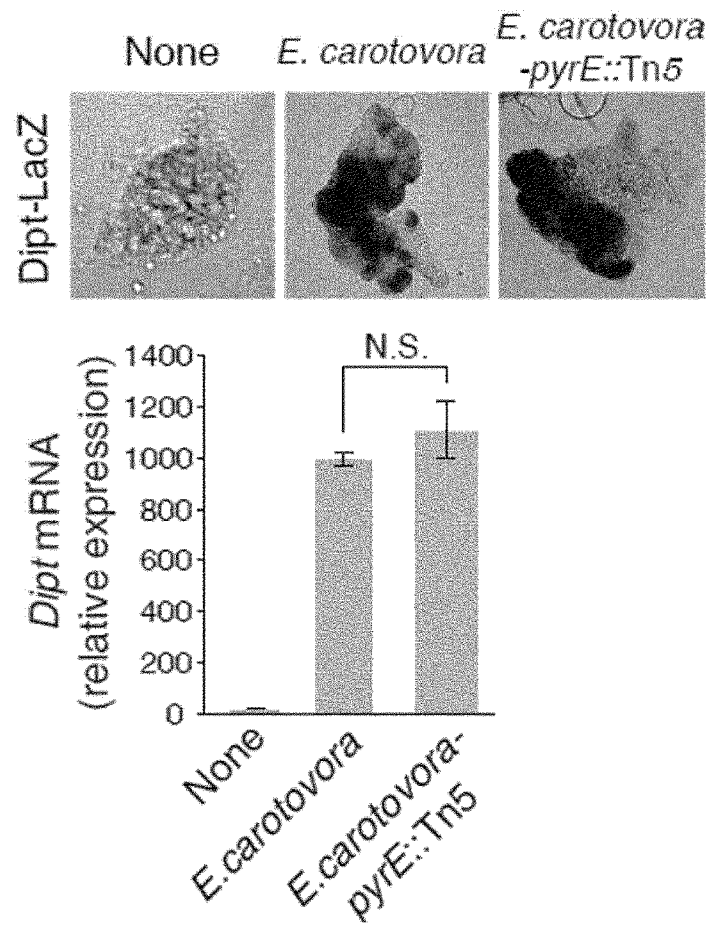
[Fig. 6h]
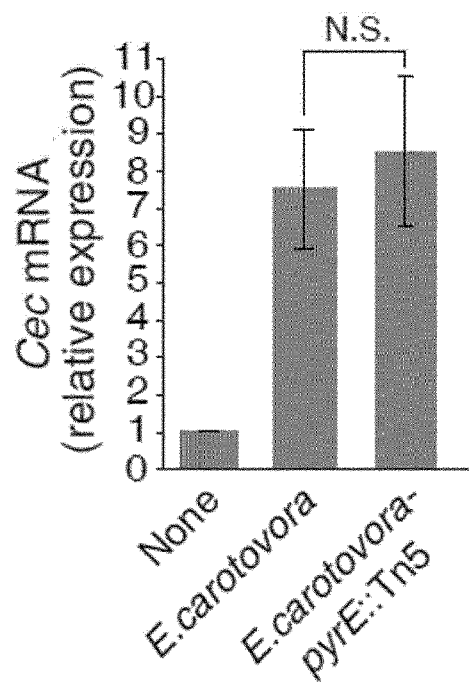

[Fig. 6i]
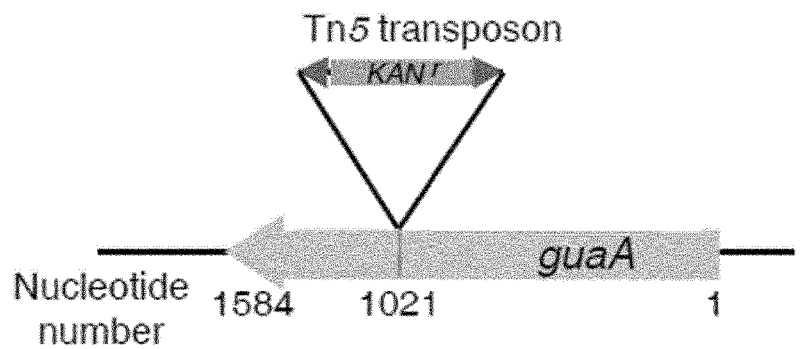
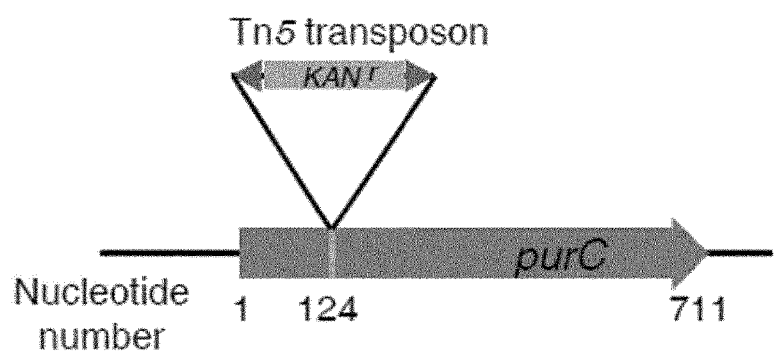
[Fig. 6j]
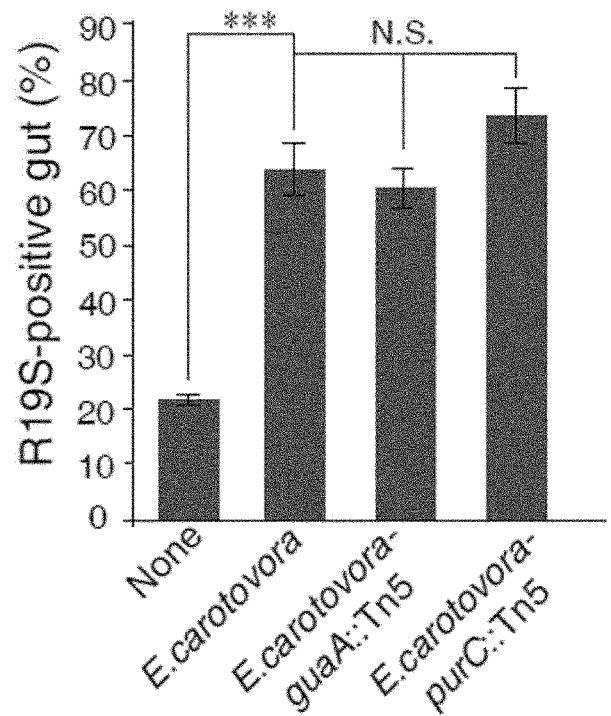

[Fig. 7a]
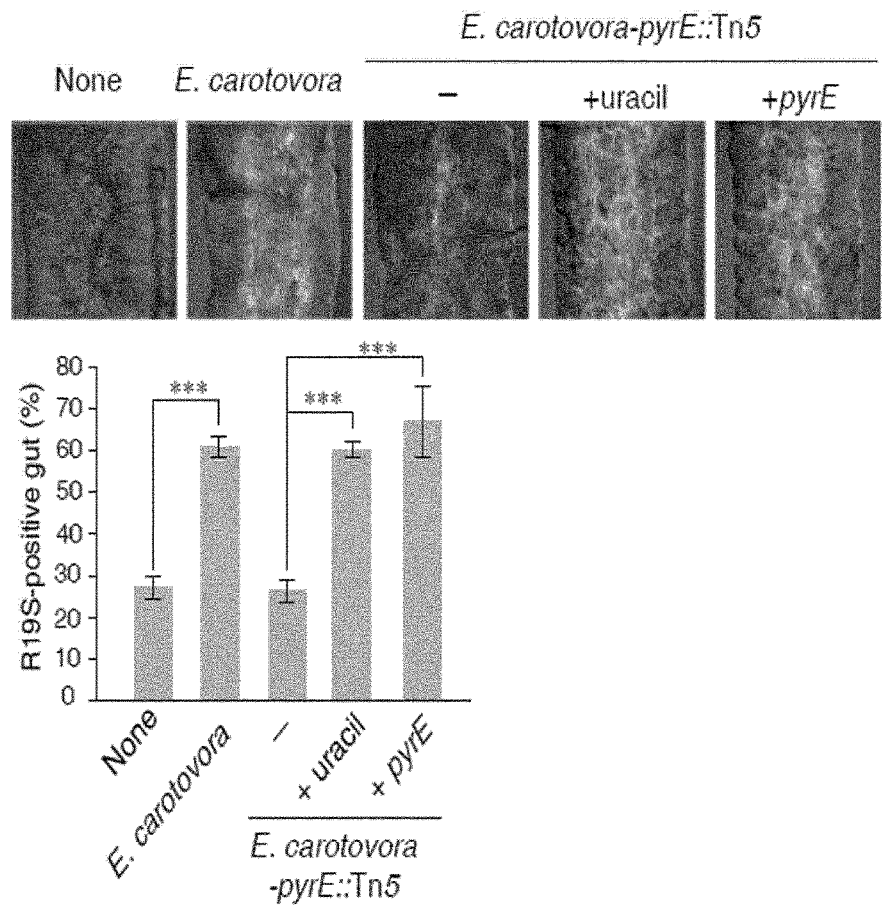

[Fig. 7b]
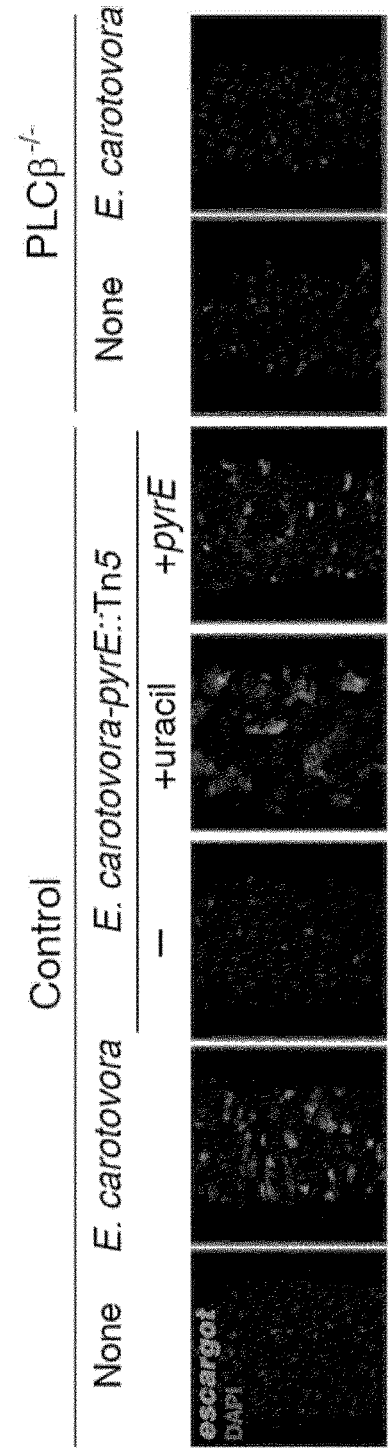

[Fig. 7c]
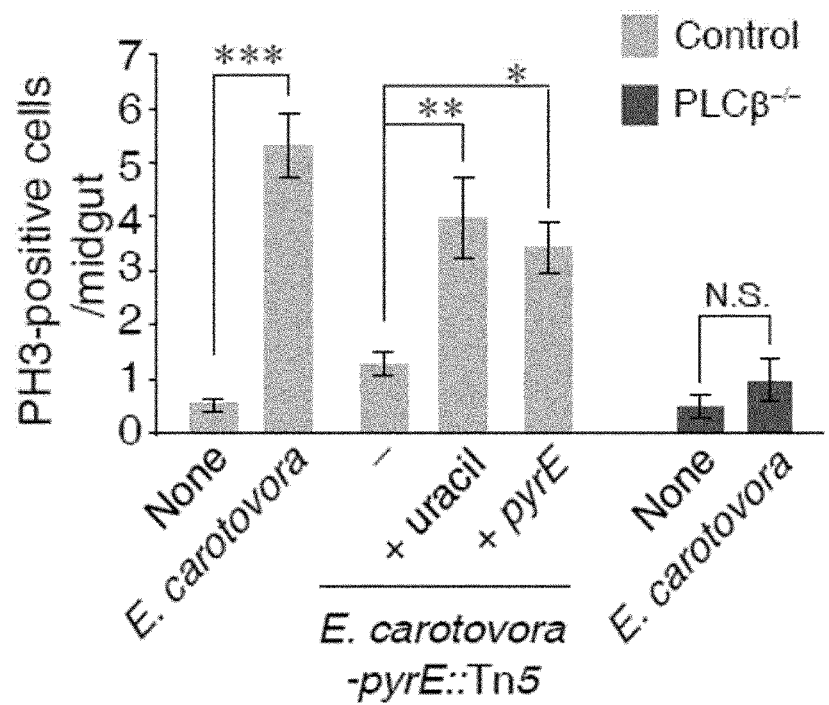

[Fig. 7d]
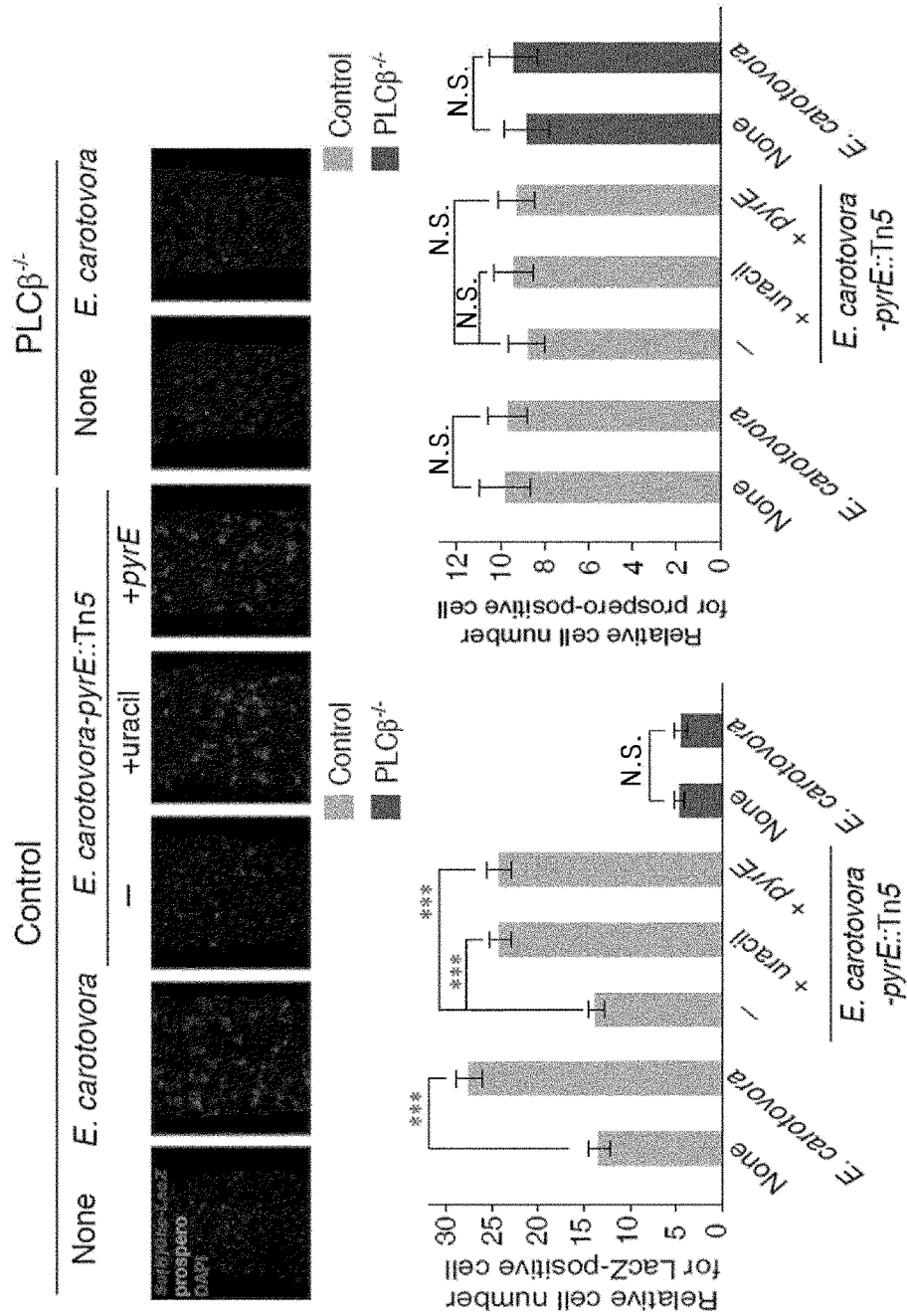

[Fig. 7e]
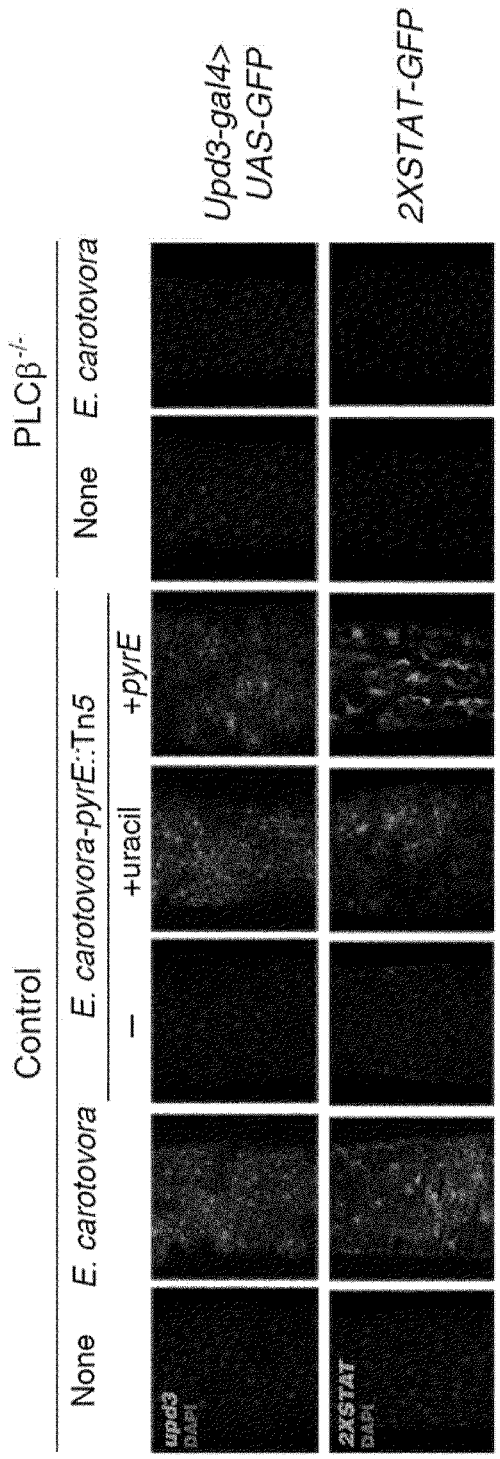

[Fig. 8a]
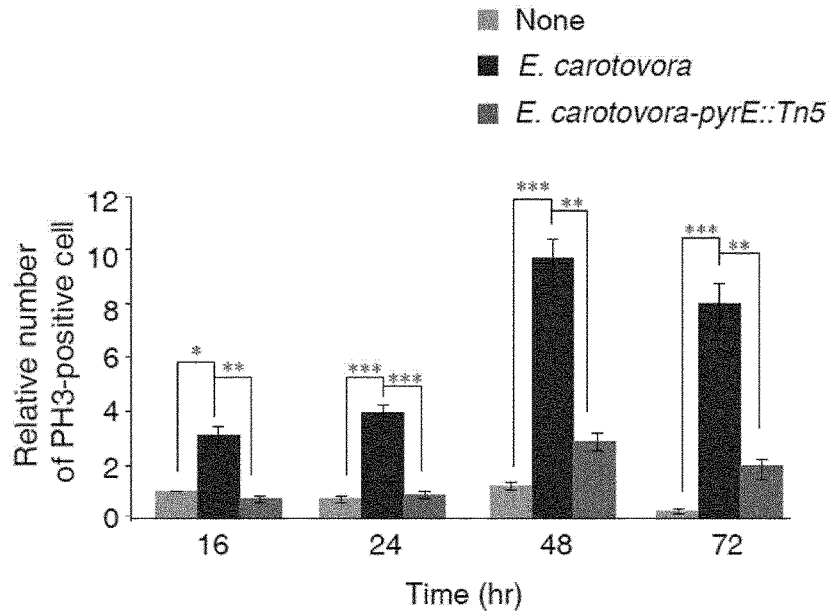
[Fig. 8b]
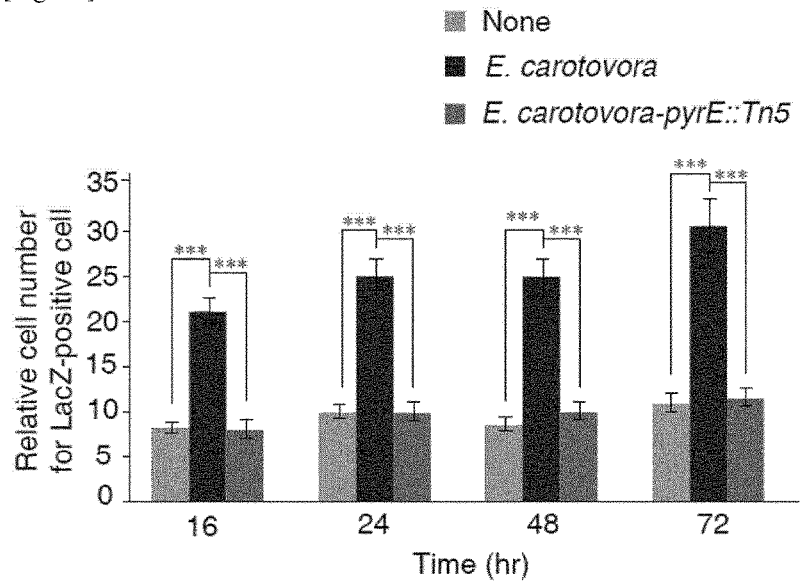

[Fig. 8c]
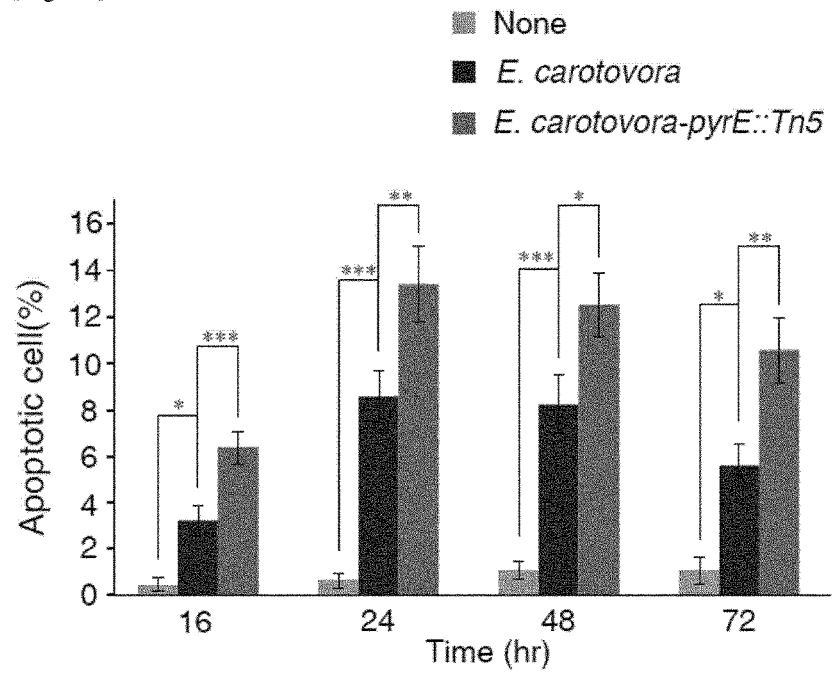
[Fig. 9a]
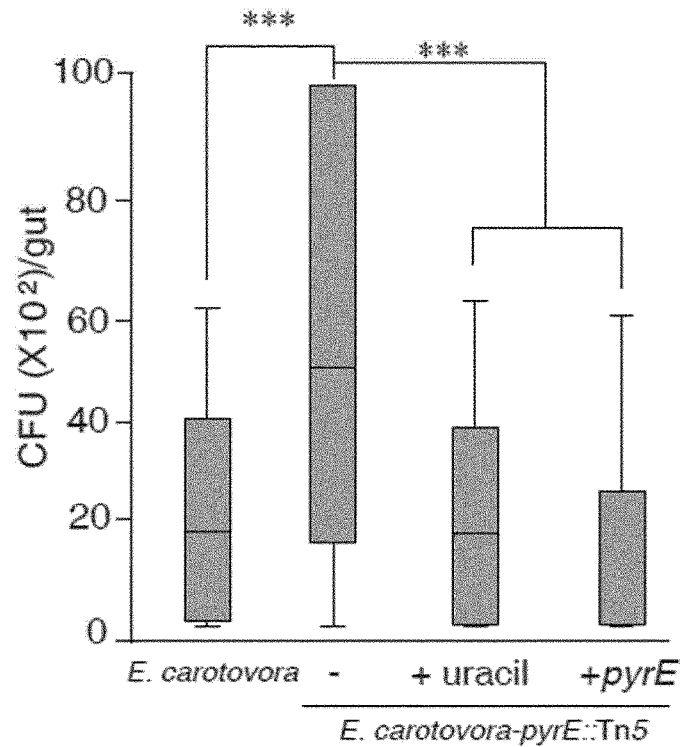

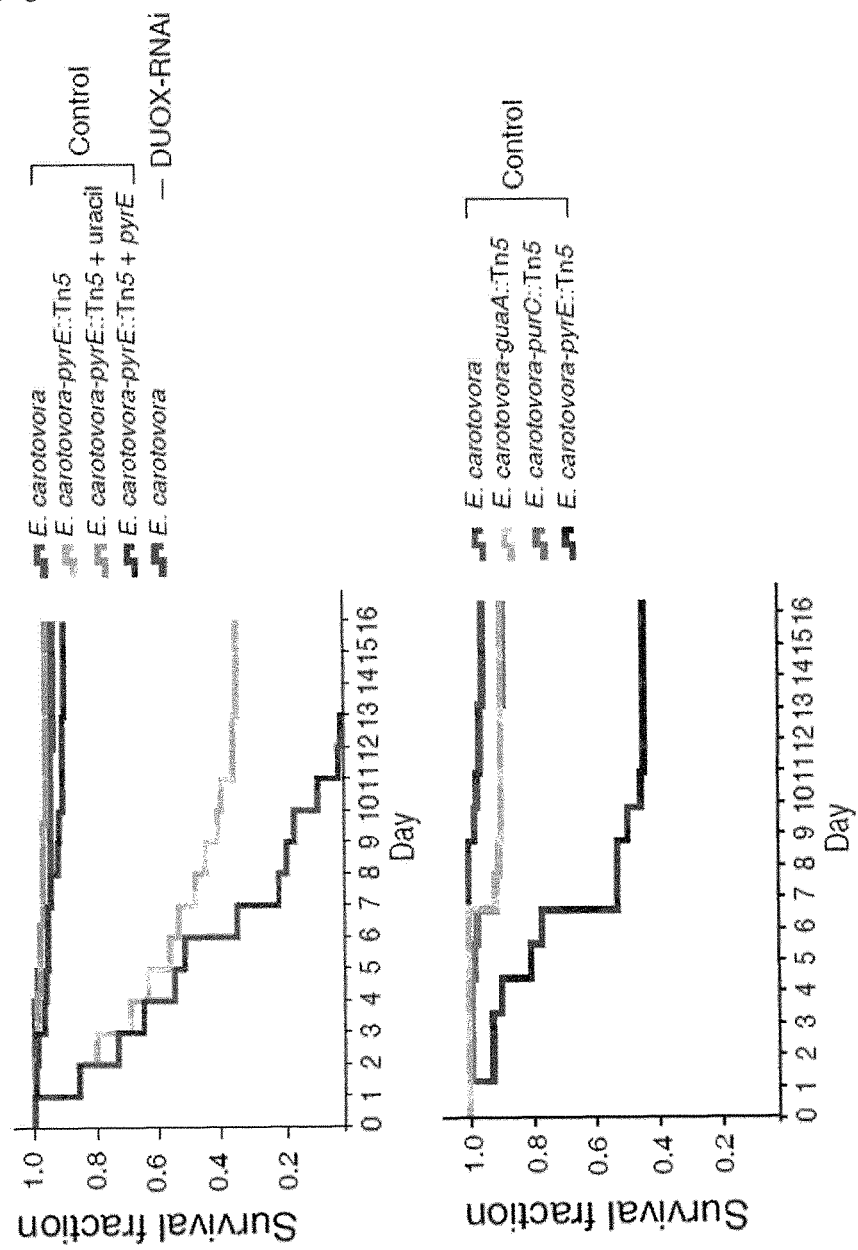
[Fig. 9b]

[Fig. 9c]
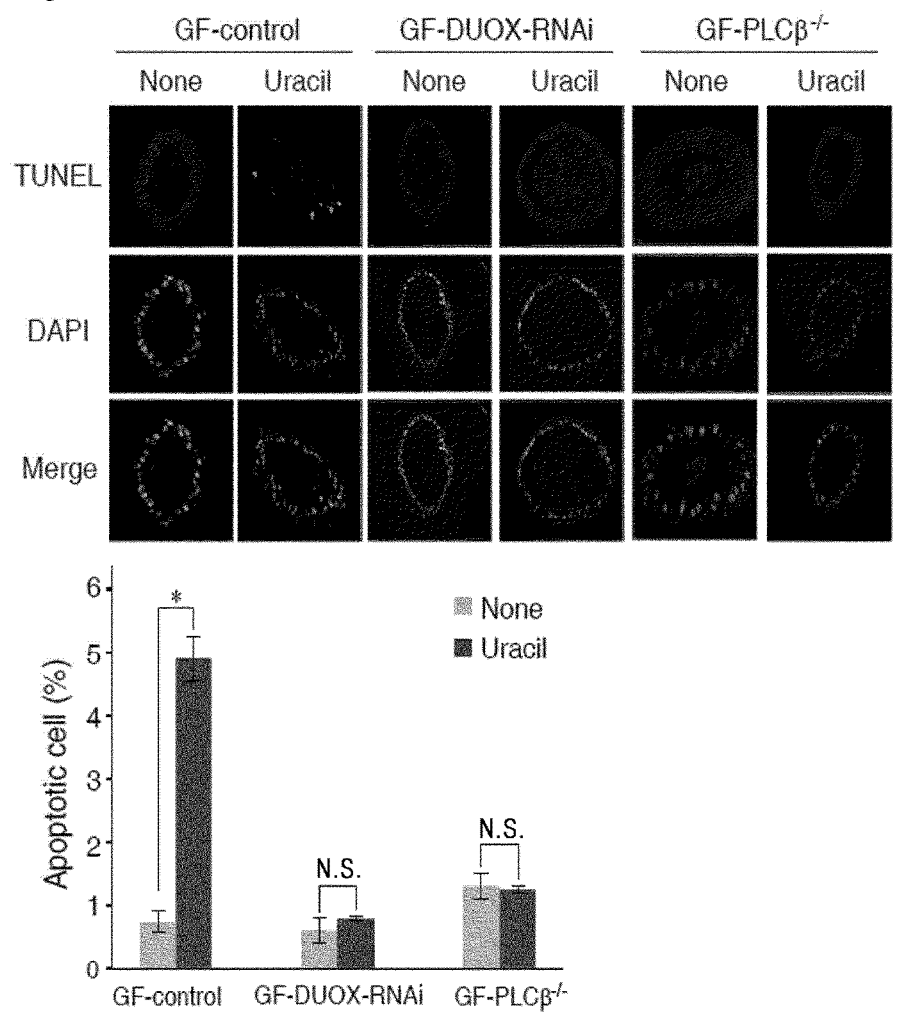

[Fig. 9d]
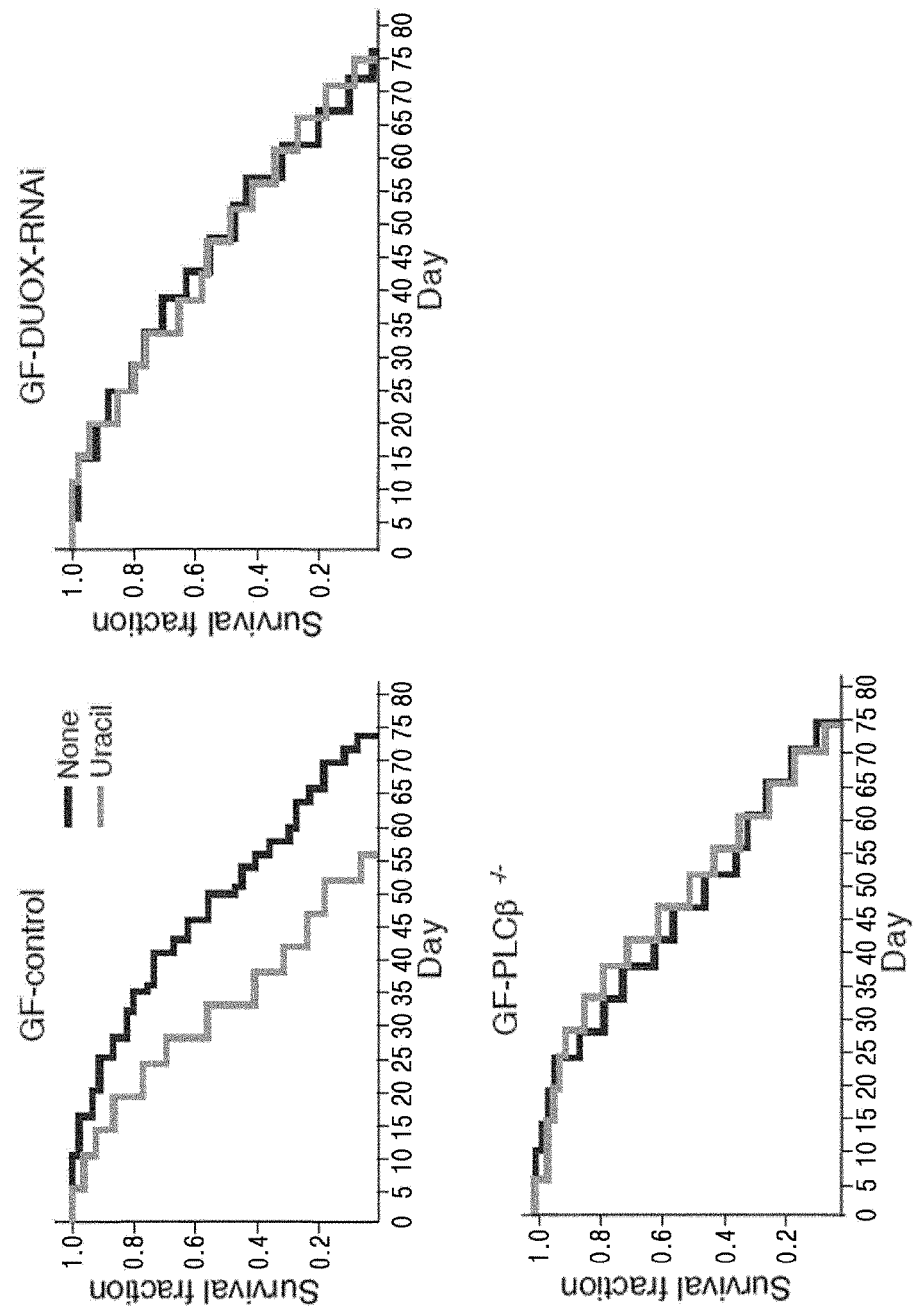

[Fig. 10a]
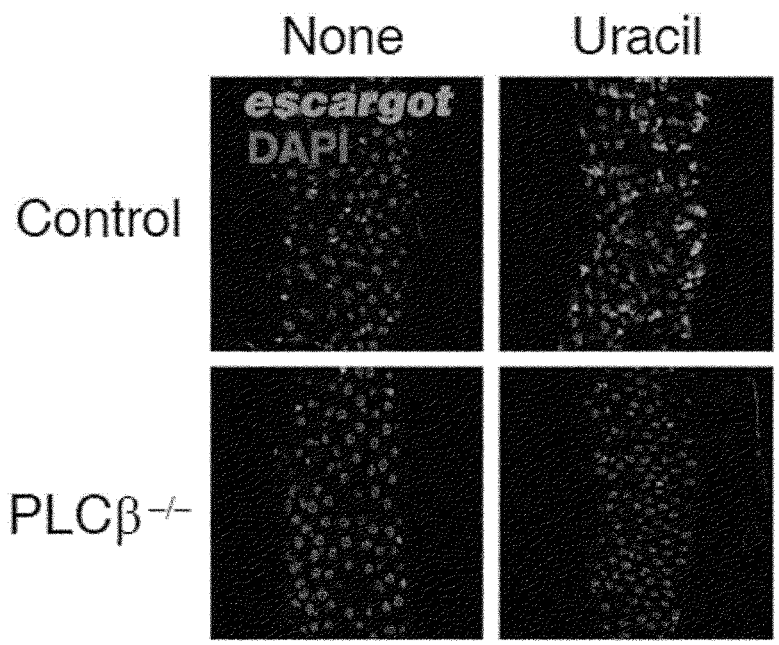
[Fig. 10b]
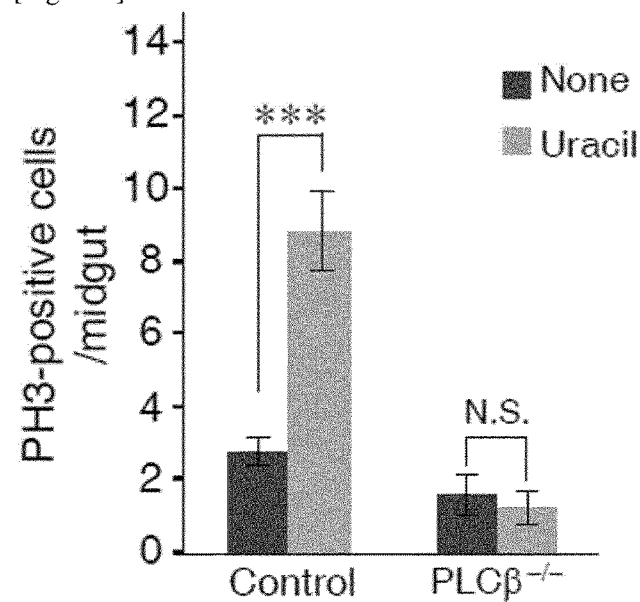

[Fig. 10c]
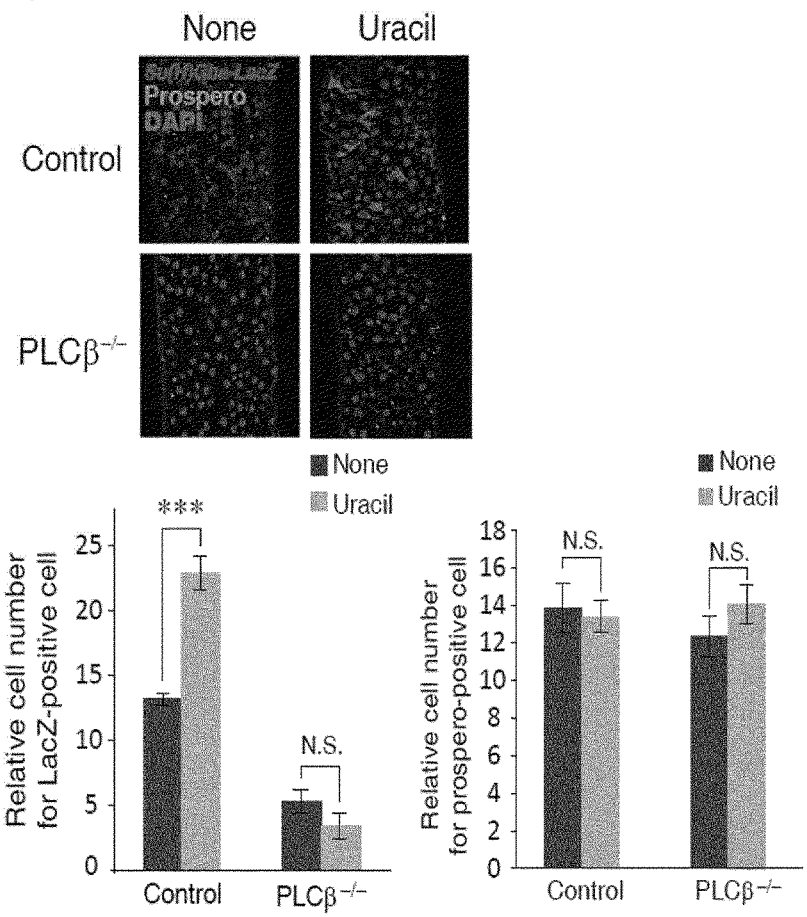
[Fig. 10d]
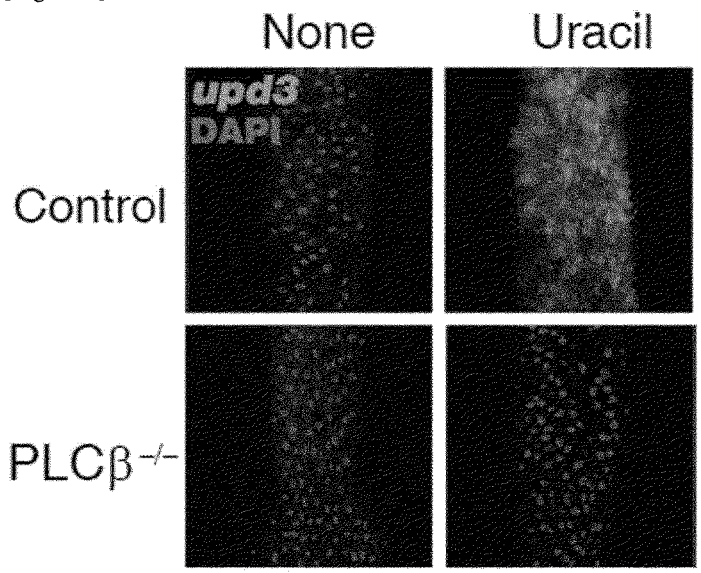

[Fig. 10e]
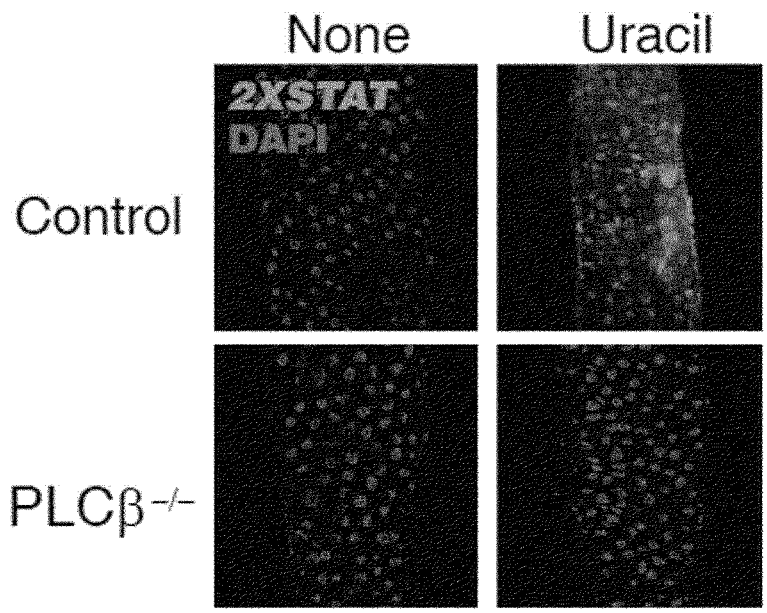
[Fig. 10f]
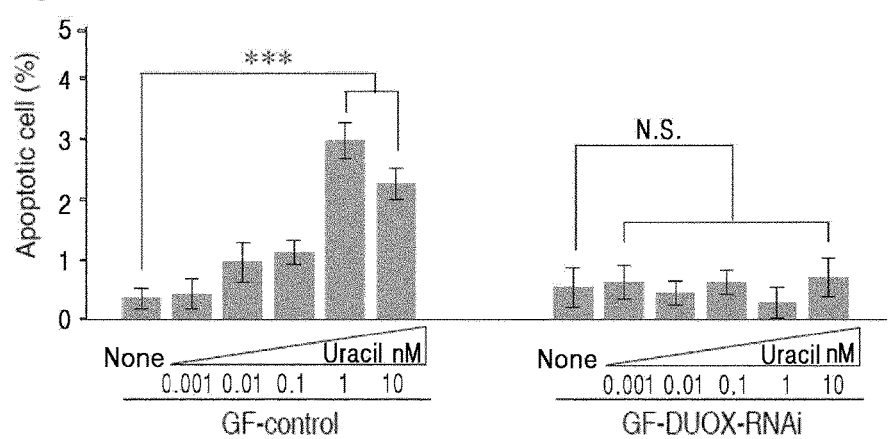

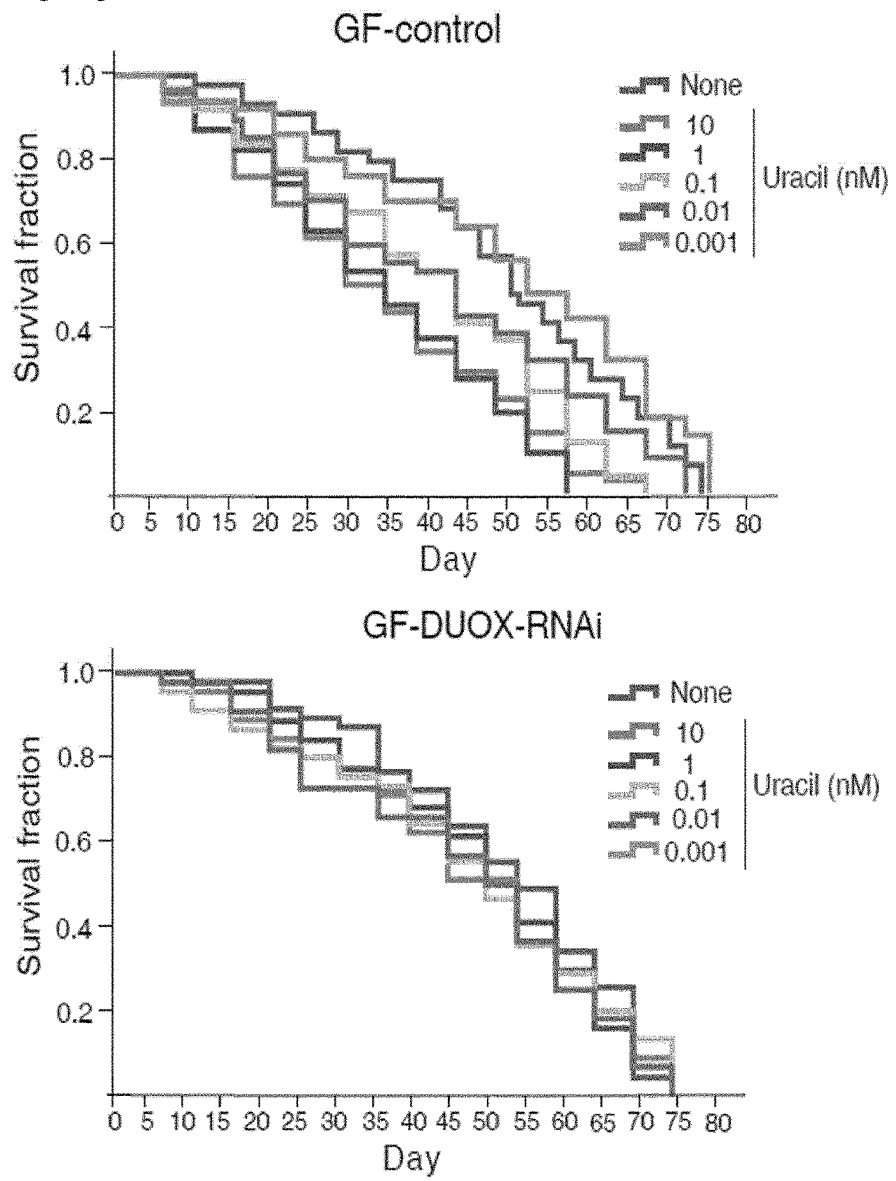
[Fig. 10g]

[Fig. 11a]
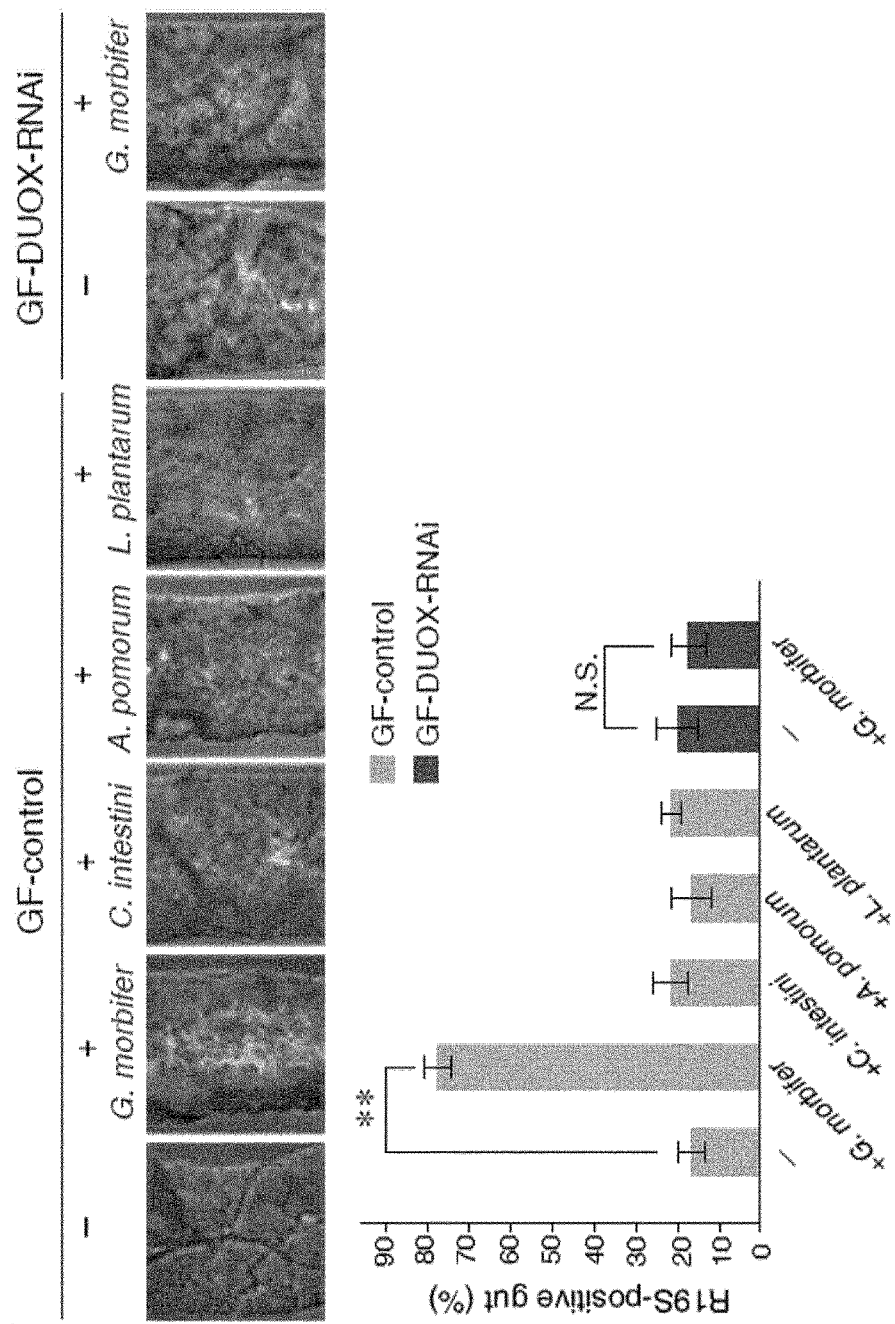

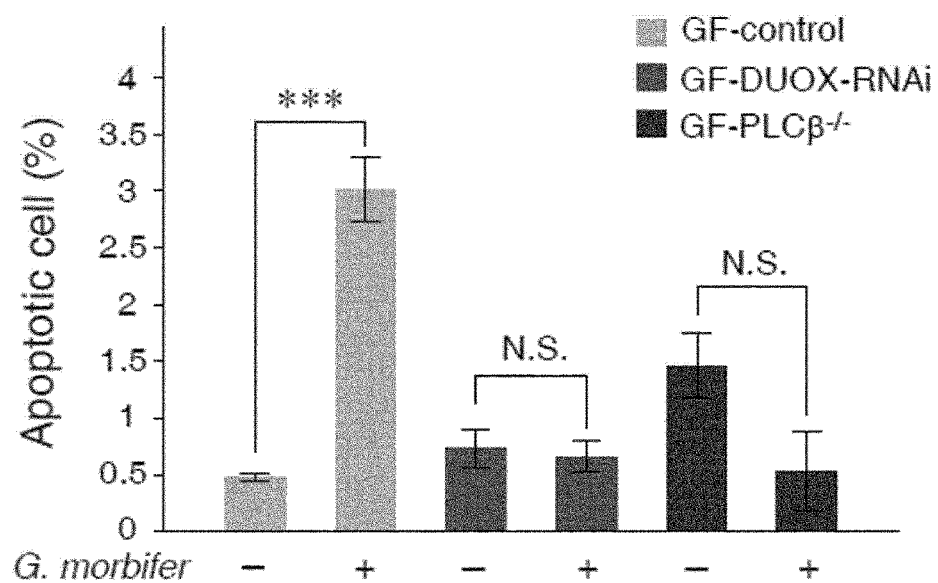
[Fig. 11b]

[Fig. 11c]
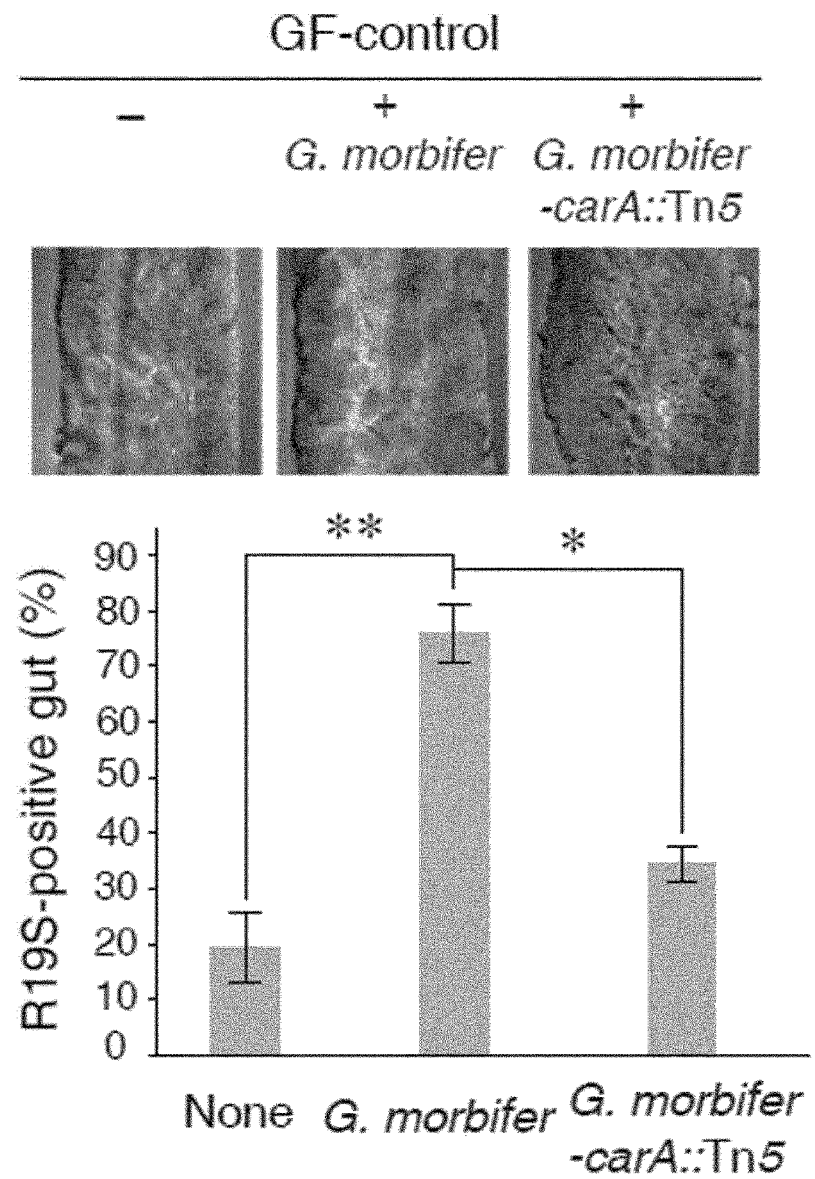

[Fig. 11d]
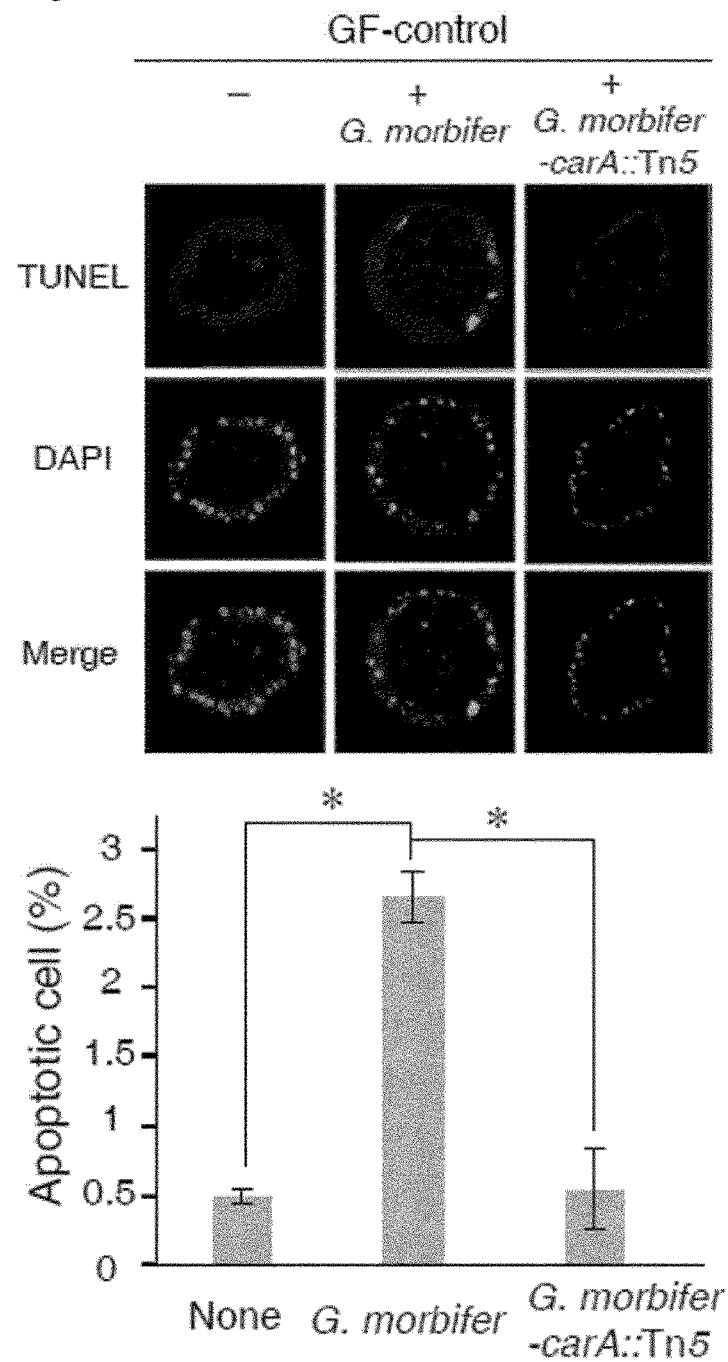

[Fig. 11e]
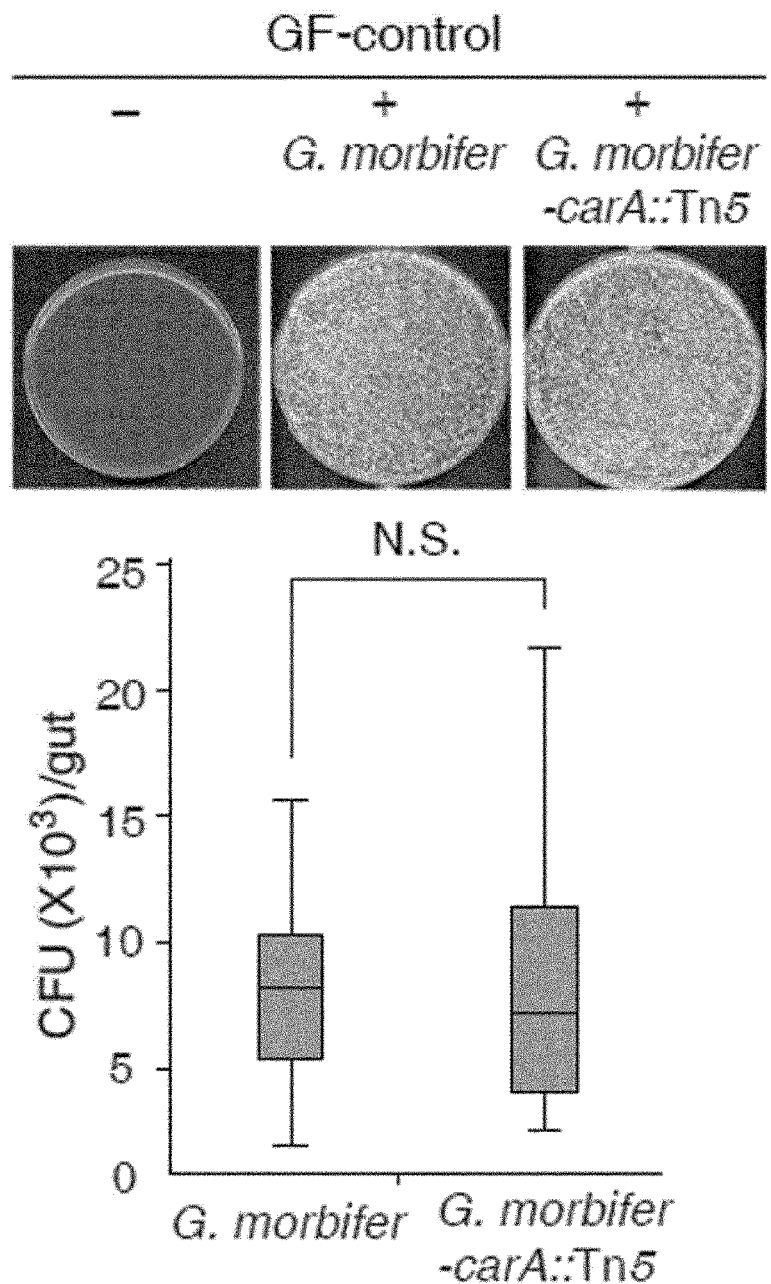

[Fig. 11f]
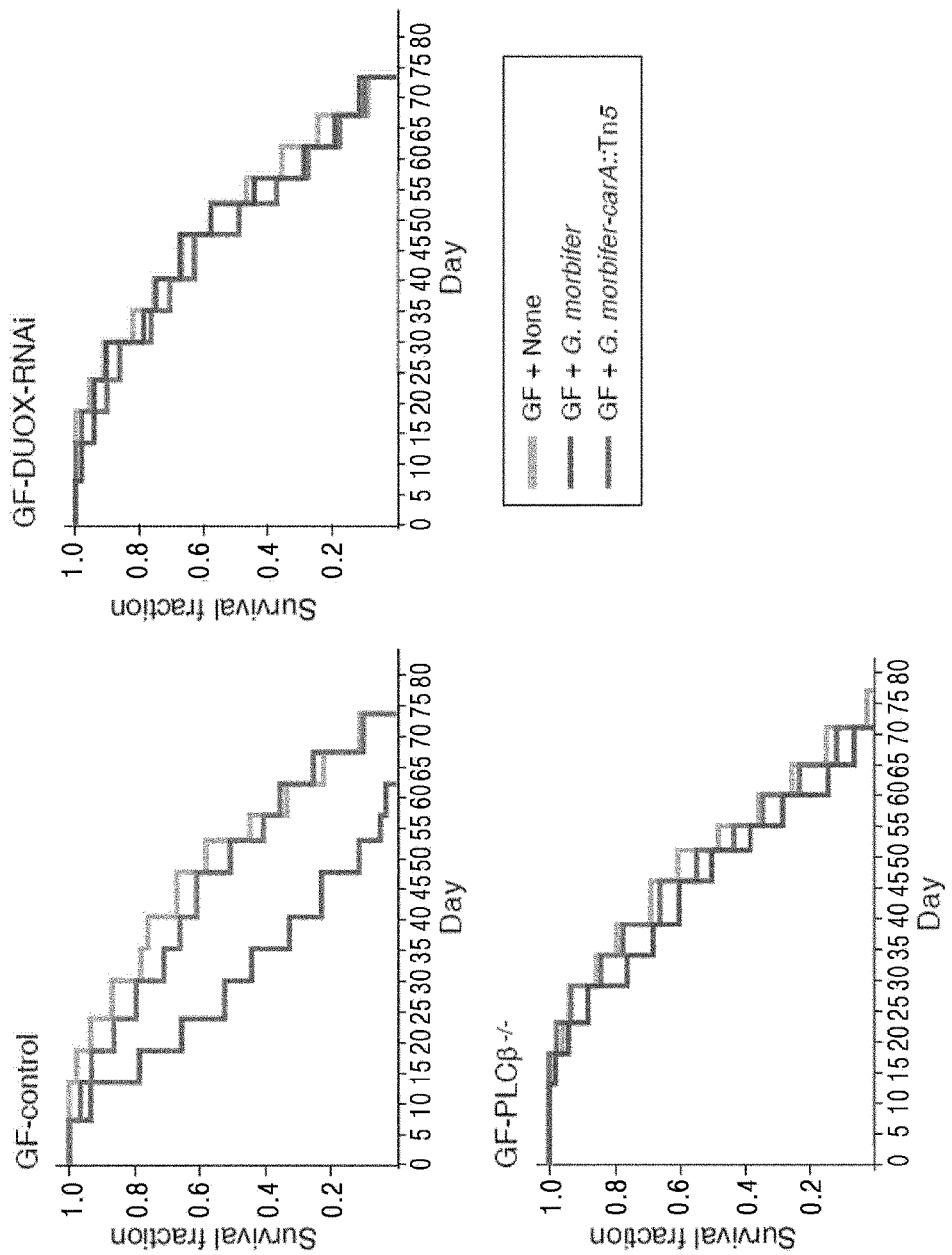

[Fig. 12a]
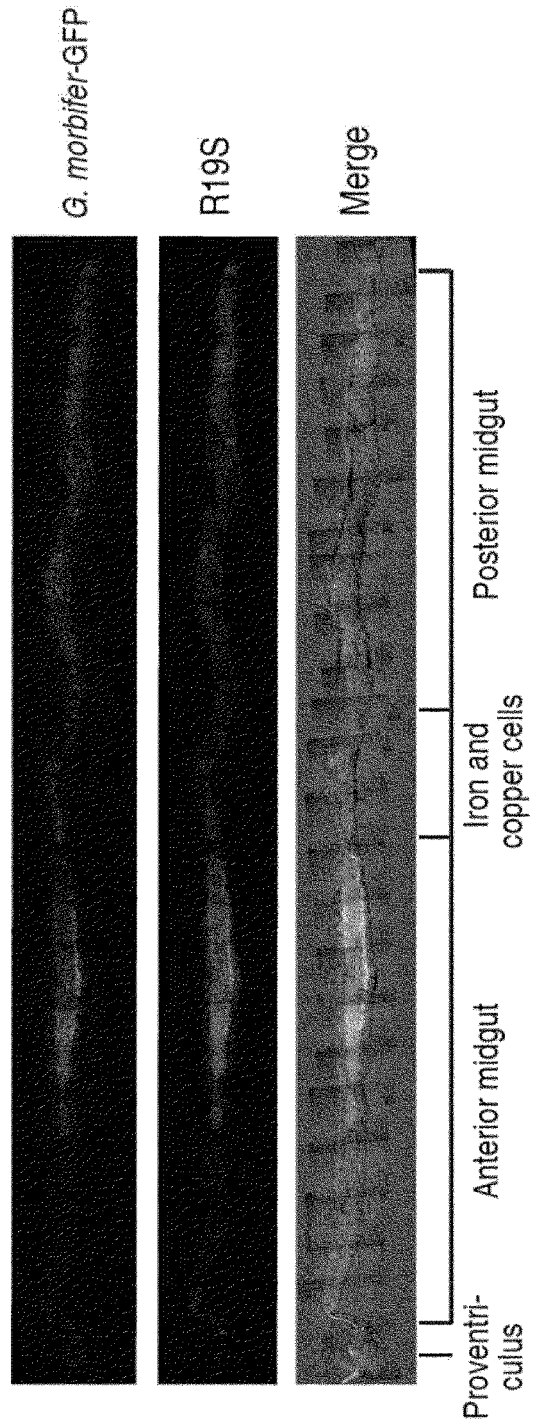

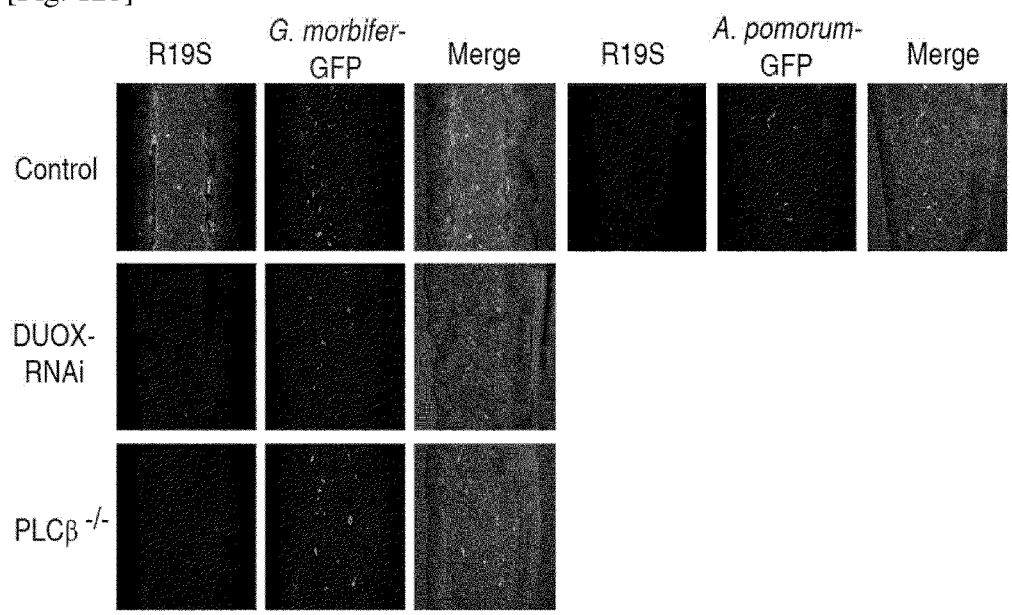
[Fig. 12b]

[Fig. 12c]
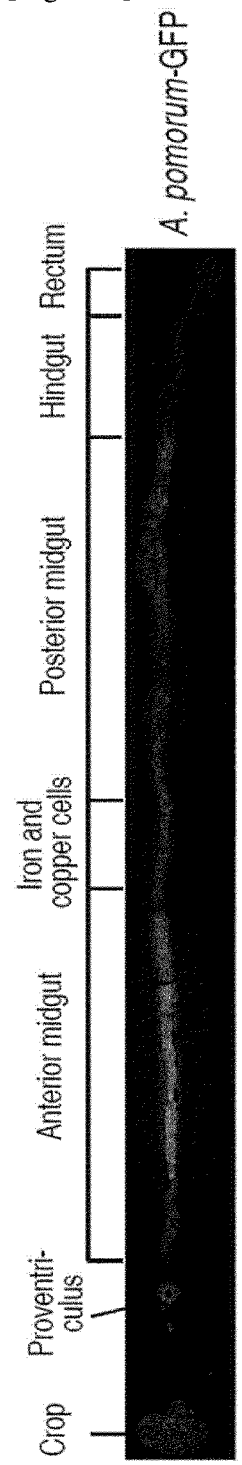

[Fig. 12d]
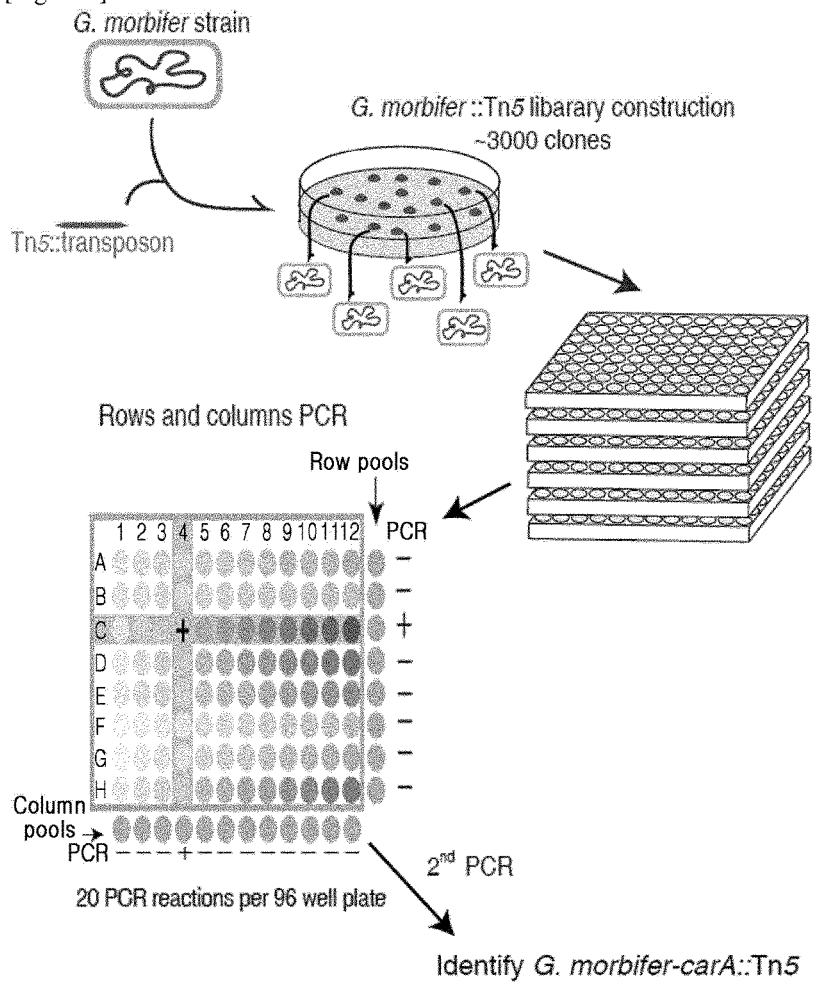
[Fig. 12e]
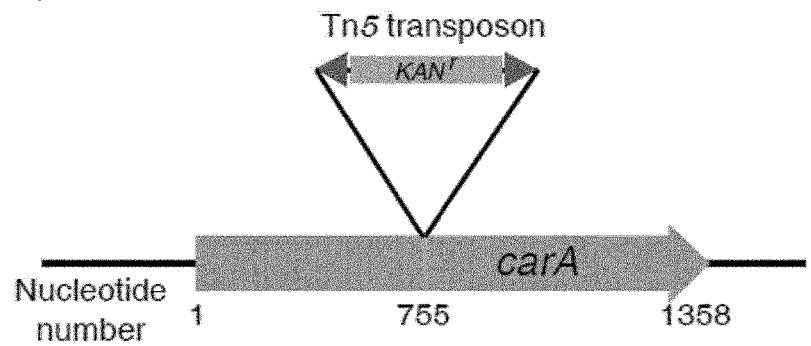

[Fig. 13a]
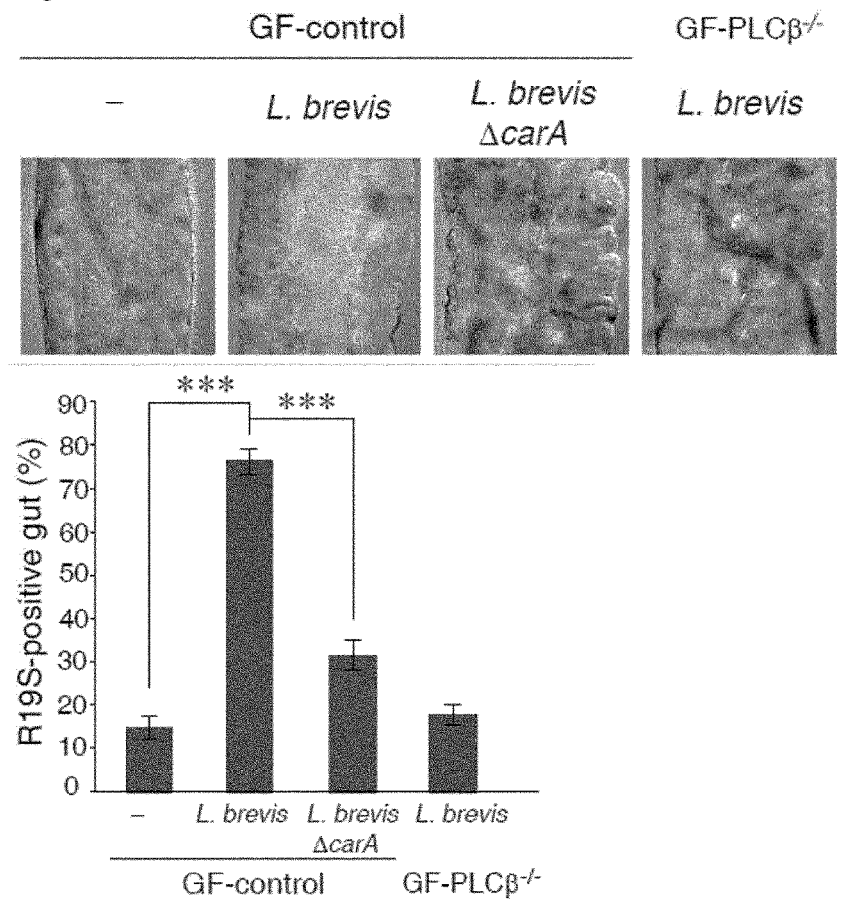
[Fig. 13b]
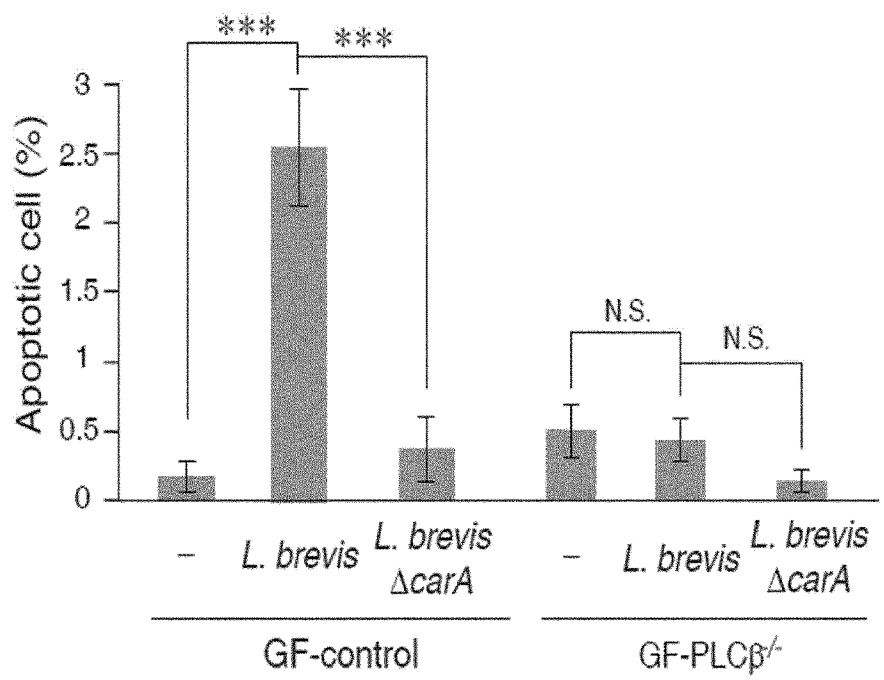

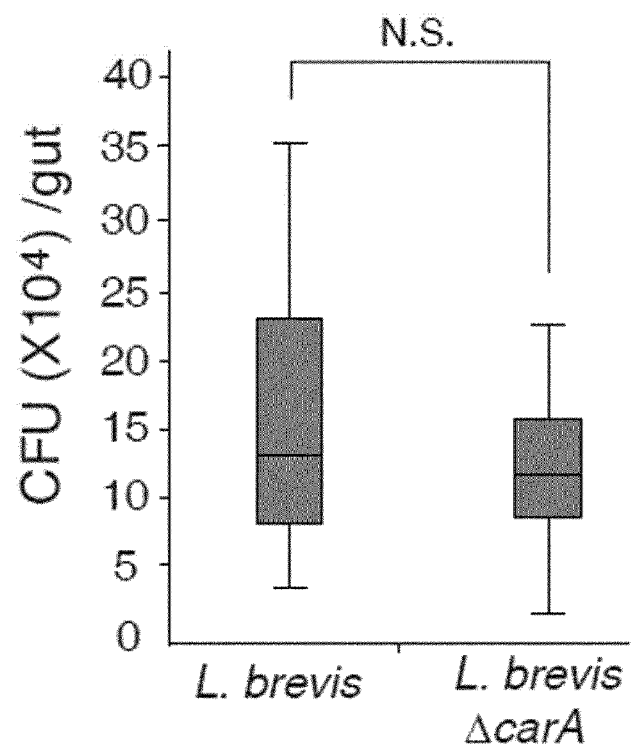
[Fig. 13c]

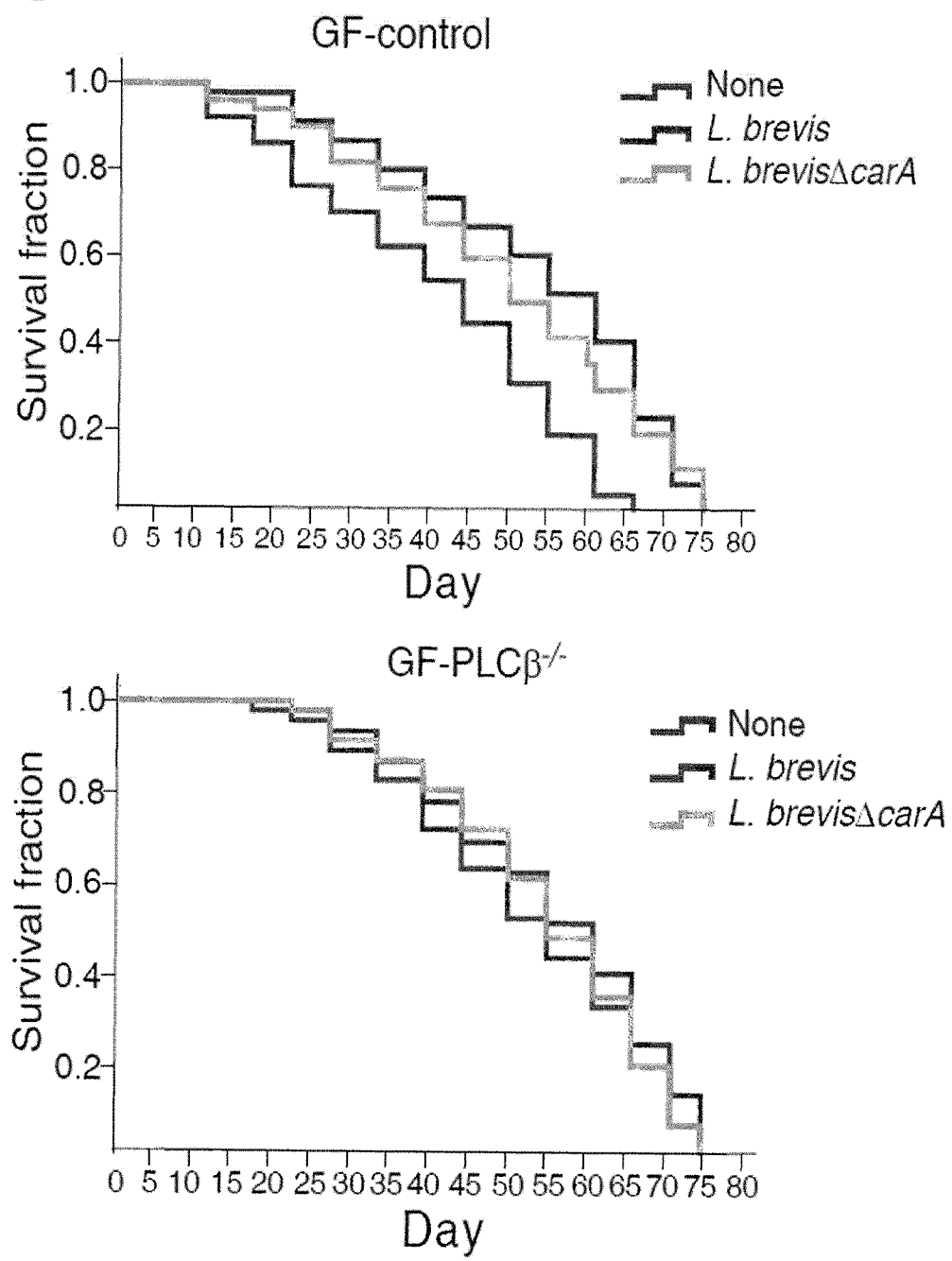
[Fig. 13d]

[Fig. 14]
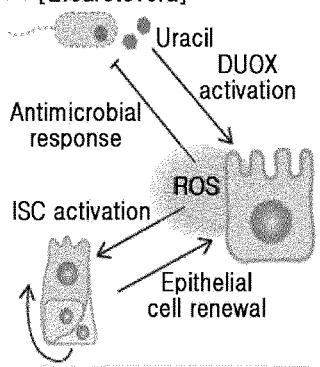

SEQUENCE LISTING

```
<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: KAN-2 forward primer

<400> SEQUENCE: 1
acctacaaca aagctctcat caacc                                          25

<210> SEQ ID NO 2
<211> LENGTH: 25
<212> TYPE: DNA
<213> ORGANISM: Artificial Sequence
<220> FEATURE:
<223> OTHER INFORMATION: KAN-2 reverse primer
```

```
<400> SEQUENCE: 2
gcaatgtaac atcagagatt ttgag                                          25

<210> SEQ ID NO 3
<211> LENGTH: 27
<212> TYPE: DNA
<213> ORGANISM: Artificial Sequence
<220> FEATURE:
<223> OTHER INFORMATION: carA forward primer

<400> SEQUENCE: 3
cggactggaa gccgtccgca aatggcg                                        27

<210> SEQ ID NO 4
<211> LENGTH: 28
<212> TYPE: DNA
<213> ORGANISM: Artificial Sequence
<220> FEATURE:
<223> OTHER INFORMATION: carA reverse primer

<400> SEQUENCE: 4
cgaaacgctc gaaagatag aaactgtc                                        28

<210> SEQ ID NO 5
<211> LENGTH: 22
<212> TYPE: DNA
<213> ORGANISM: Artificial Sequence
<220> FEATURE:
<223> OTHER INFORMATION: Cecropin sense primer

<400> SEQUENCE: 5
atgaacttct acaacatctt cg                                             22

<210> SEQ ID NO 6
<211> LENGTH: 22
<212> TYPE: DNA
<213> ORGANISM: Artificial Sequence
<220> FEATURE:
<223> OTHER INFORMATION: Cecropin antisense primer

<400> SEQUENCE: 6
ggcagttgcg gcgacattgg cg                                             22

<210> SEQ ID NO 7
<211> LENGTH: 20
<212> TYPE: DNA
<213> ORGANISM: Artificial Sequence
<220> FEATURE:
<223> OTHER INFORMATION: Diptericin sense primer

<400> SEQUENCE: 7
ggcttatccg atgcccgacg                                                20

<210> SEQ ID NO 8
<211> LENGTH: 22
<212> TYPE: DNA
<213> ORGANISM: Artificial Sequence
<220> FEATURE:
<223> OTHER INFORMATION: Diptericin antisense primer

<400> SEQUENCE: 8
tctgtaggtg taggtgcttc cc                                             22
```

```
<210> SEQ ID NO 9
<211> LENGTH: 24
<212> TYPE: DNA
<213> ORGANISM: Artificial Sequence
<220> FEATURE:
<223> OTHER INFORMATION: DUOX sense primer

<400> SEQUENCE: 9
gctgcacgcc aaccacaaga gact                                          24

<210> SEQ ID NO 10
<211> LENGTH: 24
<212> TYPE: DNA
<213> ORGANISM: Artificial Sequence
<220> FEATURE:
<223> OTHER INFORMATION: DUOX antisense primer

<400> SEQUENCE: 10
cacgcgcagc aggatgtaag gttt                                          24

<210> SEQ ID NO 11
<211> LENGTH: 23
<212> TYPE: DNA
<213> ORGANISM: Artificial Sequence
<220> FEATURE:
<223> OTHER INFORMATION: Rp49 sense primer

<400> SEQUENCE: 11
agatcgtgaa gaagcgcacc aag                                           23

<210> SEQ ID NO 12
<211> LENGTH: 23
<212> TYPE: DNA
<213> ORGANISM: Artificial Sequence
<220> FEATURE:
<223> OTHER INFORMATION: Rp49 antisense primer

<400> SEQUENCE: 12
caccaggaac ttcttgaatc cgg                                           23

<210> SEQ ID NO 13
<211> LENGTH: 61
<212> TYPE: DNA
<213> ORGANISM: Artificial Sequence
<220> FEATURE:
<223> OTHER INFORMATION: DUOX2 shRNA

<400> SEQUENCE: 13
gccatcagga gtggcataaa ttagtgaagc cacagatgta atttatgcca ctcctgatgg   60
c                                                                   61

<210> SEQ ID NO 14
<211> LENGTH: 48
<212> TYPE: DNA
<213> ORGANISM: Artificial Sequence
<220> FEATURE:
<223> OTHER INFORMATION: pLZRS shRNA

<400> SEQUENCE: 14
caacaagatg aagagcacca actcgagttg gtgctcttca tcttgttg                48
```

COMPOSITION FOR CONTROLLING A GUT IMMUNITY AND USE THEREOF

CROSS-REFERENCE TO RELATED APPLICATIONS

This application is a national phase application under 35 U.S.C. § 371 of International Patent Application No. PCT/KR2014/004072, filed May 8, 2014, which claims the benefit of priority to Korean Patent Application No. 10-2013-0052133, filed May 8, 2013. The entire contents of the referenced applications are incorporated herein by reference.

TECHNICAL FIELD

The present invention relates to an antimicrobial composition for uracil non-secretory (URA−) bacteria comprising uracil, uracil precursors, uracil analogs, or uracil-secreting opportunistic pathogens as an active ingredient; and a composition for preventing cell damage caused by uracil-secretory (URA+) bacteria, comprising ROS scavengers as an active ingredient. The present invention also relates to food or feed for antimicrobial activity and preventing cell damage, comprising said composition; a method for controlling dual oxidase (DUOX) activation, the generation of reactive oxygen species (ROS), or the level thereof; a method for producing cells, wherein DUOX activation, the generation of ROS, or the level thereof are controlled; and a method for providing information on gut pathogenicity in isolated bacteria.

BACKGROUND ART

The gut epithelia of most metazoan organisms encompass complex microbial communities that range from autochthonous bacteria to allochthonous bacteria. Autochthonous bacteria have evolutionarily adapted to the host gut environment and are capable of colonizing the gut by permanent attachment thereto, whereas allochthonous bacteria are introduced from external environments and transiently interact with gut epithelia by passing through the alimentary flowing stream. Therefore, in response to various and continuous influx of microbes, host microbes have evolved to modulate the gut immunity to achieve gut-microbe homeostasis.

As such, all metazoan guts possess immunologically unique environments. Specifically, these environments enable the commensal microbes among various microbes derived from external environments to have a symbiosis while having an efficient antimicrobial system for eliminating pathogens. However, this is a paradoxical situation from the classical view point of innate immunity because host immune cells should be able to mount an antimicrobial response against any microbes, regardless of whether it is commensal or pathogenic, by sensing universal microbe-associated molecular patterns (MAMPs).

Several models have been proposed to explain this paradoxical situation. These models include restricted expression and compartmentalization of pattern recognition receptors (PRRs), multiple mechanisms to down-regulate NF-kappaB-dependent innate immune signal pathways, and compartmentalization of gut bacteria by the mucus layer (Hooper et al., Nat Rev Microbiol 7, pp. 367-374, 2009; Lhocine et al., Cell Host Microbe 4, pp. 147-158, 2008; Paredes et al., Immunity 35, pp. 770-779, 2011; Ryu et al., Science 319, pp. 777-782, 2008). However, the molecular mechanism determining how the gut tolerates symbiotic bacteria without mounting inflammation remains to be elucidated. If the molecular mechanism is understood, it would enable beneficially established commensal microbes to live in a symbiotic relationship and secure a target for controlling the gut immune environment that stimulates elimination of pathogens.

As such, the present inventors have disclosed a direct role of DUOX in gut immune response in *Drosophila* in previous papers (Ha et al., Science, Vol. 310, pp. 847-850, 2005). It has been confirmed that DUOX, which is an NADPH oxidase existing in the mucous membrane of *Drosophila*, plays a pivotal role in immunological activity for microbes by utilizing a genetically recombined *Drosophila* model. Further, as the mechanism for controlling DUOX, the present inventors have disclosed that DUOX activation involves $G\alpha q$-$PLC\beta$-$Ca^{2+}$-mediated signaling pathways and that DUOX expression modulates DUOX gene induction through sequential activation of MEKK1-MKK3-p38 MAPK (Ha et al., Dev Cell 16, pp. 386-397, 2009; Ha et al., Nat Immunol 10, pp. 949-957, 2009b).

In addition to DUOX-dependent gut immunity, pathogen infection can also activate the immune deficiency (IMD) pathway and subsequent nuclear localization of the Relish and NF-kappaB protein, which in turn leads to de novo production of AMPs. DUOX-dependent ROS and IMD-dependent AMP act synergistically or mutually in the gut. The IMD activation is known to be stimulated by peptidoglycan on the cell surface. However, DUOX activity was not activated by peptidoglycan. Instead, the protein-derived ligand for DUOX activation activates DUOX through G-protein-coupled receptor (GPCR) (Bae et al., Trends Immunol 31, pp. 278-287, 2010; Ha et al., Nat Immunol 10, pp. 949-957, 2009b). Despite the presence of extremely efficient DUOX-dependent antimicrobial activation against pathogenic allochthonous bacteria, symbiotic autochthonous bacteria can still colonize the gut without DUOX activation and play their part in maintaining gut-microbe mutualism. However, the microbe-derived factors involved in the activation of DUOX-mediated gut immunity have not yet been determined.

Therefore, the present inventors confirmed that DUOX stimulates a secretion of oxidants in gut cells upon microbial infection, thereby directly acting on gut immunity. However, the reason why gut immunity caused by DUOX is not activated by commensal microbes or the molecular mechanism causing immunological activity is yet to be determined.

On the other hand, uracil, which is one of the nucleobases forming a pyrimidine series of RNA, forms mRNA by combining with adenine in a complementary manner during the transcription process. Uracil is not specifically for pharmaceutical use. However, 5'-fluorouracil (5'-FU), which is an analog of uracil and acts as an antagonistic agent to the pyrimidine nucleobase, is used as a major antitumor agent through antagonistic hexane metabolism, such as DNA synthesis inhibition or RNA dysfunction. Fluorouracil, the uracil analog, is known to cause defects in some mucous membranes of the digestive tract, but the defects are only known to be failures caused by the prevention of cell division and cell denaturation.

DISCLOSURE OF INVENTION

Technical Problem

The present inventors have made extensive efforts to confirm bacteria-derived ligands which stimulate immunological activity in the gut. As a result, they confirmed that an increase in ROS level and immunological activity caused by DUOX in the gut are controlled by uracil secreted by bacteria, and thus discovered a relationship between the level of uracil in the gut, the level of ROS, and gut immune response for the first time, thereby completing the present invention.

Technical Solution

It is an object of the present invention to provide an antimicrobial composition for uracil non-secretory (URA−) bacteria comprising uracil, uracil precursors, uracil analogs, or uracil-secreting opportunistic pathogens as an active ingredient.

It is another object of the present invention to provide a composition for preventing cell damage caused by uracil-secretory (URA+) bacteria, comprising ROS scavengers as an active ingredient.

It is still another object of the present invention to provide food or feed for antimicrobial activity including said composition.

It is still another object of the present invention to provide food or feed for preventing cell damage, including said composition.

It is another object of the present invention to provide a method for stimulating DUOX activation or ROS generation in cells, including treatment with uracil, uracil precursors, uracil analogs, or opportunistic uracil-secreting pathogens.

It is still another object of the present invention to provide a method for reducing ROS levels in cells, including treatment with ROS scavengers.

It is still another object of the present invention to provide a method for producing cells with reduced ROS levels, including treatment with uracil, uracil precursors, uracil analogs, or uracil-secreting opportunistic pathogens.

It is still another object of the present invention to provide a method for reducing ROS levels in cells, including treatment with ROS scavengers.

It is still another object of the present invention to provide a method for providing information on gut pathogenicity in isolated bacteria.

Advantageous Effects of Invention

The composition of the present invention has effects for preventing symptoms caused by bacteria according to a mechanism which has been unknown in the art. Further, the present invention can be efficiently utilized for establishing prevention and treatment strategies of symptoms caused by bacteria later as therapeutic strategies can be readily established by bacterial classification based on criteria that can be easily confirmed.

BRIEF DESCRIPTION OF DRAWINGS

FIG. 1 shows that, unlike commensal bacteria, an opportunistic pathogen secretes a ligand capable of activating DUOX-dependent gut immune response. Data was analyzed by an ANOVA followed by Tamhane's T2 post hoc test, and the value represents mean±SEM (*P<0.05, P<0.005, *P<0.001). N.S. denotes no significance.

Specifically, FIG. 1 shows an observation of ROS generation by staining R19S treating $w^{1118}$ (control) or UAS-DUOX-RNAi/+; Da-GAL4 (DUOX-RNAi) Drosophila species with live bacteria (FIG. 1a), formalin-fixed bacteria (FIG. 1b), or bacteria supernatant (FIG. 1c).

FIG. 1d confirms systemic IMD (immune deficiency) pathway activation in Dipt-lacZ (control) and Dipt-lacZ; $imd^1$ (IMD$^{−/−}$) Drosophila species. Dipt expression was analyzed by quantitative PCR (qPCR) (±SEM) and LacZ staining at 9 hours after treating the culture supernatant.

FIG. 1e confirms gut IMD pathway activation by Cec protein expression. The expression of Cec protein was analyzed by (qPCR) (±SEM) at 9 hours after injection with live bacteria or formalin-fixed dead bacteria (approx. $10^{10}$ or more bacterial cells).

FIG. 2 shows a measurement of DUOX-dependent ROS generation for various bacteria.

Specifically, FIG. 2a shows whether R19S in mammalian epithelial cells specifically reacts with OSCN$^−$ (indicated in the left panel), which is a main antimicrobial ROS, or with OCl$^−$ (indicated in the right panel), which is expressed in DUOX-dependent HOCl.

FIG. 2b shows a time series analysis based on the ratio of ROS-positive gut at 1, 1.5, 3.5, and 6.5 hours after injection, wherein different bacteria (E. carotovora or C. intestine, approx. $5×10^8$ cells) were orally administered to adult Drosophila (5 to 6 days old). Each experiment was repeated at least three times independently, and for each experiment, the n value was 20 or more (i.e. n≥20). Data was analyzed by an ANOVA followed by Tamhane's T2 post hoc test, and the value represents mean±SEM (*P<0.05, P<0.005, *P<0.001). N.S. denotes no significance.

FIG. 2c shows a spatial analysis of DUOX-dependent ROS generation. Sucrose solution alone or live bacteria (E. carotovora, approx. $5×10^8$ cells) were orally administered to adult Drosophila (5 to 6 days old), and DUOX-dependent ROS generation was confirmed with R19S staining at 1.5 hours after injection. ROS was formed intensively in the anterior midgut region.

FIG. 2d shows an analysis of in vivo ROS generation for various bacteria. Various living bacteria ($5×10^8$ cells per each strain) were orally administered to adult Drosophila (5 to 6 days old), and the ratio of ROS-positive gut was analyzed at 1.5 hours after injection. The bacteria used herein were Drosophila-derived symbiotic strains, including Enterococcus faecalis (F. Leulier laboratory, France; Storelli et al., Cell Metab 14, pp. 403-414, 2011), Lactobacillus pentosus (J.-W. Bae laboratory, South Korea), Lactobacillus plantarum CNW10 strain (Douglas laboratory, USA; Storelli et al., 2011), and Acetobacter pasteurianus (J.-W. Bae laboratory, South Korea); and known pathogens such as E. carotovora and Pseudomonas entomophila (Lemaitre laboratory, Switzerland). Further, human opportunistic bacteria, such as E. faecalis-1 (KCTC#3195), E. faecalis-2 (Ferrandon Laboratory, France), Vibrio fluvialis (KCTC#2473), Klebsiella pneumoniae (KCTC#2619), Shigella sonnei (KCTC#2518), Pseudomonas aeruginosa PAO1 (Manoil laboratory, University of Washington), and Sarratia marcescens (ATCC#27117) were also confirmed. Data was analyzed by an ANOVA followed by Tamhane's T2 post hoc test, and the value represents mean±SEM (P<0.005, *P<0.001). N.S. denotes no significance. Each experiment was repeated at least three times independently, and for each experiment, the n value was 20 or more (i.e. n≥20).

FIG. 2e confirms ROS generation in the gut caused by lysed bacteria. Live bacteria (E. carotovora, approx. $5×10^8$ cells) or lysed bacteria (E. carotovora, approx. $5×10^8$ lysed cells) were orally administered to Drosophila (5 to 6 days old), and the ratio of ROS-positive gut was analyzed at 1.5 hours after injection. Each experiment was repeated at least three times independently, and for each experiment, the n value was 20 or more (i.e. n≥20). Data was analyzed by an ANOVA followed by Tamhane's T2 post hoc test, and the value represents mean±SEM (***P<0.001).

FIG. 3 confirms uracil as a pathogen-derived ligand capable of activating DUOX-dependent gut immunity.

Specifically, FIG. 3a shows HPLC analysis for isolation of an ROS-inducing factor by E. carotovora. ROS generation in the anterior midgut was analyzed 1.5 hours after treating HPLC-purified fractions. Data was analyzed by an ANOVA followed by Tamhane's T2 post hoc test, and values represent mean±SEM (***P<0.001). Peaks of interest (peaks indicated by asterisks) were subjected to spectrum analysis by a photodiode array detector (blue boxed).

FIG. 3b confirms that uracil activates gut PLCβ. Uracil was administered to genetically recombined flies carrying UAS-PLCβ-RFP; Da-GAL4 (20 nM for 2 hours).

FIG. 3c confirms that uracil increases intracellular $Ca^{2+}$ in Drosophila S2 cells. Uracil (20 nM) was added at a specific time point (indicated by an arrow).

FIG. 3d confirms that uracil induces p38 activation. The $w^{1118}$ flies (Control) and MEKK1-/-Drosophila were used for phosphor-p38 analysis following uracil treatment (20 nM for 2 hours).

FIG. 3e confirms that uracil stimulates DUOX expression. The $w^{1118}$ flies (Control) and MEKK1-/-Drosophila were used for phosphor-p38 analysis following uracil ingestion (20 nM for 2 hours). DUOX expression levels were measured by qPCR analysis (±SEM, **P<0.005) at 1 hour after ingestion.

FIG. 3f confirms that uracil stimulates PLCβ-DUOX-dependent ROS generation. ROS generation was examined following the administration of uracil (20 nM for 1.5 hours) to the following fly lines: $w^{1118}$ (Control), UAS-DUOX-RNAi/+, Da-GAL4 (DUOX-RNAi), and norpA$^7$ (PLCβ$^{-/-}$). Data was analyzed by an ANOVA followed by Tamhane's T2 post hoc test, and values represent mean±SEM (**P<0.005).

FIG. 4 shows identifying uracil by pathogen-derived ROS-inducing factors.

FIG. 4a shows a 2D $^1$H—$^{13}$C heteronuclear multiple bond correlation (HMBC) spectrum of an ROS-induced fraction of E. carotovora purified by HPLC. After analysis, it was confirmed that the ROS-induced fraction of E. carotovora purified by HPLC included uracil.

FIG. 4b shows a mass spectrometry (MS) analysis of an ROS-induced fraction of E. carotovora purified by HPLC. After evaluating molecular weight and peak data, it was confirmed that the chemical formula was identical to that of uracil ($C_4H_4N_2O_2$).

FIG. 4c shows comparative 1D $^1$H-NMR spectra between an ROS-induced fraction of E. carotovora purified by HPLC and uracil.

FIG. 4d shows a quantitative analysis on the amount of uracil secreted from various bacteria. The following strains were isolated from humans and utilized: Streptococcus pyogenes (KCTC#3096); Lactobacillus gasseri (KCTC#3163); Lactobacillus acidophilus (KCTC#3164); Chryseobacterium indologenes (KCTC#2905); Enterococcus casseliflavus (KCTC#3552); Lactobacillus reuteri (KCTC#3678); Edwardsiella tarda (KCTC#12267); Ewingella americana (KCTC#12690); Vibrio fluvialis (KCTC#2473); Empedobacter brevis (KCTC#2489); Shigella sonnei (KCTC#2518); Klebsiella pneumoniae (KCTC#2619); Streptococcus vestibularis (KCTC#3650); Aneurinibacillus aneurinolyticus (KCTC#3883); Bacillus alcalophilus (KCTC#3884); Acinetobacter junii (KCTC#12406); Acinetobacter schindleri (KCTC#12409); Streptococcus parasanguinis (KCTC#13046), Pseudomonas entomophila (Bruno Lemaitre, EPFL, Switzerland); Listeria monocytogenes (Laboratoire de Microbiologic, INSERM, France); Pseudomonas aeruginosa PAO1 (Manoil laboratory, University of Washington); Enterococcus faecalis; Enterococcus faecalis-2; Staphylococcus aureus; Staphylococcus epidermis (isolated from Drosophila stock in Seoul National University); Lactobacillus casei (Laboratoire de Microbiologic, University of Bourgogne, France); Bacillus thuringiensis (ATCC#10792); Sarratia marcescens (ATCC#27117). 32 bacterial strains were inoculated into complete media containing a high concentration of uracil, and were cultured in M9 the minimal media. Only 7 bacteria proliferated in the M9 minimal media, and the corresponding supernatant was analyzed by LC-MS/MS. The value represents mean±S.D. based on three independent experiments.

FIG. 4e shows that commensal bacteria in the gut cannot suppress ROS generation caused by uracil. 20 nM of uracil was orally administered to adult Drosophila (5 to 6 days old). A ratio of ROS-positive gut was analyzed at 1.5 hours after injection. GF flies and non-bacterial Drosophila (GF+C. intestini, GF+A. pomorum, and GF+L. plantarum) monoassociated with main commensal bacteria were used. Data was analyzed by an ANOVA followed by Tamhane's T2 post hoc test, and the value represents mean±SEM (*P<0.05, **P<0.005). Each experiment was repeated at least three times independently, and for each experiment, the n value was 20 or more (i.e. n≥20).

FIG. 4f confirms that coingestion of uracil with an antioxidant chemical, N-acetylcysteine, abolished the detection of DUOX-dependent ROS. ROS generation in the midgut was visualized by HOCl-specific R19S staining following oral administration of uracil alone (20 nM, 1.5 hours) or of a combination of uracil and N-acetylcysteine. The value represents a ratio of ROS-positive gut. Data was analyzed by an ANOVA followed by Tamhane's T2 post hoc test, and the value represents mean±SEM (***P<0.001). Each experiment was repeated at least three times independently, and for each experiment, the n value was 20 or more (i.e. n≥20). N.S. denotes no significance.

FIG. 4g confirms that uracil stimulates DUOX2-dependent ROS generation in human epithelial cells. Intestinal adenocarcinoma Caco-2 cells, either DUOX2 knocked-down or not (FIG. 4h), or normal preliminary human nose epithelia (FIG. 4i) were treated with uracil (50 nM, 15 minutes). ROS was measured by 2',7'-dichlorofluorescin diacetate. In DUOX2 knocked-down cells (pLZRS-human DUOX2-shRNA), an internal DUOX2 expression level was found to be equal to or less than 20% compared to that of the control group (pLZRS-control shRNA). Fluorescent intensity was measured by the Carl Zeiss vision system (KS400, ver. 3.0). The mean value of 7 values was calculated and compared. The value was indicated as having a fluorescent intensity of 1 in the control group having no uracil treatment. Data was analyzed by an ANOVA followed by Tamhane's T2 post hoc test, and the value represents mean±SEM (***P<0.001). N.S. denotes no significance. Each experiment was conducted at least three times independently.

FIG. 5 shows that uracil is a specific agonist for the DUOX-dependent gut-innate immunity. Data from FIGS. 5a and 5c was analyzed by an ANOVA followed by Tamhane's T2 post hoc test, and the value represents mean±SEM (***P<0.001).

Specifically, in FIGS. 5a and 5b, ROS production was examined following ingestion of different nucleobases (5a) and pyrimidine analogs (20 nM each) for 15 minutes.

FIG. 5c confirms that Gαq is a required factor for uracil-induced ROS generation. The level of ROS generation was compared following uracil ingestion (20 nM for 1.5 hours) to flies under a $w^{1118}$ (Control) or Gαq mutant Drosophila (Gαq$^{-/-}$) background.

FIG. 5d confirms that uracil inactivates IMD pathway in gut cells. Cec expression was analyzed by qPCR (±SEM, ***P<0.001) following ingestion of uracil (20 nM) or live bacteria (approx. $10^{10}$ cells) for 4 hours.

FIG. 6 shows a comparative analysis between WT E. carotovora and their mutants.

FIG. 6a is a schematic diagram showing a screening strategy for isolating uracil non-secretory (uracil-auxotropic) mutants from an E. carotovora Tn5-mutant library. Initially, about 6,000 mutant clones were cultured on M9 minimal media containing uracil or no uracil, and uracil auxotrophy of each clone was confirmed. Accordingly, URA− mutants of the present invention were identified.

FIG. 6b shows that inverse PCR was conducted by the method disclosed in http://labs.fhcrc.org/gottschling/General%20Protocols/iper.html to confirm the Tn5 transposon insertion site of URA− mutants. The primers used herein were KAN-2 forward primer (5'-ACC TAC AAC AAA GCT CTC ATC AAC C-3' (SEQ ID NO: 1)) and KAN-2 reverse primer (5'-GCA ATG TAA CAT CAG AGA TTT TGA G-3' (SEQ ID NO: 2)). After tracking the insertion position by subsequent sequence analysis, it was confirmed that the insertion position was the position for pyrE gene.

FIG. 6c confirms that the ex vivo proliferation rate of the E. carotovora-pyrE::Tn5 strain is similar to that of WT E. carotovora. Data based on the results derived from 3 independent experiments was analyzed by Student's t-test, and the value represents mean±SEM. The analysis showed no statistical significance between URA− mutated strain and WT strain.

FIG. 6d shows scanning electron microscopic (SEM) analysis of WT or URA− mutated E. carotovora strain.

FIG. 6e shows an experiment of bacterial attachment to a non-biological surface (polystyrene plastic). The result was confirmed with crystal violet cell staining Data based on the results derived from 3 independent experiments was analyzed by Student's t-test, and the value represents mean±SEM. N.S. denotes no significance.

FIG. 6f confirms minimal inhibitory concentration (MIC) of Cecropin, wherein Cecropin is an antimicrobial peptide. An adaptability test regarding the MIC of Cecropin A1 was conducted by two times-standard dilution methods following the inoculation of the strain. The MIC was confirmed following the culturing process at 30° C. for 18 hours. The proliferation rate was measured at 620 nm ($OD_{620}$) by an ELISA reader (Molecular Devices Emax, CA, U.S.A.).

FIG. 6g confirms that both WT and URA− strains activate a systemic IMD (immune deficiency) signal pathway at similar levels. Diptericin protein expression stimulated by IMD signal pathways were confirmed with LacZ staining (indicated in the left panel) and RT-PCR analysis (indicated in the right panel) at 9 hours after injection following the inoculation of 50 nL of live bacterial concentrates (approx. $10^{10}$ cells) into adult Drosophila (5 to 6 days old) having Drs-GFP and Dipt-lacZ genes. The value obtained from Diptericin protein expression in non-administered Drosophila was adjusted to 1 and the values were compared. The value subjected to the comparison represents mean±SEM obtained from at least 3 independent experiments. N.S. denotes no significance.

FIG. 6h confirms that both WT and URA− strains activate a systemic IMD (immune deficiency) signal pathway at similar levels. Diptericin protein expression stimulated by IMD signal pathways were confirmed with LacZ staining (indicated in the left panel) and RT-PCR analysis (indicated in the right panel) at 9 hours after injection following the inoculation of 50 nL of live bacteria concentrates (approx. $10^{10}$ cells) into adult Drosophila (5 to 6 days old) having Drs-GFP and Dipt-lacZ genes. The value obtained from Diptericin protein expression in non-administered Drosophila was adjusted to 1 and the values were compared. The value subjected to the comparison represents mean±SEM obtained from at least 3 independent experiments. N.S. denotes no significance.

FIG. 6i confirms insertion positions by isolating guanine- and adenine non-secretory (adenine-auxotrophic) mutant strains separately. Each mutant was isolated by utilizing M9 minimal media regardless of the presence of guanine- and adenine-based on the strategy of FIG. 6a, and subsequent sequence analysis was utilized to analyze the insertion position of Tn5 in guanine non-secretory (guanine-auxotrophic) mutant strains (E. carotovora-guaA::Tn5, indicated in the upper panel) and adenine non-secretory mutant strains (E. carotovora-purC::Tn5, indicated in the lower panel). The result showed that Tn5 in each mutant was inserted into guanine monophosphate synthetase (guaA) and phosphoribosyl aminoimidazole-succinocarboxamide synthase (purC) genes.

FIG. 6j confirms that both guanine- and adenine non-secretory mutant strains have similar levels of ROS-generating capability compared to WT E. carotovora. ROS generation in the midgut was visualized by HOCl-specific R19S staining at 1.5 hours after injection following the administration of WT or non-secretory(auxotrophic) mutant strain bacteria to adult Drosophila (5 to 6 days old), and a ratio of ROS-positive gut was obtained. Data was analyzed by an ANOVA followed by Tamhane's T2 post hoc test, and the value represents mean±SEM (***P<0.001). N.S. denotes no significance. Each experiment was repeated at least three times independently, and for each experiment, the n value was 20 or more (i.e. n≥20).

FIG. 7 confirms that pathogen-derived uracil is required for DUOX-dependent antimicrobial ROS generation and interstitial stem cell homeostasis. It was confirmed that reduced ROS generation caused by treatment with E. carotovora mutant strains was recovered by uracil treatment and pyrE gene recovery. In FIGS. 7a, 7c, and 7d, data was analyzed by an ANOVA followed by Tamhane's T2 post hoc test, and the value represents mean±SEM (*P<0.05, P<0.005, *P<0.001).

FIG. 7a confirms significantly reduced ROS generation with treatment URA− E. carotovora mutant strains (E. carotovora-pyrE::Tn5) compared to ROS generation caused by WT E. carotovora strains. It was confirmed that reduced ROS generation caused by treatment with E. carotovora mutant strains was recovered by uracil treatment and pyrE gene recovery.

FIGS. 7b to 7e show that bacteria-derived uracil controls an epithelial cell renewal program. All analyses were performed on $w^{1118}$ (Control) and PLCβ$^{-/-}$ Drosophila species.

FIG. 7b shows an analysis of escargot-positive cells in the anterior midgut region at 22 hours after injection of WT E. carotovora or E. carotovora-pyrE::Tn5 (uracil used in combination or pyrE recovery) to Drosophila having escargot-GAL4>UAS-GFP genes.

FIG. 7c shows an analysis of gut stem cell (ISC) proliferation caused by pH3 staining.

FIG. 7d shows an analysis of enteroblast differentiation. Su(H)Gbe-LacZ and Prospero were analyzed by Su(H)Gbe- LacZ *Drosophila*. A ratio of LacZ-positive or Prospero-positive cells per 100 DAPI-positive cells was determined FIG. 7e shows an analysis of Upd3 promoter and STAT reporter gene (GFP) activations at 4 hours after injection by *Drosophila* having Upd3-gal4>UAS-GFP or 2XSTAT-GFP genes.

FIG. 8 shows a time series analysis of the epithelial cell renewal program and cell apoptosis caused by gut infection. Samples were collected at 16, 24, 48, and 72 hours following the oral administration of 5% sucrose solution containing different bacteria (*E. carotovora* or *E. carotovora*-pyrE::Tn5, $5 \times 10^8$ cells) to *Drosophila*. Data was analyzed by an ANOVA followed by Tamhane's T2 post hoc test, and the value represents mean±SEM (*$P<0.05$, $P<0.005$, *$P<0.001$). Each experiment was repeated at least three times independently, and for each experiment, the n value was 20 or more (i.e. n≥20).

FIG. 8a shows a comparative and quantitative time series analysis of pH3-positive mitotic gut stem cells in the midgut. Mitotic gut stem cells in non-infected *Drosophila* (16 hours after injection of sucrose alone) were adjusted to 1 and the values were quantitatively compared to one another by anti-pH3 antibody.

FIG. 8b shows a time series comparison for enteroblast differentiation. Su(H)Gbe-LacZ and Prospero were analyzed by Su(H)Gbe-LacZ *Drosophila*. A ratio of LacZ-positive or Prospero-positive cells per 100 DAPI-positive cells was determined FIG. 8c shows a time series comparison for the ratio of cell apoptosis by TUNEL analysis.

FIG. 9 confirms that an appropriate level of uracil-induced immune response is required for host survival.

FIG. 9a confirms bacteria persistence in the midgut. The number of colony-forming units (CFU) in the midgut was measured at 6 hours after ingestion (n=30 per each experimental set). Data was analyzed by the Kruskal-Wallis test followed by the Mann-Whitney U-test using Bonferroni correction to adjust the probability. Bonferroni-adjusted p values were used (Bonferroni correction) (***$P<0.001$).

FIG. 9b shows that URA– pathogens (*E. carotovora*-pyrE::Tn5) induce high host mortality compared to that of WT pathogens (*E. carotovora*). On the other hand, *E. carotovora*-guaA::Tn5 and *E. carotovora*-purC::Tn5 were used for guanine- and adenine non-secretory mutants, respectively. $w^{1118}$ (Control) and UAS-DUOX-RNAi/+; Da-GAL4 (DUOX-RNAi) *Drosophila* mutants were used. Obtained Kaplan-Meier data was analyzed by a log-rank test ($P<0.001$, *E. carotovora* vs. *E. carotovora*-pyrE::Tn5; *E. carotovora*-pyrE::Tn5 vs. *E. carotovora*-pyrE::Tn5+uracil or *E. carotovora*-pyrE::Tn5+pyrE).

FIG. 9c confirms gut cell apoptosis according to chronic uracil administration (1 nM) using GF animals having various genetic backgrounds (GF-control, GF-DUOX-RNAi, or GF-PLCβ$^{-/-}$). The cell apoptotic index (20 days after chronic uracil administration) was analyzed by an ANOVA followed by Tamhane's T2 post hoc test, and the value represents mean±SEM (*$P<0.05$).

FIG. 9d confirms host mortality according to chronic uracil administration using GF animals having various genetic backgrounds (GF-control, GF-DUOX-RNAi, or GF-PLCβ$^{-/-}$). A log-rank analysis on the Kaplan-Meier data showed a statistically significant difference in mortality between normal food and uracil-containing food in the case of GF-control flies ($P<0.001$), but not in the case of GF-DUOX-RNAi ($P=0.8$) or GF-PLCβ$^{-/-}$ ($P=0.5$).

FIG. 10 confirms physiological effects of uracil on gut cells.

FIGS. 10a to 10e confirm that uracil ingestion induces an epithelial cell renewal program by activating a JAK-STAT signal pathway. A 5% sucrose solution (20 nM) was orally administered to adult *Drosophila* (5 to 6 days) of different genotypes ($w^{1118}$ or PLCβ$^{-/-}$) regardless of the presence of uracil. In FIGS. 10b and 10c, data based on the results derived from three independent experiments was analyzed by Student's t-test, and the value represents mean±SEM (***$P<0.001$). N.S. denotes no significance. Each experiment was repeated at least three times independently.

FIG. 10a shows the results from an analysis of escargot-positive cells in the anterior midgut at 22 hours after injection of WT *E. carotovora* or *E. carotovora*-pyrE::Tn5 (uracil used in combination or pyrE recovery) by utilizing *Drosophila* having escargot-GAL4>UAS-GFP genes.

FIG. 10b shows an analysis of gut stem cell (ISC) proliferation with pH3 staining FIG. 10c shows an analysis of enteroblast differentiation. Su(H)Gbe-LacZ and Prospero were analyzed by utilizing Su(H)Gbe-LacZ *Drosophila*. The ratio of LacZ-positive or Prospero-positive cells per 100 DAPI-positive cells was determined.

FIG. 10d shows an analysis of Upd3 promoter activation at 4 hours after injection using *Drosophila* having Upd3-gal4>UAS-GFP genes.

FIG. 10e shows an analysis of STAT reporter gene (GFP) activation 4 hours after injection following the administration using *Drosophila* having 2XSTAT-GFP genes.

FIG. 10f confirms DUOX-dependent gut cell apoptosis caused by chronic administration of uracil by utilizing genetically different ($w^{1118}$ (Control) or UAS-DUOX-RNAi/+; Da-GAL4 (DUOX-RNAi)) germ-free (GF) animals. A 5% sucrose solution containing different uracil concentrations was orally administered to adult *Drosophila* (5 to 6 days old) for 7 days. Cell apoptosis (20 days after injection following chronic administration of uracil) was analyzed by an ANOVA followed by Tamhane's T2 post hoc test, and the value represents mean±SEM (***$P<0.001$). N.S. denotes no significance. Each experiment was repeated at least three times independently.

FIG. 10g confirms DUOX-dependent host mortality caused by chronic administration of uracil by utilizing genetically different ($w^{1118}$ (Control) or UAS-DUOX-RNAi/+; Da-GAL4 (DUOX-RNAi)) germ-free (GF) animals Germ-free feed containing different uracil concentrations were provided for adult *Drosophila* (5 to 6 days old) for 7 days. The survival rate was observed in three or more cohort groups, each consisting of about 25 *Drosophila*. A log-rank analysis on the Kaplan-Meier data showed a significant difference when providing feed containing 0.1 nM, 1 nM, or 10 nM of uracil ($P<0.01$) relative to normal feed, but not in the case of providing 0.001 mM or 0.01 nM of uracil (0.001 nM uracil: $P=0.147$; 0.01 nM uracil: $P=0.107$).

FIG. 11 confirms that *G. morbifer* can act as natural commensal bacteria in the gut due to chronic DUOX-activation caused by its constant release of uracil. Data was analyzed by an ANOVA followed by Tamhane's T2 post hoc test (FIGS. 11a, 11c, and 11d) or Tukey's post hoc test (FIG. 11b), and the value represents mean±SEM (*$P<0.05$, $P<0.005$, *$P<0.001$).

FIG. 11a confirms ROS generation by *G. morbifer*. The flies used herein are $w^{1118}$ (Control), UAS-DUOX-RNAi/+; Da-GAL4 (DUOX-RNAi), or norpA$^7$ (PLCβ$^{-/-}$)). Basal levels of gut ROS were measured in GF animals (GF-control, GF-DUOX-RNAi) wherein each of them was monoassociated.

FIG. 11b confirms cell apoptotic index by *G. morbifer*. The flies used herein were w[1118] (Control), UAS-DUOX-RNAi/+; Da-GAL4 (DUOX-RNAi), or norpA[7](PLCβ$^{-/-}$).

FIG. 11c confirms that a monoassociation associated with ROS generation is abolished when a URA− mutant strain (*G. morbifer*-carA::Tn5) of *G. morbifer* is used in an experiment with GF-control animals FIG. 11d confirms that a monoassociation associated with gut cell apoptosis is abolished when a URA− mutant strain (*G. morbifer*-carA::Tn5) of *G. morbifer* is used in an experiment with GF-control animals.

FIG. 11e confirms that the URA− mutant strain (*G. morbifer*-carA::Tn5) of *G. morbifer* colonizes gut epithelia as efficiently as WT *G. morbifer*. The numbers of CFUs were measured from the midgut at 13 days after injection of *G. morbifer* or *G. morbifer*-carA::Tn5. Data was analyzed by the Mann-Whitney U-test.

FIG. 11f confirms that chronic activation of a PLCβ-DUOX signal pathway by *G. morbifer*-derived uracil is the direct cause of host mortality. A log-rank analysis on the Kaplan-Meier data showed a significant difference in survival between a *G. morbifer* monoassociation and a *G. morbifer*-caA::Tn5 monoassociation in the case of control flies (P<0.001), but not in the case of GF-DUOX-RNAi flies (P=0.59) or GF-PLCβ$^{-/-}$ (P=0.47) when the experiment was based on GF-control.

FIG. 12 shows whether *G. morbifer* or *A. pomorum*, and ROS coexist and provide a method for producing uracil non-secretory *G. morbifer* mutants. *G. morbifer*-GFP and *A. pomorum*-GFP were produced for visualization. w[1118] (Control), UAS-DUOX-RNAi/+; Da-GAL4 (DUOX-RNAi), and norpA[7] (PLCβ$^{-/-}$) *Drosophila* species were used. GF animals (Control, DUOX-RNAi and PLCβ$^{-/-}$) that were monoassociated with *G. morbifer*-GFP or *A. pomorum*-GFP were produced.

FIG. 12a shows the entire gut of the GF animals, and it was confirmed that *G. morbifer* and ROS coexisted intensively in the anterior midgut region.

FIG. 12b shows an upper part of iron and copper cells, and it is known that morphologically large cells are known as cells with copper accumulation. It is observed that *G. morbifer* and ROS coexist in the anterior midgut of control *Drosophila*. ROS generation was not observed in either PLCβ-DUOX signaling *Drosophila* mutants monoassociated *G. morbifer* or control *Drosophila* monoassociated *A. pomorum*.

FIG. 12c confirms that *A. pomorum* bacteria mainly colonize the anterior region of the midgut.

FIG. 12d shows production of uracil non-secretory *G. morbifer* mutants. A screening strategy for isolating uracil non-secretory mutants is also disclosed. According to recently completed *G. morbifer* genome sequences (Kim et al., J Bacteriol 194, 1245, 2012), *G. morbifer* carA genes have a 51% homology in amino acid sequence with carA gene of E. coli. *G. morbifer* carA mutants were screened, wherein the open reading frame of the carA gene contains transposons following the insertion of the mutation into carA genes, particularly using the Rows and Columns PCR screening strategies. For the screening, carA gene primers such as carA forward primer were used (5'-CGG ACT GGA AGC CGT CCG CAA ATG GCG-3' (SEQ ID NO: 3)) and carA reverse primer (5'-CGA AAC GCT CGA AAA GAT AGA AAC TGT C-3' (SEQ ID NO: 4)). Further, the primers used for confirming the insertion position of Tn5 transposons were KAN-2 forward primer (5'-ACC TAC AAC AAA GCT CTC ATC AAC C-3' (SEQ ID NO: 1)) and KAN-2 reverse primer (5'-GCA ATG TAA CAT CAG AGA TTT TGA G-3' (SEQ ID NO: 2)). As a result, *G. morbifer*-carA::Tn5 mutant candidate clones were obtained.

FIG. 12e shows whether transposons were inserted in between carA genes by utilizing the *G. morbifer*-carA::Tn5 mutant candidate clones as well as EZ::Tn5™ <KAN-2>Tnp Transposome™ kit (Epicentre).

FIG. 13 confirms that *L. brevis* can act as natural commensal bacteria that can cause colitis by chronic DUOX-activation due to its constant release of uracil. To produce a URA− *L. brevis* mutated strain, a two-step homologous recombination method (Barthelmebs et al., Appl Environ Microbiol 66, pp. 3368-3375, 2000) was used to produce *L. brevis*ΔcarA strain, wherein an amino acid at position 281 was removed from position 71 of carA gene.

FIG. 13a confirms that colonization of WT *L. brevis* stimulates PLCβ-dependent chronic generation of ROS unlike URA− *L. brevis* mutants (*L. brevis*ΔcarA) in genetically different *Drosophila* species (w[1118] (Control) or norpA[7] (PLCβ$^{-/-}$)). Germ-free animals (GF-control, GF-PLCβ$^{-/-}$) with different genetic backgrounds were monoassociated with each commensal bacterium (approx. 10$^6$ CFUs), respectively. Data was analyzed by an ANOVA followed by Tamhane's T2 post hoc test, and the value represents mean±SEM (***P<0.001). Each experiment was repeated at least three times independently, and for each experiment, the n value was 20 or more (i.e. n≥20).

FIG. 13b shows the result obtained from a monoassociation of different genetic *Drosophila* species (GF-control or GF-PLCβ$^{-/-}$) to WT *L. brevis* or to URA− *L. brevis* mutants (*L. brevis*ΔcarA). Data was analyzed by an ANOVA followed by Tukey's post hoc test, and the value represents mean±SEM (***P<0.001). N.S. denotes no significance. Each experiment was repeated at least three times independently.

FIG. 13c confirms that URA− *L. brevis* mutants (*L. brevis*ΔcarA) and WT *L. brevis* colonize gut epithelial cells at similar levels. GF-control animals were monoassociated *L. brevis* or to URA− *L. brevis* mutants (*L. brevis*ΔcarA), and the midgut was equalized and diluted. The midgut was cultured on an MRS agar plate and CFU for each midgut region was measured. Data was analyzed by the Mann-Whitney U-test (n=20). There was no statistically significant difference. N.S. denotes no significance.

FIG. 13d confirms that chronic activation of a PLCβ-DUOX signal pathway by *L. brevis*-derived uracil is the direct cause of host mortality. Genetically different *Drosophila* species (GF-control or GF-PLCβ$^{-/-}$) were monoassociated with *L. brevis* or to URA− *L. brevis* mutants (*L. brevis*ΔcarA). In all cases, the survival rate was observed in three or more cohort groups, each consisting about 25 *Drosophila*. A log-rank analysis on the Kaplan-Meier data showed a statistically significant difference between *L. brevis* monoassociation and a URA− *L. brevis* mutant (*L. brevis*ΔcarA) in the case of GF-control flies (P<0.01), but not in the case of GF-PLCβ$^{-/-}$ (P=0.694).

FIG. 14 is a schematic diagram showing models for gut-microbe symbiosis and gut-microbe pathogenesis caused by uracil. Bacterial contact can be divided into 4 different categories as below. That is, gut immunity is activated by contact with URA+ allochthonous bacteria (A); insufficient gut immunity is caused by contact with URA− allochthonous bacteria (B); gut immunity is chronically activated by contact with URA+ autochthonous bacteria (C); and both immune adaptability and gut-microbe symbiosis exist by contact with URA− autochthonous bacteria.

BEST MODE FOR CARRYING OUT INVENTION

In one aspect for achieving the above-described objects, the present invention provides an antimicrobial composition for uracil non-secretory (URA−) bacteria, comprising uracil, uracil precursors, uracil analogs, or uracil-secreting opportunistic pathogens as an active ingredient.

As used herein, the term "uracil", which refers to one of the nucleobases in a pyrimidine series of RNA, has a chemical formula of $C_4H_4N_2O_2$ and forms mRNA by combining with adenine in a complementary manner during the transcription process. As used herein, uracil may include uracil, uracil precursors, and uracil analogs as long as they function to stimulate ROS generation by a PLCβ-DUOX signal pathway.

When used as an antimicrobial composition, uracil can be used with uracil precursors, uracil analogs, or uracil-secreting non-pathogenic microbes as well as existing antimicrobial compositions and antimicrobial substances.

As used herein, the term "uracil precursors" may refer to substances transforming into uracil following biologically or chemically specific reactions, particularly the substance transforming into uracil by an endogenous mechanism when administered to the body. Further, in comparison with uracil, the substance may have better chemical stability and storage capability in its composition form compared to uracil.

As used herein, the term "uracil analogs" may include all substances similar to uracil which function to stimulate ROS generation by a PLCβ-DUOX signal pathway in the body. Further, in comparison with uracil, the substances may have better chemical stability and storage capability in its composition form.

As used herein, the term "uracil-secreting opportunistic pathogens" can include microbes with uracil-secreting ability, which have harmlessness as a basis when the corresponding microbes are administered to the body, without any limitations. Uracil derived from the corresponding microbes stimulates immunological activity of the cells in contact by stimulation of ROS generation caused by a PLCβ-DUOX signal pathway, thus stimulating immunological activity against other pathogenic bacteria.

That is, uracil, uracil precursors, uracil analogs, and uracil-secreting opportunistic pathogens function to activate DUOX. Specifically, DUOX is activated by PLCβ activation, which is a prior mechanism, and ROS generation is stimulated by DUOX activation. Stimulated ROS generation conclusively increases immunological activity of the cells, and therefore carries a wide range of antimicrobial functions. A detailed mechanism of DUOX activation and stimulation of ROS generation is disclosed in the cited reference (Ha et al., Science 310, pp. 847-850, 2005).

The mechanism that increases immunological activity of the uracil, uracil precursors, uracil analogs, and uracil-secreting opportunistic pathogens may occur in gut cells, for example, gut epithelial cells. Uracil, uracil precursors, uracil analogs, or uracil-secreting non-pathogenic microbes may activate PLCβ and/or dual oxidase (DUOX) in gut cells, and DUOX may increase the level of ROS in the gut cells.

As used herein, the term "uracil non-secretory (URA−) bacteria" does not only refer to the bacteria requiring additional uracil while growing and developing the corresponding bacteria, but also generally refers to the bacteria not secreting uracil under the specific environment.

As used herein, while culturing the corresponding bacteria, the term refers to the bacteria that do not activate a PLCβ-DUOX signal pathway due to the lack of uracil-secreting ability rather than inability to synthesize uracil. That is, the term refers to the bacteria that are also unable to activate immunological activity by ROS generation stimulated by a PLCβ-DUOX-signal pathway due to the inability of synthesizing or secreting uracil. Due to the inability to activate immunological activity, the survival rate increases without being attacked by ROS.

As used herein, uracil non-secretory bacteria may be allochthonous bacteria.

As used herein, the term "allochthonous bacteria" refers to the bacteria not colonizing epithelial cells, even if the bacteria administered from an external environment come into contact with the epithelial cells and cause symptoms or reactions. That is, the term refers to the bacteria which do not have a characteristic of forming bacteria species by settling into the specific region of the host cell.

As used herein, the term "antimicrobial" refers to an ability to resist bacteria and all of the mechanisms for defending against microbial actions, such as bacteria or fungi.

As used herein, the term "microbes" refers to organisms belonging to bacteria, which are the most dispersed species among all organisms and still have a characteristic of prokaryotes, but do not have the structures, such as nuclear envelope, mitochondria, or chlorophyll. The size is variable, ranging from 0.5 μm to 0.5 mm. The microbes, for example, include *Staphylococcus aureus, Escherichia coli,* and *Pseudomonas aeruginosa,* but also include all of the above-described microbes whose action is defended against by the composition of the present invention without any limitations.

The antimicrobial composition of the present invention may refer to a pharmaceutical composition.

The antimicrobial composition of the present invention may contain not only active ingredients of the present invention, but also more than one said active ingredient, which has antimicrobial activation.

Further, the antimicrobial composition of the present invention may further include pharmaceutically acceptable carriers, excipients, or diluents.

As used herein, the term "pharmaceutically acceptable carriers" refers to liquids or solid fillers that involve carrying or transporting random compositions or ingredients from an organ or part of the body to different organs or parts of the body, or pharmaceutically acceptable substances, such as diluents, excipient, solvent, or capsules, compositions, or vehicles. The composition of the present invention can further include pharmaceutically acceptable carriers, excipients, or diluents in addition to the above-described active ingredients for administration. The carriers, excipients, and diluents include lactose, dextrose, sucrose, sorbitol, mannitol, xylitol, erythritol, maltitol, starch, acacia rubber, alginate, gelatin, calcium phosphate, calcium silicate, cellulose, methyl cellulose, non-refined cellulose, polyvinyl pyrrolidone, water, methyl hydroxybenzoate, propyl hydroxybenzoate, talc, magnesium stearate, and mineral oil.

In addition to this, the antimicrobial composition of the present invention can be formulated and used in an oral form including powders, granules, tablets, capsules, suspensions, emulsions, syrups, aerosols, external forms, suppository forms, or forms of sterilized injection solution according to the method known in the art. Specifically, when formulated, the composition can be prepared by generally used diluents or excipients including fillers, bulking agents, binders, wetting agents, disintegrating agents, or surfactants. Solid formulations for oral administration include tablets, pills, powders, granules, and capsules, but are not particularly limited thereto. The solid formulation can be prepared by mixing the compound of the above-described Formula 1 or 2 with one or more excipients, for example, starch, calcium carbonate, sucrose, lactose, and gelatin. Further, lubricants, such as magnesium stearate or talc can be used in addition to simple excipients. Liquid agents for oral administration include suspensions, liquid medicines, emulsion, and syrup, but are not particularly limited thereto. The liquid agents can be prepared by adding generally used simple diluents, such as water and liquid paraffin, as well as various excipients, for example, wetting agents, sweetening agents, air fresheners, and preserving agents. Agents for non-oral administration include sterilized aqueous solutions, non-aqueous solvents, suspensions, emulsions, lyophilization agents, and suppositories. As a non-aqueous solvent and suspension, vegetable oil including propylene glycol, polyethylene glycol, and olive oil, or an ester capable of injection including ethyl oleate can be used. As a base material for the suppository, Witepsol, Macrogol, Twin 61, cacao butter, laurinum, and glycerogelatin can be used.

Additionally, the antimicrobial composition of the present invention can be orally administered or non-orally administered (for example, can be administered to a vein, subcutaneous region, abdominal cavity, or local region) according to the method based on its purpose. Although dosage may differ based on the status and weight of patients, degree of disease, form of drugs, and administration route and duration, the composition can be determined accordingly by one of ordinary skill in the art. If necessary, the composition can be administered once or several times per day, can be used solely for prevention and treatment of bacteria, and can also be used in combination with the methods for surgery, hormone therapy, drug therapy, and controlling agents for biological reactions.

The antimicrobial composition of the present invention may refer to a quasi-drug composition. That is, the present invention provides the quasi-drug composition for the purpose of prevention or improvement of infectious diseases caused by bacteria. The present invention provides quasi-drug composition for preventing or improving infectious diseases caused by bacteria.

The quasi-drug composition of the present invention can be used with other quasi-drugs or active ingredients thereof, and thus the composition can be used according to the method known in the art. The mixed amount of active ingredients can be determined properly according to the purpose (i.e. prevention, health, or therapeutic use). The quasi-drug composition may refer to disinfecting cleansers, shower foams, mouthwash, wet tissues, detergent soaps, hand wash, humidifier fillers, masks, ointment creams, and filter fillers, but are not particularly limited thereto.

In another aspect, the present invention provides a method for preventing or treating infectious diseases caused by uracil non-secretory (URA−) microbes or microbes secreting only a small amount of uracil, comprising administration of a therapeutic dose of the antimicrobial composition of the present invention to the individual.

As used herein, the term "prevention" refers to all of the activities that inhibit infectious diseases caused by the above-described bacteria or postpone occurrence of diseases by the administration of the composition. The term "treatment" refers to all of the activities of which symptoms caused by infectious diseases become improved or beneficially changed by the administration of the composition. As used herein, the term "individual", which refers to mammals that include cows, pigs, sheep, chickens, dogs, humans, and birds, also refers to all animals including humans where infectious diseases have occurred or might occur later. By administering the composition of the present invention to the individual, the above-described diseases can be prevented or treated effectively.

In one embodiment of the present invention, the example confirms that an appropriate level of uracil-induced immune response is required for host survival (FIG. 9b).

In another aspect, the present invention provides the composition for preventing cell damage caused by uracil-secretory (URA+) bacteria, comprising uracil scavengers, uracil antagonists, and/or ingredients for reducing the uracil level in the body as an active ingredient.

The uracil scavengers, uracil antagonists, or ingredients reducing the uracil level in the body have functions including elimination of uracil secreted from the uracil-secretory (URA+) bacteria, reduction of the level of uracil, or inhibition of the function of uracil without any limitations. Thus, PLCβ activation caused by uracil secreted by uracil-secretory (URA+) bacteria and DUOX activation and/or ROS generation can be inhibited.

In another aspect, the present invention provides the composition for preventing cell damage caused by uracil-secretory (URA+) bacteria, comprising ROS scavengers as an active ingredient.

As used herein, the term "ROS scavengers" refers to substances which eliminate ROS or ROS activation. That is, the level of ROS generation that is stimulated by DUOX activation caused by uracil from uracil-secreting bacteria may be decreased. Further, the ROS scavengers may include substances selected from the group consisting of uric acid, bilirubin, vitamin C, vitamin E, carotene, lycopene, rutin, catechin, flavonoid, copper, zinc, manganese, magnesium, iron, and selenium, but are not particularly limited thereto.

As used herein, ROS scavengers refer to the oxygen species that have oxidizing power with high reactivity in an unstable state. Because ROS have strong reactivity, they can cause damage by reacting with the main ingredients of the composition in the body, such as lipid, protein, and nucleic acids. As used herein, the cells may produce ROS to attack external bacteria, but even if the attack is on external substances, the cells may also be denatured or destroyed with chronic exposure to ROS. As used herein, HOCl could be an ROS produced by activation of PLCβ and/or DUOX.

As used herein, the term "uracil-secretory (URA+) bacteria" refers to the bacteria that not only produce uracil for survival by themselves, but also have an ability to secrete uracil towards an external environment.

As used herein, with the ability to produce or secrete uracil, the term refers to the bacteria which secrete uracil within the cells in the body and activate immunological activity from the stimulation of ROS generation by uracil-derived PLCβ-DUOX signal pathways. By activating immunological activity, ROS generation in the cells is stimulated and the level of ROS in the cells is increased.

As used herein, uracil-secretory (URA+) bacteria may be autochthonous bacteria.

As used herein, the term "autochthonous bacteria" refers to the microbes with a characteristic of being introduced from an external environment and colonizing the epithelial cells by contact therewith. That is, the term refers to the bacteria which have a characteristic of forming bacterial species by settling in the specific region of the host cell. Autochthonous bacteria generally refer to the bacteria which have evolutionarily adapted to the host environment and survived immunological reactions in the body. Further, the bacteria include commensal bacteria, which settle in the body and help with beneficial mechanism for the survival of the host. For example, in the case of cows, the cows include various microbes for digesting plant cellulose in the stomach, and these microbes transform plant cellulose into an absorptive form, and thus have a symbiotic relationship with the cow, which is the host, wherein the microbes play an essential role for the survival of the host.

As used herein, the term "cell damage" refers to all types of cell damage caused by uracil-secreting bacteria, for example, oxidative stress caused by ROS, but is not particularly limited thereto. The above-described cells may be enterocytes, for example, gut epithelial cells. As used herein, the cell damage may be caused by an increase in ROS by PLCβ and/or DUOX activation from uracil-secretory bacteria.

As used herein, the term "prevention" refers to all of the activities that inhibit cell damage caused by the above-described bacteria or postpone symptoms by the administration of the composition.

As used herein, the composition for preventing cell damage may be a pharmaceutical composition.

As used herein, the composition for preventing cell damage may contain not only ROS scavengers of the present invention, but also various types of antioxidants for protecting cells from oxidative stress, or one or more said active ingredients having antimicrobial activation against uracil-secretory (URA+) bacteria.

Further, as used herein, the composition for preventing cell damage can further include pharmaceutically acceptable carriers, excipients, or diluents.

As used herein, the term "pharmaceutically acceptable carriers, excipients, or diluents" is similar to those described above. Further, the formulation or administration method of the pharmaceutical composition is similar to the above explanation.

In another aspect, the present invention provides antimicrobial food or feed for preventing cell damage caused by uracil non-secretory (URA−) bacteria, comprising the above-described composition for preventing cell damage.

Uracil non-secretory (URA−) bacteria are similar to the above explanation.

Antimicrobial food including the above antimicrobial composition is not particularly limited, and the content of the composition included in the food additives is also not particularly limited, and thus, they can be easily determined by one of ordinary skill in the art considering the infectious ability or infectious level of various microbes.

The examples of food containing the antimicrobial composition of the present invention include dairy products, such as meat, sausages, bread, chocolate, candies, snacks, cookies, pizza, noodles, other instant noodles, gum, ice cream, various soup, drinks, tea, health drinks, alcohol and vitamin complexes, and can also include all generally known health functional food and food for animal feed.

Further, when the antimicrobial composition is used upon addition to drinks, the composition may contain various sweeteners, flavoring agents, or natural carbohydrates as additional ingredients as in general drinks The natural carbohydrates may be monosaccharides including glucose and fructose, disaccharides including maltose and sucrose, polysaccharides including dextrin and cyclodextrin, and sugar alcohols including xylitol, sorbitol, or erythritol. The ratio of the natural carbohydrates is not particularly limited to the above list, but the ratio could be about 0.01 g to 0.04 g, specifically, 0.02 g to 0.03 g, per 100 mL of food including the antimicrobial composition of the present invention. The above sweeteners may be natural sweeteners including thaumatin or stevia extracts, and synthetic sweeteners including saccharin or aspartame.

Food that contains the antimicrobial composition in addition to the above may include various nutritional supplements, vitamins, electrolytes, flavoring agents, coloring agents, pectic acid and its salts, alginic acid and its salts, organic acids, protective colloid thickeners, pH regulators, stabilizers, antiseptics, glycerin, alcohol, and magnesium carbonate used for carbonated soft drinks In addition, natural fruit juice and fruit flesh for preparing fruit juice and vegetable juice may be included.

As in the case of food above, the antimicrobial feed including the above composition for preventing cell damage is not particularly limited, and the content of the antimicrobial composition included in the above-described feed is also not particularly limited, and they can be easily determined by one of ordinary skill in the art considering the infectious ability or infectious level of various microbes.

In another aspect, the present invention provides food or feed for preventing cell damage caused by uracil-secreting (URA+) bacteria, comprising the above composition for preventing cell damage.

Food for preventing cell damage including the above composition for preventing cell damage is not particularly limited, and the content of the composition included in the above food additives s also not particularly limited, and they can be easily determined by one of ordinary skill in the art considering the level of various oxidative stresses or degree of cell damage.

Food that contains the above composition for preventing cell damage is similar to the above explanation regarding food that contains the above antimicrobial composition.

As in the case of food above, feed for preventing cell damage wherein the composition for preventing cell damage can be used is not particularly limited, and the content of the composition for preventing cell damage included in the above-described feed is also not particularly limited, and they can be easily determined by one of ordinary skill in the art considering the level of various oxidative stresses or degree of cell damage.

In another aspect, the present invention provides a method for stimulating DUOX generation in cells, comprising treating cells with uracil, uracil precursors, uracil analogs, or uracil-secretory non-pathogenic microbes. Further, the present invention provides a method for stimulating ROS generation in cells, comprising treating cells with uracil, uracil precursors, uracil analogs, or uracil-secretory non-pathogenic microbes.

The cells may be ex vivo cells, in vivo cells, or in vitro cells. The cells, for example, can be gut cells, gut stem cells, or gut epithelial cells.

By treating the cells with uracil, uracil precursors, uracil analogs, or non-pathogenic microbes producing uracil, PLCβ and/or DUOX are activated by the above mechanism and ROS generation is stimulated by DUOX activation. Therefore, immunological activity of the cells can be activated.

In another aspect, the present invention provides a method for reducing an ROS level in cells, comprising treating the cells with uracil scavengers, uracil agonists, or substances reducing the level of uracil while comparing with the control group of cells without ROS scavenger treatment.

The above cells may be ex vivo cells, in vivo cells, or in vitro cells. The cells, for example, can be gut cells, gut stem cells, or gut epithelial cells.

By treating the cells with uracil scavengers, uracil antagonists, or substances that reduce the level of uracil, ROS generation is inhibited by uracil-derived PLCβ and/or DUOX activation based on the above mechanism. Therefore, immunological activity of the cells can be inhibited.

In another aspect, the present invention provides a method for reducing an ROS level in cells, comprising treating the cells with ROS scavengers, while comparing with the control group of cells without ROS scavenger treatment.

The above cells may be ex vivo cells, in vivo cells, or in vitro cells. The cells, for example, can be gut cells, gut stem cells, or gut epithelial cells.

ROS scavengers of the present invention are identical to the above explanation.

By treating the cells with ROS scavengers, an ROS level is reduced and oxidative stress is thus reduced as explained above. Therefore, oxidative stress of cells can be prevented.

In another aspect, the present invention provides a method for producing cells with stimulated DUOX activation, comprising treating the cells with uracil, uracil precursors, uracil analogs, or uracil-producing non-pathogenic microbes. Further, the present invention provides a method for producing cells with stimulated ROS activation, comprising treating the cells with uracil, uracil precursors, uracil analogs, or uracil-producing non-pathogenic microbes.

The above cells may be ex vivo cells, in vivo cells, or in vitro cells. The cells, for example, can be gut cells, gut stem cells, or gut epithelial cells.

By treating the cells with uracil, uracil precursors, uracil analogs, or non-pathogenic microbes producing uracil, PLCβ and/or DUOX are activated by the above mechanism and ROS generation is stimulated by DUOX activation. Therefore, immunologically activated cells can be produced.

In another aspect, the present invention provides a method for producing cells with reduced ROS levels, comprising treating the cells with ROS scavengers, while comparing with the control group of cells without ROS scavenger treatment.

The above cells may be ex vivo cells, in vivo cells, or in vitro cells. The cells, for example, can be gut cells, gut stem cells, or gut epithelial cells.

ROS scavengers of the present invention are identical to the above explanation.

By treating the cells with ROS scavengers, an ROS level is reduced and oxidative stress is thus reduced as explained above. Therefore, oxidative stress of cells can be prevented.

In another aspect, the present invention provides a method for providing information on gut pathogenicity in isolated bacteria, comprising:

(a) classifying bacteria into the group consisting of uracil-producing autochthony, uracil-producing allochthony, uracil non-producing autochthony, and uracil non-producing allochthony according to uracil production and colonization of the bacteria; and (b) determining bacteria as gut pathogenic bacteria if the bacteria belong to uracil-producing autochthony or uracil non-producing allochthony in step (a) above.

Mode for Carrying out Invention

Hereinafter, the present invention will be described in detail with reference to the following examples. However, these examples are intended only to describe for the purpose of illustrating the invention, but not to limit the range of the present invention to these examples.

EXAMPLE 1

Fly Species and Rearing

In the present invention, the fly lineages including w[1118] UAS-PLCβ-RFP (Ha et al., Nat Immunol 10, pp. 949-957, 2009), MEKK1[Ur3] (Inoue et al., Embo J 20, pp. 5421-5430, 2001), Drs-GFP, Dpt-LacZ (Jung et al., Biotechniques 30, pp. 594-598, 2001), imd[1] (Lemaitre et al., Proc Natl Acad Sci USA 92, pp. 9465-9469, 1995), UAS-DUOX-RNAi (Ha et al., Science 310, pp. 847-850, 2005), norp[7] (Ha et al., Nat Immunol 10, pp. 949-957, 2009), Gαq[1] (Ha et al., Nat Immunol 10, pp. 949-957, 2009), esg-GAL4>UAS-GFP (Micchelli and Perrimon, Nature 439, pp. 475-479, 2006), upd3-GAL4>USA-GFP (Agaisse et al., Dev Cell 5, pp. 441-450, 2003), Su(H)Gbe-LacZ (Bray and Furriols, Curr Biol 11, pp. 217-221, 2001), and Da-GAL4 (Giebel et al., Mech Dev 63, pp. 75-87, 1997) were used. Transgenic flies containing 2XSTAT-GFP were used to monitor JAK-STAT pathway activation (Bach et al., Gene Expr Patterns 7, pp. 323-331, 2007).

*Drosophila* were reared at a temperature of 25° C. The composition of standard corn meal agar media was prepared identically to the description in the previous reference (Shin et al., Science 334, pp. 670-674, 2011). Annexin standard form meal agar media was used for the experiments with germ-free animals or germ-free animals monoassociated with commensal bacteria. Bokinin and propionic acid were omitted from the annexin media.

EXAMPLE 2

Bacterial Strains and Culture Conditions

Carotovora-15, a subspecies of Erwinia carotovora, was obtained from Bruno Lemaitre (Buchon et al., Cell Host Microbe 5, pp. 200-211, 2009b). *Commensalibacter intestini* A911T, *Gluconobacter morbifer* G707T, *Acetobacter pomorum, Lactobacillus plantarum,* and *Lactobacillus brevis* were isolated from the present inventors' laboratory fly stocks (Roh et al., Appl Environ Microbiol 74, pp. 6171-6177, 2008; Ryu et al., Science 319, pp. 777-782, 2008). Bacterial strains identified in humans were obtained from the gene bank of the Korea Research Institute of Bioscience and Biotechnology. The present inventors constructed two URA− mutant bacteria, *E. carotovora*-pyrE::Tn5 and *G. morbifer*-carA::Tn5, by Tn5-mediated random mutant libraries for *E. carotovora* and *G. morbifer.* Detailed methods for Tn5-mediated random mutagenesis and screening strategies are disclosed in Examples below and shown in FIGS. 6a to 6j and 12a to 12e. An *E. carotovora*-pyrE::Tn5-pyrE strain was constructed by introducing pTac3-pyrE into an *E. carotovora*-pyrE::Tn5 strain. The pTac3 expression vectors containing apramycin resistance gene is a modified version of pTac1 vector (Koo et al., EMBO J 22, pp. 2614-2622, 2003). All bacteria were cultured at 30° C. Appropriate antibiotics were added at 50 μg/mL of apramycin and 30 μg/mL of kanamycin, respectively.

EXAMPLE 3

Production of Concentrated Bacterial Supernatants

*E. carotovora* were cultured in M9 minimal media. Because all of the commensal bacteria do not grow on M9 minimal media, various vitamins and essential amino acids were experimented with as disclosed in the previous reference (Foda and Vaughn, 1953). The present inventors confirmed that only *C. intestini* can grow on M9 minimal media with an additional 0.2 mg/mL of p-aminobenzoic acid, 1 mg/mL of pantothenic acid, and 0.2 mg/mL of nicotinic acid. In the late exponential phase, each bacterial supernatant (derived from approx. $10^5$ bacterial cells) was obtained from centrifugation and filtering (pore size of 0.2 mM). Supernatants were lyophilized in Speedvac, and pellets were dissolved in 20 mL of distilled water. The sample was desalinized by adding 100% methanol in a volume 50 times more than that of the sample. Following the centrifugation, the sample was lyophilized in Speedvac, and dissolved in 20 mL of distilled water.

EXAMPLE 4

Analysis of Immune Staining

To examine uracil-induced p38 activation, a 5% sucrose solution containing 20 nM of uracil was orally administered to genetically different adult *Drosophila* (5 to 6 days old) for 2 hours. Midguts were dissected in PBS and fixed with 4% paraformaldehyde for 15 minutes. The midguts were washed three times with PBS containing 0.1% of Triton X-100 for 5 minutes and were cultured in the above solution with additional 5% cow blood serum albumin for 1 hour. Next, the sample was cultured with additional phospho-specific anti-p38 antibody (1:500 dilution; Millipore, Milford, Mass., USA) at 4° C. for 16 hours. The sample was washed five times with PBS containing 0.1% Triton X-100 for 5 minutes and cultured at room temperature for 20 minutes after adding secondary antibodies (1:500 dilution; Alexa Fluor 568 goat anti-rabbit IgG; Invitrogen, Carlsbad, Calif., USA). After washing the sample three times with PBS containing 0.1% Triton X-100 for 5 minutes, the sample was mounted with mounting buffer solution (Vectorshield, Vector Laboratories Inc., Burlingame, Calif., USA) and was analyzed by LSM 700 confocal microscopy (Carl Zeiss, Oberkochen, Germany)

To examine a renewal program for epithelial cells, a 5% sucrose solution containing 20 nM of uracil (for 16 hours) or different bacteria (approx. $5 \times 10^8$ cells; *E. carotovora, E. carotovora*-pyrE::Tn5 and *E. carotovora*-pyrE::Tn5-pyrE for 22 hours) was orally administered to genetically different adult *Drosophila* (5 to 6 days old). For the recovery experiment, *Drosophila* coingested URA– strain (*E. carotovora*-pyrE::Tn5) and 1 nM of uracil. Following the dissection of the gut, the gut was treated with primary antibodies [anti-phospho-histone H3 (1:2000 dilution; Millipore), anti-LacZ (1:1000 dilution; Cappel), or anti-Prospero (1:100 dilution; Developmental Studies Hybridoma Bank)]. Then, the gut was treated with secondary antibodies (Alexa Fluor 568 goat anti-rabbit IgG or Alexa Fluor 488 goat anti-murine IgG (Invitrogen)). DAPI was used for nuclear staining.

EXAMPLE 5

In Vivo ROS Detection in Gut Epithelia

R19S, a recently developed HOCl-specific rhodamine-based dye, was used in this experiment (Chen et al., Chem Commun (Camb) 47, pp. 4373-4375, 2011). R19S was purchased from Futurechem (Seoul, South Korea).

To measure ROS induced by bacteria, different stimulants which are concentrated bacterial supernatants (equivalent to supernatants obtained from approx. $5 \times 10^7$ bacterial cells in the late exponential phase), a high performance liquid chromatography (HPLC) fraction of concentrated bacterial supernatants, as disclosed previously, and a 5% sucrose solution containing 20 nM of uracil or live bacteria (*E. carotovora, E. carotovora*-pyrE::Tn5, and *E. carotovora*-pyrE::Tn5-pyrE, approx. $5 \times 10^8$ cells), were orally administered to genetically different female adult *Drosophila* (5 to 6 days old) for 30 minutes in the absence of R19S, and were then orally administered to genetically different female adult *Drosophila* (5 to 6 days old) in the presence of 10 μM of R19S for 60 minutes.

Furthermore, to measure the basal level of ROS in germ-free animals, *Drosophila* monoassociated with each bacterium (*C. intestini, A. pomorum, L. plantarum, G. morbifer, G. morbifer*-carA::Tn5, *L. brevis,* or *L. brevis*ΔcarA) were experimented with as disclosed above. A 5% sucrose solution containing 10 μM of R19S was orally administered to the monoassociated *Drosophila* (13 days old) for 90 minutes.

Following the R19S ingestion, the midguts were dissected and fixed with 4% formaldehyde. The level of HOCl (ROS level) was visualized by LSM700 confocal microscopy (Carl Zeiss).

For all of the experiments, R19S-positive guts in each animal group (n=approx. 20) were measured by each independent experiment, and data was indicated by at least three repeated and independent experiments. The number of R19S-positive guts in regard to the total numbers of gut samples was indicated as the ratio of ROS-positive guts.

EXAMPLE 6

Analysis of Cell Apoptosis

To measure cell apoptosis in gut cells caused by a long-term exposure to uracil, genetically different germ-free adult *Drosophila* (5 to 6 days old) were maintained on the standard corn meal agar media with a supplemental 1 nM of uracil for 20 days.

To measure gut cell apoptosis induced by *G. morbifer,* germ-free *Drosophila* (WT *G. morbifer* or *G. morbifer*-carA::Tn5) were monoassociated with different *G. morbifer* strains.

To analyze gut cell apoptosis according to elapsed time, existing *Drosophila* were infected with different bacteria (*E. carotovora* or *E. carotovora*-pyrE::Tn5, approx. $5 \times 10^8$ cells) and collected at 16, 24, 48, and 72 hours.

Midguts of female *Drosophila* (20 days old) collected above were used for the analysis of cell apoptosis. Midguts were dissected in PBS, and cell apoptosis analysis was conducted by terminal deoxynucleotidyl transferase (TdT)-mediated dUDP nick end labeling method as disclosed in the previous research (Ryu et al., Science 319, pp. 777-782, 2008).

The cell apoptotic index was indicated by dividing the number of apoptotic cells with respect to the total number of cells and multiplying the value by 100.

EXAMPLE 7

Analysis of GFP and LacZ-Reporter

*Drosophila* containing esg-GAL4> UAS-GFP were used to analyze ISC proliferation and differentiation. A 5% sucrose solution containing 20 nM of uracil (for 16 hours) or different bacteria (*E. carotovora, E. carotovora*-pyrE::Tn5, and *E. carotovora*-pyrE::Tn5-pyrE, approx. $5 \times 10^8$ cells, for 22 hours) was orally administered to *Drosophila* (5 to 6 days old). For the recovery experiment, *Drosophila* coingested a URA− strain (*E. carotovora*-pyrE::Tn5) and 1 nM of uracil.

For the Upd3-JAK-STAT pathway analysis, uracil or bacteria was orally administered to *Drosophila* containing Upd3-GAL4> UAS-GFP or 2× STAT-GFP as disclosed in the above protocol, except for the fact that the ingestion duration was 4 hours. To analyze antimicrobial peptide expression, different stimulants [supernatant concentrated by about 50 nL of different bacteria (supernatant derived from approx. $2.5 \times 10^5$ bacterial cells)] were injected into *Drosophila* containing Drs-GFP or Dipt-LacZ (when imd variable background was present or absent) to infect the flies with sepsis. Dipt-LacZ of fat body was experimented on at 9 hours after injection.

LacZ staining was conducted as disclosed in the previous research (Kwon et al., J Biol Chem 275, pp. 19824-19830, 2000).

EXAMPLE 8

PLCβ Position in Cell Membrane

Genetically modified *Drosophila* containing PLCβ-RFP (UAS-PLCβ-RFP; Da-GAL4) were used to monitor activated PLCβ generation which is targeted in the membrane as disclosed in the previous research (Ha et al., Nat Immunol 10, pp. 949-957, 2009). A 5% sucrose solution containing 20 nM of uracil was ingested by *Drosophila* (5 to 6 days old) for 2 hours.

EXAMPLE 9

RT-PCR Analysis

Fluorescent RT-PCR was conducted to quantify gene expression and double-stranded DNA dye and SYBR green (Perkin Elmer, Waltham, Mass., USA) were used. To detect target gene trascriptomes, Cecropin (Sense, 5'-ATG AAC TTC TAC AAC ATC TTC G-3' (SEQ ID NO: 5); Antisense, 5'-GGC AGT TGC GGC GAC ATT GGC G-3' (SEQ ID NO: 6)), *Diptericin* (Sense, 5'-GGC TTA TCC GAT GCC CGA CG-3' (SEQ ID NO: 7); Antisense, 5'-TCT GTA GGT GTA GGT GCT TCC C-3' (SEQ ID NO: 8)), and DUOX (Sense, 5'-GCT GCA CGC CAA CCA CAA GAG ACT-3' (SEQ ID NO: 9); Antisense, 5'-CAC GCG CAG CAG GAT GTA AGG TTT-3' (SEQ ID NO: 10)) were used, and as a control group, Rp49 (Sense, 5'-AGA TCG TGA AGA AGC GCA CCA AG-3' (SEQ ID NO: 11); Antisense, 5'-CAC CAG GAA CTT CTT GAA TCC GG-3' (SEQ ID NO: 12)) was used. SYBR green analysis was conducted by an ABI PRISM 7700 system (PE Applied Biosystems, Foster City, Calif., USA) according to the manufacturer's instructions. All of the samples were repeated three times and analyzed, and a detected amount of mRNA was normalized with mRNA in the control group. Normalized data was used to quantify the relative amount of mRNA according to cycling threshold analysis. Targeted gene expression was expressed as the relative amount of expression.

EXAMPLE 10

Experiment of Gut Infection and Analysis of the Survival

During the late exponential phase, different bacteria (*E. carotovora, E. carotovora*-pyrE::Tn5, *E. carotovora*-pyrE::Tn5-pyrE, *E. carotovora*-guaA::Tn5, and *E. carotovora*-purC::Tn5) were obtained by the centrifugation, and the pellets were washed with PBS and suspended in a 5% sucrose solution. Without a hunger stage, to continuously provide *Drosophila* with bacteria while being infected, male adult *Drosophila* (5 to 6 days old) were moved to the bottle with filter paper soaked with a 5% sucrose solution containing different bacteria. The filter paper was changed every day. During the recovery experiment, the coingestion of *E. carotovora*-pyrE::Tn5 (+uracil) and 1 nM of uracil or the expression of an *E. carotovora*-pyrE::Tn5 strain, which was genetically recovered by the expression of functional pyrE genes (+pyrE), was utilized.

EXAMPLE 11

Analysis of Bacterial Persistence

To measure gut sustainability of *E. carotovora* strains (*E. carotovora, E. carotovora*-pyrE::Tn5, and *E. carotovora*-pyrE::Tn5-pyrE), a 5% sucrose solution containing approx. $10^{10}$ cells of *E. carotovora* strains were orally administered to female adult *Drosophila* (5 to 6 days old) for 2 hours. Midguts were dissected at 6 hours after ingestion. Midguts, posterior guts, and crops of which the surfaces were sterilized were homogenized and diluted accordingly. These were smeared on a Luria-Bertani agar plate, and some of colony-forming units (CFUs) were obtained from each midgut. During the recovery experiment, the coingestion of *E. carotovora*-pyrE::Tn5 (+uracil) and 1 nM of uracil or the expression of an *E. carotovora*-pyrE::Tn5 strain, which was genetically recovered by the expression of functional pyrE genes (+pyrE), was utilized.

EXAMPLE 12

Measurement of Intracellular Calcium

Intracellular $Ca^{2+}$ was measured by the method disclosed in the previous research (Rosker et al., J Biol Chem 279, pp. 13696-13704, 2004). Briefly speaking, *Drosophila* S2 cells (approx. $10^8$ cells) were loaded with pH 7.4 buffer containing 10 mM glucose, 140 mM NaCl, 1 mM $CaCl_2$, 5 mM KCl, 1 mM $MgCl_2$, and 10 mM HEPES and the solution was treated with 2 mM fura-2-acetoxymethyl ester for 40 minutes at room temperature. The cells were washed twice with pH 7.4 $Ca^{2+}$ chelating buffer containing 10 mM glucose, 140 mM NaCl, 1 mM EDTA, 1 mM EGTA, 5 mM KCl, 1 mM $MgCl_2$, and 10 mM HEPES, and were re-suspended in the same buffer. Then, 20 nM of uracil was added to the cells. Fluorescence was continuously recorded at an interval of 0.5 seconds (excitation at 340 nm and 380 nm; emission at 510 nm) by fluorescent spectrophotometer (Shimadzu, Tokyo, Japan) at room temperature.

EXAMPLE 13

Production of Germ-Free Animals

Germ-free animals were prepared as disclosed in the previous research (Ryu et al., Science 319, pp. 777-782, 2008). To produce germ-free *Drosophila*, bacterial cells (approx. $10^6$ cells) were washed twice with PBS, and germ-free feed was placed into the bottle containing a germ-free embryo. The bottle was maintained in a sterilized cell culturing hood until *Drosophila* reached the adult stage while preventing contamination from other microbes. The *Drosophila* produced were used in the experiment. Commensal bacteria used for the experiment were *C. intestini, A. pomorum, L. plantarum, G. morbifer, G. morbifer*-carA:: Tn5, *L. brevis,* and *L. brevis*ΔcarA. As disclosed in the previous research (Ryu et al., Science 319, pp. 777-782, 2008), all bacteria were cultured on mannitol media except *L. plantarum,* and *L. brevis* was cultured on MRS media.

EXAMPLE 14

Measurement of Survival Duration

Control *Drosophila* and PLCβ-DUOX pathway-mediated mutated *Drosophila* (PLCβ$^{-/-}$ and DUOX-RNAi) were used in the experiment. It is known that PLCβ$^{-/-}$ and DUOX-RNAi flies have a short life span under conventional rearing conditions but a normal life span under germ-free conditions (Ha et al., Nat Immunol 10, pp. 949-957, 2009). Therefore, to examine the effects of uracil on the survival rate of genetically different *Drosophila,* germ-free animals were used. Germ-free animals were reared in germ-free media containing 1 nM of uracil. Germ-free animals were moved to a newly sterilized bottle that had germ-free media containing uracil every 4 or 5 days. *Drosophila* remained germ-free throughout the entire experimental processes. The survival rate was observed in three or more cohort groups, each consisting of about 25 *Drosophila.*

Germ-free *Drosophila* were monoassociated with *G. morbifer* or to *G. morbifer*-carA::Tn5. To measure the effect of *G. morbifer* or that of *G. morbifer*-carA::Tn5 on the host, monoassociated *Drosophila* were moved to a newly sterilized bottle that had germ-free media every 4 or 5 days. *Drosophila* remained germ-free throughout the entire experimental process. The survival rate was observed in 3 or more cohort groups, each consisting of about 25 *Drosophila.*

EXAMPLE 15

Generation of Tn5-Mediated Random Mutants

The present inventors generated two URA− mutant bacteria, *E. carotovora*-pyrE::Tn5 and *G. morbifer-carA::Tn5,* to understand the role of uracil in the body in terms of gut immunity at a molecular level. The present inventors formed a random mutant library for two URA− mutant bacteria, *E. carotovora* and *G. morbifer,* by Tn5-mediated random mutant generation using EZ::Tn5™ <KAN-2>Tnp Transposome™ kit (Epicentre, Madison, Wis., USA) according to the manufacturer's instructions. A preparation for electrocompetent bacterial cells and electroporation processes was disclosed in the previous research (Shin et al., Science 334, pp. 670-674, 2011). About 3,000 and about 6,000 independent mutant colonies were produced from *G. morbifer* and *E. carotovora,* respectively. An *E. carotovora*-pyrE::Tn5-pyrE strain was generated by introducing pTac3-pyrE into an *E. carotovora*-pyrE::Tn5 strain. The pTac3 expression vectors containing apramycin resistance gene are a modified version of pTacl (Koo et al., 2003).

EXAMPLE 16

Measurement of HPLC Analysis

Concentrated bacterial supernatants derived from approx. $10^8$ bacterial cells were prepared based on the method disclosed in Example 3. Supernatants were fractionated at 280 nm in HPLC for 35 minutes by methanol gradient (0% to 10%) in Waters Atlantis™ C18 column (250 mm×4.6 mm and pore size of 5 mm)

EXAMPLE 17

Measurement of NMR Spectrum

NMR experimentation was conducted with a Bruker Avance NMR 900 MHz apparatus (Mannheim, Germany) and Varian Unity INOVA 400 MHz FT-NMR. Chemical shift (d) was reported in parts per million (ppm) compared to tetramethylsilane, which is an internal standard, and a coupling constant (J values) was reported in Hertz. The fractions distinguished by each HPLC were evaporated, and the residues were dissolved in deuterium oxide ($D_2O$), deuterated methanol ($CH_3OH-d_4$), or deuterated dimethyl sulfoxide (DMSO-$d_6$) for the NMR experiment. All of the 1-dimensional (1D) $^1H$ NMR spectra were recorded at a spectrum width of 13 ppm, 8192 data points, and a temperature of 298 K or 308 K. Two-dimensional (2D) COSY, TOCSY (mixing time 88 ms), $^1H$—$^1H$ homonuclear NOESY (maintaining a mixing time of 150 ms and 300 ms), HSQC, and $^1H$—$^{13}C$ and $^1H$—$^{15}N$ heteronuclear HMBC were recorded at 4096 data points in the $t_2$ range or in a range that was increased by 512. A sine bell function shifted by more than 90° was used in $t_2$ and $t_1$ dimensions prior to Fourier transformation of NOESY data, whereas a sine bell function biased by more than 30° was used for TOCSY and COSY. The final spectrum matrix was composed of 1024× 1024 of $^1H$ frequency (F2 and F1) dimensions. To fully determine the structure of active organismal elements from an HPLC fraction, NMR proton signal data was allocated according to the combination of 2D $^1H$—$^1H$ experiments including NOESY, COSY, and TOCSY. A carbon-carbon signal type was determined by the combination of 1D DEPT and carbon integration experiments by a zgig30 plus program, 2D $^1H$—$^{13}C$ HSQC, and HMBC experiments. Bacterial supernatants labeled with $^{15}N$ were fractioned by HPLC and nitrogen atoms in active organismal elements were analyzed by a 2D $^1H$—$^{15}N$ HSQC NMR spectrum.

EXAMPLE 18

Measurement of Mass Analyzer

A mass analysis was conducted by an ABI ESI-TOF mass spectroscope (Applied Biosystems) with an attached electron ionization (EI) feeder or a GC-2010 mass spectroscope (Shimadzu). The activated fractions distinguished by HPLC were prepared by the above method to prepare NMR samples, except for the part wherein the residues were dissolved in desalinized water prior to MS analysis.

EXAMPLE 19

Quantitative Analysis of Uracil by LC-MS/MS

LC was conducted by Agilent 1100 (Agilent Technologies, USA) with a binary pump, a vacuum microdegasser, a column oven, and an automatic sampler which can control temperature. Isolation was achieved in a Proshell 120 EC-C18 column (3.0 mm×50 mm; particle size of 2.7 μm; Agilent Technologies, USA). The mobile phase was composed of an 80% acetonitrile aqueous solution which had a velocity of flow of 0.3 mL/min. The temperature of the column was maintained at 35° C. LC was conducted by API 4000 QTRAP (Applied Biosystems, Foster City, Calif., USA). Important variables of the spectrometer were optimized manually as shown below: sprayer temperature of 400° C., sprayer voltage of 5500 V, spraying (GS1) gas of 50 psi, heated (GS2) gas of 50 psi, and CAD gas of 4 psi. The mass spectrum analysis was conducted in multiple reaction monitoring (MRM) mode to detect uracil precursor ions and product ions (precursor ion→product ion: 113.0→70.1 (m/z)). All data was processed by Analyst software 1.4.2 (Applied Biosystems, USA). A standard solution and a sample solution for a standard curve were prepared by the method disclosed in the previous research with additional local transformation (Buchel et al., Biomed Chromatogr, 2012; Mutlu et al., Chem Res Toxicol 25, pp. 391-399, 2012; Van Dycke et al., J Chromatogr B Analyt Technol Biomed Life Sci 878, pp. 1493-1498, 2010). To produce a crude solution, uracil was dissolved in distilled water (final concentration of 1 mg/mL). The standard solution for the standard curve was prepared by diluting the crude solution with M9 media so that the concentration reached 8000 ng/mL, 1600 ng/mL, 320 ng/mL, 65 ng/mL, 13 ng/mL, and 0 ng/mL. Supernatants of each bacteria cultured from M9 minimal media (equal to supernatants obtained from approx. $10^8$ bacterial cells) were obtained by the centrifugation and filtering (pore size of 0.2 mM). C. intestini was cultured on M9 media after addition of p-aminobenzoic acid (0.2 mg/mL), pantothenic acid (1 mg/mL), and nicotinic acid (0.2 mg/mL) to M9 minimal media. Filtered bacterial supernatants were mixed with 100 μL of 5-bromouracil (100 μg/mL aqueous solution was prepared and used as an internal standard), vortex-mixed by adding 3 mL of 9:1 ethyl acetate:isopropyl alcohol (v:v), centrifuged at 1100 rpm for 10 minutes, and extracted. The fractioned sample of the upper organic layer (2.4 mL) was dried under nitrogen gas at 40° C. and evaporated. The residues were ultrasonicated for 1 minute, vortex-mixed for 1 minute, and dissolved in 100 μL of methanol. The supernatants and the standard solution of each sample were moved to the minute-volume insert (volume of 250 μL) and inserted into the LC-MS/MS system to analyze the final solution of 5 μL.

EXAMPLE 20

ROS Measurement in C. elegans

C. elegans were raised and maintained as disclosed in the previous research (Chavez et al., Infect Immun 77, pp. 4983-4989, 2009). As disclosed in the previous research, L1 nematodes were fed with bacteria containing Ce-DUOX1-RNAi vectors throughout the step L4 to introduce Ce-DUOX1-RNAi (Chavez et al., Infect Immun 77, pp. 4983-4989, 2009). Standard feeding system RNAi process using Ce-DUOX1-RNAi may cause a developmental disability which indicates a serious level of mortality. As disclosed in the previous research, to give a partial knockdown effect, Ce-DUOX1-RNAi bacteria were mixed with bacteria containing control RNAi at a ratio of 1:70. In the early adult stage, nematodes were obtained and washed with M9 minimal media. Nematodes (about 200 to 300 individuals) were placed in a 96-well plate comprising uracil-containing media (50 mL) at 20° C. for 2 hours.

DUOX-dependent $H_2O_2$, as basically disclosed in the previous research (Chavez et al., Infect Immun 77, pp. 4983-4989, 2009), was measured at room temperature for 2 hours following addition of 100 mM of Amplex UltraRed solution (Invitrogen) and 200 mL of reacting buffer including 0.2 units/mL of horseradish peroxidase (Sigma). Fluorescence of each sample was measured by fluorescent microplate readers at 530 nm of excitation wavelength and 590 nm of emission wavelength. A standard curve was produced by the known concentration of $H_2O_2$.

EXAMPLE 21

Isolation and Culturing of Human Epithelial Cells

Human middle turbinated bone specimens were obtained from healthy volunteers after the research proposal was approved by Yonsei University College of Medicine Audit Committee. The culture system used for normal human nasal epithelial (NHNE) cells is disclosed in the previous research (Yoon et al., Am J Respir Cell Mol Biol 16, pp. 724-731, 1997; Yoon et al., Ann Otol Rhinol Laryngol 109, pp. 594-601, 2000). Briefly speaking, two passages of NHNE cells ($1\times10^5$ cells/culture) were inoculated into a Transwell-transparent culturing insert characterized by 24.5 mm and 0.45 μm pore sizes (Costar Co., Corning, N.Y., USA) containing 0.5 mL of culturing media. The cells were cultured in a 1:1 mixture containing basic epithelium growth media including all additives disclosed in the previous research (Yoon et al., Ann Otol Rhinol Laryngol 109, pp. 594-601, 2000) and Dulbecco' s Modified Eagle Medium (DMEM). The cells were cultured and grown for the first 9 days while being soaked in the media, and during this period, the media was changed on the first day and changed every day since then. Air-liquid interface (ALI) was formed on the $9^{th}$ day after removing the apical part of the media and providing the base section as feed. After ALI was formed, the culturing media was changed every day. All of the experiments were conducted 3 days after the ALI formation. Human intestinal Caco-2 adenocarcinoma cells provided by American Type Culture Collection (Manassas, Va., USA) were maintained in DMEM containing 10% (v/v) cow fetus blood serum and antibiotics (penicillin-streptomycin) at a standard culturing condition of 37° C. The cells were grown on a 12-well plate.

EXAMPLE 22

Measurement of ROS in Human Epithelial Cells

After stimulating NHNE cells or Caco-2 cells, the cells were washed with Hanks' balanced salt solution (HBSS), were placed in Krebs-Ringer solution containing 5 μM of 2',7'-dichlorofluorescin diacetate (DCF-DA; Molecular Probes, Eugene Oreg., USA), and cultured in darkness for 10 minutes. The cells were washed with 1 mL of HBSS at least five times to eliminate extracellular ROS. The culture plate was speculated by Zeiss Axiovert 135 resupination confocal microscopy with x20 Neofluor objective lens and Zeiss LSM 410 confocal additional apparatus. Fluorescence was measured at an excitation wavelength of 488 nm and an emission wavelength ranging from 515 nm to 540 nm. To obtain the mean value of relative fluorescent intensity, seven domains were randomly selected from each culture plate and the domains were used for the comparison between the means. All of the experiments were repeated at least three times.

EXAMPLE 23

Pseudo-Type Retrovirus Generation and Transduction

The shuttle vector containing an internal ribosome entry site (IRES) based on an SV40 large T-antigen nuclear localization signal was produced from pBS-KS. shRNA (DUOX2 shRNA, 5'-GCC ATC AGG AGT GGC ATA AAT TAG TGA AGC CAC AGA TGT AAT TTA TGC CAC TCC TGA TGG C-3' (SEQ ID NO: 13), which targets human DUOX2 mRNA, was produced. Complementary single-chain DNA oligonucleotides were annealed and inserted into IRES of the shuttle vector 5'. DNA fragments including human DUOX2 shRNA were separated from the shuttle vector and were inserted into the pLZRS vector. shRNA (5'-CAA CAA GAT GAA GAG CAC CAA CTC GAG TTG GTG CTC TTC ATC TTG TTG-3' (SEQ ID NO: 14)) of the pLZRS was used as a control group. A highly potent virus was prepared as disclosed in the previous research (Kim et al., Neuron 38, pp. 17-31, 2003). Human 293-derived retrovirus packaging cell strains (293GPG) were transfected with plasmids by Superfect Reagent (Qiagen, Valencia, Calif., USA), wherein tetracycline-inducing plasmids coding vesicular stomatitis virus G-protein could reproduce in the 293GPG. Until the virus was induced, the cells were cultured on the media including tetracycline. Supernatants (without tetracycline) including a retrovirus collected after 3 days were filtered with a 0.45 μm polyethersulfone membrane and concentrated by ultracentrifugation. Prior to the experiment, NHNE cells or Caco-2 cells were treated twice with the retrovirus (Multiplicity of infection (MOI): 10) for 2 days.

EXAMPLE 24

Statistical Analysis

Comparisons of two samples were made by either the Student's t-test or the Mann-Whitney U-test. Comparisons of multiple samples were made by an ANOVA. The Kaplan-Meier log-rank test was used for the statistical analysis of fly survival experiments. The p values less than 0.05 were considered statistically significant. SPSS software (Chicago, Ill., USA) was used for all of the analyses.

Based on the above-described Examples, the Experimental examples are obtained as below.

EXPERIMENTAL EXAMPLE 1

Measurement of DUOX-Dependent Immune Response Based on Bacterial Types 1-1. Measurement of DUOX-Dependent ROS by R19S R19S, which is a dye based on recently developed HOCl-specific rhodamine, was used in Examples of the present invention. For the in vivo ROS imaging, a specific and sensitive method for DUOX-dependent ROS detection based on a recently developed rhodamine-based sensor R19S, was used. R19S is highly specific to DUOX-dependent HOCl, including hypothiocyanite, and is unable to react with various other ROS (FIG. 2a). The experiment below was conducted by measuring the ROS level induced by bacteria and the initial ROS level.

1-2. Measurement of ROS Level Following Administration of Commensal Microbes and Opportunistic Pathogens Adult *Drosophila* were subjected to oral ingestion with *carotovora*-15, which is a subspecies of *Erwinia carotovora*. *E. carotovora* is considered to be an opportunistic pathogen in *Drosophila* because it does not harm the normal host but can cause severe lethality when the host's DUOX-dependent gut immunity is impaired.

As expected, *E. carotovora* was able to induce DUOX-dependent ROS generation at 1 to 3.5 hours following bacterial ingestion mainly in the anterior midgut region (FIGS. 1a, 2b, and 2c). On the other hand, bacterial-induced ROS generation was at a basal level when flies were fed major symbiotic gut bacteria. For reference, *Commensalibacter intestini* (commensal bacteria in the gut) A911$^T$, *Acetobacter pomorum*, and *Lactobacillus plantarum* account for more than 98% of the total commensal population of the laboratory *Drosophila* (FIG. 1a).

Further analysis showed that gut ROS generation was specifically induced by diverse ranges of opportunistic pathogens, but mostly absent in distinct bacterial species that act as commensal microbiota in *Drosophila* (FIG. 2d). This observation suggests that distinction between commensal and pathogenic bacteria in *Drosophila* can be made on the basis of the in vivo DUOX-activating ability of each bacterium.

Furthermore, in contrast to live or lysed *E. carotovora*, formalin-fixed dead *E. carotovora* did not efficiently induce ROS generation, suggesting that a molecule secreted by bacterial metabolism is responsible for DUOX activation (FIGS. 1b and 2e).

To confirm the possible existence of live bacteria-secreted ligands, which is a cause for DUOX activation, culture supernatants of different bacterial species were prepared. Because complete bacterial growth media such as Luria-Bertani media was confirmed and ROS generation in the gut was induced, all of the bacteria used in these experiments were grown on minimal growth media, except for *A. pomorum* and *L. plantarum* due to their total absence of growth on the minimal growth media. It was confirmed that *E. carotovora* culture supernatants effectively induced ROS generation in a DUOX-dependent manner, but *C. intestini* culture supernatants did not, as evidenced by the similar induction levels of Relish/NF-kB-dependent AMP gene expression (FIG. 1c). In contrast to this differential activation of DUOX-dependent gut immunity, culture supernatants of both *E. carotovora* and *C. intestini* lead to comparable levels of IMD pathway activation in the systemic immunity (FIG. 1d). Furthermore, gut infection experiments with live bacteria, but not formalin-fixed dead bacteria, showed that both gram-negative pathogens and gram-negative commensal bacteria induced similar gut IMD pathway activation (FIG. 1e). These findings indicate that both *E. carotovora* and *C. intestini* secrete similar levels of peptidoglycan, the known IMD-pathway-activating MAMP. Taken together, these findings indicate that two distinct mechanisms, the IMD pathway and the DUOX-activation pathway, are operating concomitantly to mount an immune response against pathogens. As *E. carotovora*, but not *C. intestini*, is able to induce DUOX activation, *E. carotovora* may secrete unknown ligands for gut DUOX activation.

EXPERIMENTAL EXAMPLE 2

Analysis of DUOX-Activating Ligands

To determine the molecular nature of DUOX-activated ligands, *E. carotovora* culture supernatants were purified with reverse phase high performance liquid chromatography (HPLC).

The DUOX-activating and ROS-inducing ability of HPLC-purified fractions were examined, and a fraction found in the *E. carotovora* culture supernatants was shown to strongly induce in vivo ROS generation in the gut epithelia in the body, whereas a peak with the similar retention time in the *C. intestini* culture supernatants did not show any activity (FIG. 3a). The HPLC-purified fraction was subsequently subjected to structural analysis by mass spectrometry and nuclear magnetic resonance (NMR). Chemical analysis revealed that this fraction contained uracil (FIGS. 4a and 4b). When the HPLC-purified uracil was compared with synthetic uracil by spectrum analysis (FIG. 3a) and NMR analysis (FIG. 4c), the profiles were indistinguishable, confirming that the pathogen-derived DUOX-activating ligand is uracil.

To further investigate whether uracil release occurs in a wide range of bacteria including human pathogens, quantitative analysis of uracil in the supernatant of bacteria cultured in vitro was performed by liquid chromatography tandem mass spectrometry (LC-MS/MS). Complete media such as Luria-Bertani media was found to contain high amounts of uracil (approx. 10 g/mL) and minimal growth media were used to measure the level of uracil secreted from the bacteria. Only seven bacterial species were capable of surviving in the minimal media among 32 tested bacteria, and their culture supernatants were subjected to the LC-MS/MS analysis. The result showed that pathogens, such as *Vibrio fluvialis, Klebsiella pneumonia, Shigella sonnei, Pseudomonas aeruginosa,* and *Serratia marcescens,* secreted a significant amount of uracil (approx. 70 ng to 150 ng per $10^8$ cells) (FIG. 4d).

Consistent with the above results (FIG. 3a), *E. carotovora* secreted high amounts of uracil (approx. 200 ng/$10^8$ cells), whereas *C. intestini* did not (FIG. 4d). In conclusion, it was confirmed that the above bacteria secreted a distinct amount of uracil, a DUOX-activating ligand.

EXPERIMENTAL EXAMPLE 3

Uracil Acting as a Specific Agonist for Gut-Innate Immunity

As previously indicated, the result showed that uracil ingestion can activate both the DUOX-activity pathway (PLC activation evidenced by membrane localization of the active form of PLC and by $Ca^{2+}$ mobilization) (FIGS. 3b and 3c) and the DUOX-expression pathway (p38 MAPK activation and DUOX gene induction) (FIGS. 3d and 3e). Uracil-induced activation of all DUOX-regulatory pathways lead to the generation of large amounts of gut ROS in a PLCβ-DUOX signaling-dependent manner (FIG. 3f). It was shown that the presence of commensal bacteria in the gut could not inhibit the ROS-generating ability of uracil, indicating that commensal bacteria are unable to suppress uracil-induced ROS generation (FIG. 4e). As a result of coingestion of uracil with an antioxidant chemical, N-acetylcysteine, DUOX-dependent ROS could not be detected (FIG. 3f).

Dose-dependent analysis of uracil showed that uracil is capable of inducing gut ROS generation from 0.01 nM and most effectively in a range of 1 nM to 20 nM (FIG. 5a). When the present inventors tested the ROS-inducing ability of various uracil-related molecules (other purine and pyrimidine nucleobases, as well as eight different pyrimidine analogs including 5-fluorouracil), it was found that only uracil is capable of activating DUOX (FIGS. 5a and 5b), demonstrating the high specificity of uracil in DUOX-dependent ROS generation in *Drosophila* gut epithelia. Furthermore, uracil was able to activate DUOX-dependent ROS generation in C. elegans and human mucosal epithelial cells (FIGS. 4g and 4i).

At present, it is not known how uracil activates PLCβ-induced $Ca^{2+}$ for DUOX-dependent ROS generation. Given that Gαq protein is also required for uracil-induced ROS generation (FIG. 5c) and that a Gαq-PLCβ-$Ca^{2+}$signaling pathway acts as one of the main downstream signaling events of GPCRs, it is plausible that GPCR is involved with uracil recognition. In contrast to its ability to activate the DUOX pathway, uracil was unable to activate the gut IMD pathway leading to AMP production (FIG. 3d). These results demonstrate that uracil is a specific agonist for the gut-innate immunity capable of inducing DUOX-dependent ROS production, but not IMD-dependent AMP production.

EXPERIMENTAL EXAMPLE 4

Analysis of Relationship Between Uracil Production and Pathogenicity Using Uracil Non-Producing Mutants All of the above findings suggest that the gut epithelia selectively mount a DUOX-dependent antimicrobial program against pathogens by sensing pathogen-derived uracil. It was inferred that opportunistic pathogens lacking uracil production would evade DUOX immunity and become virulent to the host. To assess the role of pathogen-released uracil on DUOX activation in vivo, the present inventors examined gut ROS generation following infection with a uracil non-secretory mutant (URA−) pathogen devoid of uracil biosynthesis ability.

In order to generate uracil non-secretory mutants, an *E. carotovora* mutant library was generated. In order to construct the *E. carotovora* mutant library, Tn5-mediated random mutagenesis was performed on *E. carotovora* strains, wherein Tn5 is a transposon (Tn, which is a unit of DNA that has a specific structure that can metastasize DNA molecules in the cells), and subsequently a single URA− strain was isolated by screening up to 6000 mutant strains (FIG. 6a). Sequencing analysis showed that this URA− strain had a Tn5 insertion within the orotate phosphoribosyltransferase gene (pyrE, a gene involved in uracil biosynthesis) (FIG. 6b).

No apparent morphological and/or physiological differences were found between the wild type (WT) and URA− strain when these bacteria were cultured in vitro (FIGS. 6c and 6f). Furthermore, both WT and URA− strain induced IMD-dependent systemic and gut AMP expression at similar levels (FIGS. 6g and 6h).

The gut infection experiments showed that the uracil non-secretory pyrE mutant strain (*E. carotovora*-pyrE::Tn5), but not other nucleobase non-secretory (other nucleobase-auxotrophic) mutant strains such as guanine- and adenine non-secretory mutants, had significantly reduced ROS production when compared to the gut infection with the parental WT *E. carotovora* strain (FIGS. 7a, 6i, and 6j). Furthermore, a normal level of infection-induced ROS in the gut was seen following either coingestion of uracil with URA− strains or ingestion of functionally recovered URA− strains (i.e., *E. carotovora*-pyrE::Tn5 strains that ectopically express pyrE) (FIG. 7a). These results demonstrated that the host mounts DUOX-dependent gut immunity by sensing bacterial-derived uracil in vivo.

EXPERIMENTAL EXAMPLE 5

Effect of Uracil on Gut Stem Cells and Gut Cell Homeostasis

Recently, epithelial damage associated with bacterial infection in the gut was shown to accelerate the renewal program of gut cells through intestinal stem cell (ISC)

stimulation, which is essential for gut cell homeostasis and host survival against infection. Because DUOX-dependent ROS have recently been shown to be involved in controlling ISC turnover during gut infection, it was confirmed whether uracil is the bacterial-derived ligand that controls the epithelial cell renewal program.

To accomplish this, the present inventors performed gut infection experiments with a WT or URA− strain and analyzed escargot-positive cells using the escargot-GAL4>UAS-GFP system, which allows the identification of ISCs, enteroblasts, and newly synthesized gut cells. The results showed that high numbers of escargot-positive cells were present in the midguts of WT bacterial-infected flies in a PLCβ-dependent manner, but that escargot-positive cells were significantly reduced in the midguts of URA− bacterial-infected flies (FIG. 7b). Because ISCs are the sole group of dividing cells in the midgut, the present inventors further examined the number of dividing cells using antiphosphorylated histone 3 (PH3) antibodies to quantitative the mitotic activity. The results showed that the number of PH3-positive cells was clearly reduced following URA− pathogen infection when compared to WT pathogen infection (FIGS. 7c and 8a). When the present inventors examined Su(H)Gbe-lacZ (a specific marker for enteroblasts) and Prospero (a specific marker for enteroendocrine cells), it was found that WT pathogen infection but not URA− pathogen infection increased the number of enteroblasts in a PLCβ-dependent manner (FIGS. 7d and 8b). However, no difference in the number of enteroendocrine cells was observed between WT pathogen-infected gut and URA− pathogen-infected gut (FIG. 7d). Consistent with this impaired epithelial cell renewal process observed in the URA− pathogen infection, more pronounced apoptosis was found in the URA− pathogen-infected gut compared to that seen in WT pathogen-infected gut (FIG. 8c). Because the expression of cytokine Unpaired-3 (Upd3) in gut cells and subsequent activation of Janus kinase signal transducers and activators of transcription (JAK-STAT) signaling in ISCs and enteroblasts are known to be essential for enterocyte differentiation, the present inventors examined whether bacterial-derived uracil is required for Upd3-JAK-STAT signaling activation. Analysis of reporter transgenic flies showed that the number of cells showing Upd3 expression and subsequent STAT activation was clearly reduced following URA− pathogen infection when compared to WT pathogen infection (FIG. 7e) Importantly, either coingestion of uracil with a URA− strain or ingestion of a functionally recovered URA− strain was sufficient to restore infection-induced Upd3-JAK-STAT signaling activation, ISC proliferation, and differentiation as well as enteroblast accumulation (FIGS. 7b and 7e). Because pathogen-induced Upd3-JAK-STAT pathway activation was abolished in the absence of PLCβ (FIG. 7e), it could be confirmed that the bacterial-derived uracil activates the PLCβ-DUOX-ROS pathway, which in turn acts as an upstream event of the Upd3-JAK-STAT pathway for infection-induced epithelial cell renewal. Furthermore, uracil ingestion alone was sufficient to trigger the Upd3-JAK-STAT pathway activation and epithelial cell renewal process in a PLCβ-dependent manner (FIGS. 10a to 10e). All of these results together indicate that bacterial-derived uracil is the key factor responsible for bacterial-modulated ISC turnover and the epithelial cell renewal program for gut cell homeostasis during gut infection.

EXPERIMENTAL EXAMPLE 6

Recognition of Pathogen-Derived Uracil and Survival of Host

As gut immune responses were virtually abolished in the case of infection with URA− pathogens, the bacterial persistence and host survival rate following gut infection with these bacteria were examined. When the persistence of these bacteria in the gut was examined, it was found that the URA− pathogens persisted longer than the WT pathogens in the midgut region (FIG. 9a).

No significant difference in terms of bacterial persistence was observed between WT and URA− pathogens in the anterior and posterior parts of the digestive tract (i.e., crop and hindgut, respectively), suggesting that ingested bacteria are mainly controlled by uracil-modulated gut immunity in the midgut. The prolonged persistence of URA− pathogens was abolished when the flies were subjected to coingestion of URA− pathogens with uracil or ingestion of a functionally recovered URA− strain (FIG. 9a). Importantly, the present inventors found that flies were more susceptible to infection with URA− pathogens, showing a poor survival rate after infection, whereas the flies were not adversely affected by infection with WT pathogens or other nucleobase non-secretory mutants (FIG. 9b). Furthermore, it was found that coingestion of uracil with a URA− strain or ingestion of a functionally recovered URA− strain was sufficient to restore the host survival rate (FIG. 9), demonstrating that URA− pathogen-induced pathology was due to a lack of uracil in the gut lumen. Taken together, these results demonstrate that host survival against gut infection depends on recognition of pathogen-derived uracil and subsequent activation of DUOX-dependent gut immunity.

EXPERIMENTAL EXAMPLE 7

Effect of Chronic Activation of DUOX-Dependent Gut Immunity Caused by Long-Term Uracil Exposure ROS dysregulation has a critical impact on the pathogenesis of many important diseases in mucosal epithelia. Considering the DUOX-activating and ROS-generating ability of bacterial uracil, the present inventors hypothesized that constitutive exposure to uracil could produce harmful effects on host physiology. Because it is known that PLCβ$^{-/-}$ and DUOX-RNAi flies have a short life span under conventional rearing conditions but a normal life span under germ-free conditions, germ-free animals were used to examine host physiology following long-term ingestion of uracil. Extensive apoptosis in gut cells was found, which ultimately led to the lethality of control flies in a dose-dependent manner (FIGS. 9c, 9d, 10f, and 10g). Importantly, this uracil-induced host pathology was completely absent in PLCβ$^{-/-}$ or DUOX-RNAi flies (FIGS. 9c, 9d, 10f, and 10g), indicating that uracil induces host cellular damage in a PLCβ-DUOX-dependent manner Taken together, these findings showed that chronic activation of the PLCβ-DUOX signaling-dependent gut immunity by long-term uracil exposure is detrimental to the host due to the excess ROS generation. Because indigenous gut microbiota permanently reside in association with the peritrophic membrane of the midgut epithelia, the above results imply that a gut-dwelling autochthonous bacteria releasing uracil in a constitutive manner may act as a colitogenic factor leading to host pathology.

EXPERIMENTAL EXAMPLE 8

Effect of Chronic Activation of the DUOX-Dependent Gut Immunity Due to Long-Term Uracil Release from Autochthonous Bacteria Although some gut symbiotic microbiota are generally beneficial to the host physiology, others can also lead to host pathogenesis in certain circumstances, such as gut dysbiosis, a condition whereby an overgrowth of one or more normal species making up the microflora causes gut dysfunction and diseases. Although such abnormalities of microbiota have been associated with many diseases including inflammatory bowel disease, the molecular mechanism by which gut dysbiosis causes host pathology is poorly understood. In *Drosophila*, it was previously demonstrated that overactivation of IMD-dependent immunity can induce gut dysbiosis, leading to an overgrowth of *G. morbifer* G 707$^T$, a minor member of the WT gut microflora. The overgrowth of *G. morbifer* acts as a direct cause of gut pathology and host lethality. When the *G. morbifer* population is dominant in the gut (e.g., in the absence of other commensal community members, such as in the case of germ-free animals monoassociated with *G. morbifer*), the present inventors observed that *G. morbifer* colonized the midgut region (FIG. 12*a*). When the ROS production in animals monoassociated with *G. morbifer* was examined, chronic ROS generation accompanying severe gut cell apoptosis in a PLCβ-DUOX signaling-dependent manner was found (FIGS. 11*a* and 11*b*). It was further found that *G. morbifer*-induced ROS were colocalized with colonized bacteria in a PLCβ-DUOX-dependent manner, most intensively in the anterior midgut region (FIG. 12*b*). However, other commensal members such as *A. pomorum, C. intestini,* and *L. plantarum* could not induce chronic ROS generation when each of these major bacteria was monoassociated with germ-free animals (FIGS. 11*a*, 12*b*, and 12*c*). Because the *G. morbifer*-induced chronic DUOX activation is likely the cause of gut pathology, it was hypothesized that the constitutive uracil release due to the permanent presence of *G. morbifer* in the gut was the major causal element of *G. morbifer*-induced host pathogenesis. A mutation in carbamoyl phosphate synthetase (carA) is known to induce uracil auxotrophs. Therefore, a URA− mutant strain of *G. morbifer* carrying a mutation on the carA gene (*G. morbifer*-carA::Tn5) was isolated using the transposon-based random mutant library by screening approx. 3000 mutant strains (FIGS. 12*d* and 12*e*) in order to validate the in vivo role of *G. morbifer*-derived uracil on chronic DUOX activation. Importantly, single isolation of germ-free flies with a *G. morbifer*-carA::Tn5 strain showed that this URA− strain did not provoke constitutive ROS generation in the gut (FIG. 11*c*), and led to significantly reduced gut cell apoptosis (FIG. 11*d*), in contrast to its parental *G. morbifer* strain. When the colony-forming units (CFUs) of colonized bacteria in the gut were examined, it was found that the *G. morbifer*-carA::Tn5 strain colonized gut epithelia as efficiently as the WT *G. morbifer* strain (FIG. 11*e*), confirming that healthy host phenotypes found in the gut of animals monoassociated with *G. morbifer*-carA::Tn5 were not due to the reduction of colonizing bacterial numbers. When the survival rate of flies monoassociated with *G. morbifer* was examined, it was found that the *G. morbifer* strain leads to early host death (FIG. 11*f*), showing its pathogenic nature. Importantly, however, flies monoassociated with *G. morbifer*-carA::Tn5 showed survival rates that were comparable to those of the control animals (FIG. 11*f*). *G. morbifer*-induced host mortality observed in control flies was abolished in the absence of the PLCβ-DUOX pathway because no difference in the survival rate was observed between *G. morbifer* monoassociation and *G. morbifer*-carA::Tn5 monoassociation in the case of DUOX-RNAi or PLCβ$^{-/-}$ animals (FIG. 11*f*), demonstrating that *G. morbifer*-induced disease phenotypes can be effectively reversed by diminishing either bacterial uracil production or host DUOX activity. Furthermore, monoassociation of gram-positive *L. brevis,* the other minor member of WT gut microflora, with germ-free animals showed that *L. brevis* can also provoke a disease phenotype due to uracil-induced chronic DUOX activation similar to that seen in animals monoassociated with *G. morbifer.* Taken together, the present inventors concluded that the steady release of uracil from two minor commensal bacteria and the consequent chronic activation of PLCβ-DUOX signaling-dependent gut immunity act as a direct cause of colitogenesis and host mortality.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A method for treating infectious diseases caused by uracil non-secretory (URA−) bacteria, comprising administration of a composition comprising isolated uracil or uracil-secreting opportunistic pathogens as an active ingredient to a subject in need.

2. The method according to claim 1, wherein the uracil non-secretory (URA−) bacteria are allochthonous bacteria.

3. The method according to claim 1, wherein the uracil, uracil precursors, uracil analogs, or uracil-secreting opportunistic pathogens activate dual oxidase (DUOX) in gut cells.

4. The method according to claim 3, wherein the DUOX activation increases a level of reactive oxygen species (ROS) in gut cells.

5. The method according to claim 1, wherein the composition further comprises pharmaceutically acceptable carriers, excipients, or diluents.

* * * * *